United States Patent
Sparks et al.

(10) Patent No.: US 11,319,578 B2
(45) Date of Patent: *May 3, 2022

(54) ASSAY SYSTEMS FOR GENETIC ANALYSIS

(71) Applicant: Ariosa Diagnostics, Inc., San Jose, CA (US)

(72) Inventors: Andrew Sparks, San Jose, CA (US); Arnold Oliphant, San Jose, CA (US); Jacob Zahn, San Jose, CA (US); Ken Song, San Jose, CA (US); John Stuelpnagel, San Jose, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/851,363

(22) Filed: Dec. 21, 2017

(65) Prior Publication Data

US 2018/0187247 A1 Jul. 5, 2018

Related U.S. Application Data

(63) Continuation of application No. 13/205,570, filed on Aug. 8, 2011, now Pat. No. 9,890,421, which is a continuation-in-part of application No. 13/013,732, filed on Jan. 25, 2011, now abandoned.

(60) Provisional application No. 61/371,605, filed on Aug. 6, 2010.

(51) Int. Cl.
| | |
|---|---|
| *C12Q 1/6827* | (2018.01) |
| *C12Q 1/6862* | (2018.01) |
| *C12Q 1/6809* | (2018.01) |

(52) U.S. Cl.
CPC ......... *C12Q 1/6827* (2013.01); *C12Q 1/6809* (2013.01); *C12Q 1/6862* (2013.01)

(58) Field of Classification Search
CPC ... C12Q 1/6827; C12Q 1/6809; C12Q 1/6862
See application file for complete search history.

(56) References Cited

U.S. PATENT DOCUMENTS

2001/0051341 A1* 12/2001 Lo .................. C12Q 1/6879
435/6.12
2008/0090239 A1* 4/2008 Shoemaker ........ G01N 33/5091
435/6.12

OTHER PUBLICATIONS

Chiu et al. Trends in Genetics. 2009. 25(7):324-331. (Year: 2009).*

* cited by examiner

*Primary Examiner* — Joseph G. Dauner
(74) *Attorney, Agent, or Firm* — Jennifer Rosenfield; Mintz Levin

(57) ABSTRACT

The present invention provides assays systems and methods for detection of chromosomal abnormalities and status of single loci associated with monogenic or polygenic traits in a sample containing nucleic acids from a maternal and a fetal source.

30 Claims, 15 Drawing Sheets

Specification includes a Sequence Listing.

| Sample | Sample Tag | Fetal Gender | Genome Equivs. | Maternal Karyotype | Fetal Karyotype | Mater Age | GestAge (Day) | # Loci DiffPoly | % Fetal | Mean18 | Mean21 | Prop18 | Prop21 | ZStat18 | ZStat21 |
|---|---|---|---|---|---|---|---|---|---|---|---|---|---|---|---|
| 1 | TGTCCCC | M | 2293 | 46XX | 46XY | 45 | 110 | 38 | 0.210138 | 1005.426 | 999.4412 | 0.501493 | 0.498507 | 0.48436 | -0.48436 |
| 2 | ATCCTCC | F | 3593 | 46XX | 46XX | 37 | 131 | 45 | 0.096075 | 996.6228 | 998.7823 | 0.499459 | 0.500541 | -0.84491 | 0.84491 |
| 4 | GCCAACC | F | 1469 | 46XX | 46XX | 34 | 121 | 26 | 0.235051 | 991.0624 | 997.5193 | 0.498376 | 0.501624 | -1.55236 | 1.552358 |
| 5 | CCACGAC | F | 1296 | 46XX | 46XX | 36 | 129 | 36 | 0.140539 | 1010.048 | 1004.468 | 0.501385 | 0.498615 | 0.413907 | -0.41391 |
| 6 | TCCTCGT | F | 2110 | 46XX | 46XX | 33 | 136 | 24 | 0.049392 | 994.7681 | 1000.632 | 0.498531 | 0.501469 | -1.45169 | 1.451689 |
| 7 | CCTTGCT | F | 2772 | 46XX | 46XX | 43 | 111 | 42 | 0.095395 | 997.3443 | 986.4745 | 0.50274 | 0.49726 | 1.299353 | -1.29935 |
| 8 | TCACTCT | M | 2506 | 46XX | 46XY | 34 | 126 | 32 | 0.158725 | 1004.807 | 996.2886 | 0.502128 | 0.497872 | 0.899842 | -0.89984 |
| 9 | CATCTTC | M | 3996 | 46XX | 46XY | 36 | 121 | 34 | 0.110817 | 1005.714 | 1002.283 | 0.500854 | 0.499146 | 0.067201 | -0.0672 |
| 10 | TTCGCCG | F | 4032 | 46XX | 46XX | 42 | 84 | 29 | 0.159776 | 999.7097 | 1000.399 | 0.499828 | 0.500172 | -0.60393 | 0.60393 |
| 11 | GTGTCCC | F | 4212 | 46XX | 46XX | 36 | 175 | 39 | 0.119147 | 1004.796 | 995.1465 | 0.502412 | 0.497588 | 1.085457 | -1.08546 |
| 12 | GCCCTTG | F | 3816 | 46XX | 46XX | 36 | 111 | 27 | 0.085664 | 1002.909 | 999.3516 | 0.500888 | 0.499112 | 0.089291 | -0.08929 |
| 13 | CTTACAC | F | 2160 | 46XX | 46XX | 41 | 123 | 40 | 0.117371 | 1002.012 | 995.0877 | 0.501734 | 0.498266 | 0.641893 | -0.64189 |
| 14 | TCGCAGC | F | 2790 | 46XX | 46XX | 51 | 125 | 36 | 0.119314 | 1008.515 | 999.3439 | 0.502284 | 0.497716 | 1.001374 | -1.00137 |
| 15 | CGGCCAT | F | 2783 | 46XX | 46XX | 51 | 125 | 50 | 0.123598 | 1005.525 | 998.867 | 0.501661 | 0.498339 | 0.594272 | -0.59427 |
| 16 | CCAGCTG | M | 2272 | 46XX | 46XY | 34 | 110 | 40 | 0.119257 | 1010.173 | 1004.256 | 0.501468 | 0.498532 | 0.468561 | -0.46856 |
| 17 | AGCACCT | M | 2401 | 46XX | 46XY | 34 | 140 | 43 | 0.111573 | 988.7338 | 986.5967 | 0.500541 | 0.499459 | -0.13768 | 0.137679 |
| 18 | CGATACC | F | 3960 | 46XX | 46XX | 41 | 126 | 27 | 0.099872 | 996.8338 | 999.2182 | 0.499403 | 0.500597 | -0.88162 | 0.88162 |
| 19 | CCCGAAT | M | 3816 | 46XX | 46XY | 37 | 133 | 30 | 0.095735 | 999.3982 | 991.0248 | 0.502103 | 0.497897 | 0.883556 | -0.88356 |
| 20 | CCCAGGG | M | 3474 | 46XX | 46XY | 38 | 123 | 32 | 0.115184 | 1006.395 | 992.8395 | 0.50339 | 0.49661 | 1.724514 | -1.72451 |
| 21 | CAGCACG | M | 1080 | 46XX | 46XY | 38 | 97 | 28 | 0.13036 | 994.7498 | 1003.364 | 0.497844 | 0.502156 | -1.90014 | 1.900139 |

FIG. 7

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 22 | CTCTATG | M | 2002 | 46XX | 46XY | 30 | 123 | 30 | 0.08322 | 994.7936 | 999.994 | 0.498697 | 0.501303 | -1.3432 | 1.343199 |
| 23 | ACTTTTAC | M | 3042 | 46XX | 46XY | 35 | 130 | 33 | 0.138751 | 1004.97 | 1003.101 | 0.500465 | 0.499535 | -0.18713 | 0.187128 |
| 24 | CGTATCG | F | 1922 | 46XX | 46XX | 23 | 159 | 29 | 0.254234 | 1003.218 | 1006.4 | 0.499208 | 0.500792 | -1.00868 | 1.008678 |
| 25 | AACCATT | M | 3708 | 46XX | 46XY | 38 | 148 | 31 | 0.145101 | 996.0673 | 995.7268 | 0.500085 | 0.499915 | -0.43538 | 0.435383 |
| 26 | CTGGGGC | M | 4032 | 46XX | 46XY | 30 | 126 | 27 | 0.077438 | 1005.191 | 1003.628 | 0.500389 | 0.499611 | -0.23694 | 0.23694 |
| 27 | TGCCGAG | F | 2383 | 46XX | 46XX | 35 | 138 | 32 | 0.131712 | 996.445 | 1002.698 | 0.498436 | 0.501564 | -1.51345 | 1.513451 |
| 28 | ATACCAG | F | 4104 | 46XX | 46XX | 23 | 99 | 33 | 0.099894 | 991.6721 | 1001.903 | 0.497434 | 0.502566 | -2.16839 | 2.168385 |
| 29 | GAAACCG | F | 2437 | 46XX | 46XX | 33 | 149 | 25 | 0.067606 | 1004.187 | 1006.778 | 0.499356 | 0.500644 | -0.91231 | 0.912305 |
| 30 | AAAGGCC | F | 2765 | 46XX | 46XX | 23 | 126 | 29 | 0.144098 | 1001.308 | 995.2881 | 0.498492 | 0.499636 | 0.494093 | -0.49409 |
| 31 | TCTAATT | M | 2416 | 46XX | 46XY | 23 | 119 | 28 | 0.105371 | 1006.535 | 1005.069 | 0.500364 | 0.499636 | -0.25309 | 0.25309 |
| 32 | GTTGATC | M | 2653 | 46XX | 46XY | 34 | 148 | 29 | 0.164518 | 1003.738 | 998.0583 | 0.501419 | 0.498581 | 0.435957 | -0.43596 |
| 33 | GATGTCT | M | 7488 | 46XX | 46XY | 36 | 148 | 21 | 0.056835 | 1012.154 | 1002.257 | 0.502456 | 0.497544 | 1.114241 | -1.11424 |
| 34 | AGTCTGT | M | 2653 | 46XX | 46XY | 26 | 140 | 39 | 0.21197 | 1004.959 | 996.9646 | 0.501997 | 0.498003 | 0.813799 | -0.8138 |
| 35 | AATTCTG | F | 3780 | 46XX | 46XX | 35 | 133 | 43 | 0.259642 | 997.0006 | 997.6736 | 0.499831 | 0.500169 | -0.60149 | 0.601493 |
| 36 | CTAAGTT | M | 8136 | 46XX | 46XY | 26 | 151 | 33 | 0.082773 | 1007.02 | 1006.742 | 0.500069 | 0.499931 | -0.44599 | 0.445992 |
| 37 | GGCGGTT | M | 2228 | 46XX | 46XY | 37 | 114 | 37 | 0.15551 | 1004.912 | 1003.615 | 0.500323 | 0.499677 | -0.28021 | 0.280209 |
| 38 | TATAGGC | F | 4248 | 46XX | 46XX | 27 | 165 | 48 | 0.064569 | 1014.599 | 995.8518 | 0.504662 | 0.495338 | 2.556064 | -2.55606 |
| 39 | TAGGTAC | M | 3960 | 46XX | 46XY | 35 | 124 | 41 | 0.167184 | 997.8251 | 998.4044 | 0.499855 | 0.500145 | -0.58608 | 0.586081 |
| 40 | CAATTGG | F | 4140 | 46XX | 46XX | 24 | 127 | 43 | 0.129398 | 997.6805 | 996.6003 | 0.500271 | 0.499729 | -0.31423 | 0.314232 |
| 41 | TCATAAG | M | 4320 | 46XX | 46XY | 39 | 139 | 29 | 0.227198 | 1002.31 | 991.6654 | 0.502669 | 0.497331 | 1.253298 | -1.2533 |
| 42 | GAACGGT | F | 3744 | 46XX | 46XX | 38 | 118 | 39 | 0.094147 | 1007.442 | 994.0998 | 0.503333 | 0.496667 | 1.687191 | -1.68719 |

FIG. 7 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 43 | AAGGCGT | F | 6984 | 46XX | 46XX | 37 | 130 | 36 | 0.228387 | 998.8644 | 995.701 | 0.500793 | 0.499207 | 0.027059 | -0.02706 |
| 44 | AGGAATC | F | 5112 | 46XX | 46XX | 18 | 188 | 39 | 0.244261 | 1001.465 | 995.804 | 0.501417 | 0.498583 | 0.435058 | -0.43506 |
| 45 | AACATAG | F | 3503 | 46XX | 46XX | 41 | 141 | 22 | 0.106969 | 999.5094 | 990.8389 | 0.502178 | 0.497822 | 0.932375 | -0.93238 |
| 46 | TTTTGGAT | F | 2606 | 46XX | 46XX | 39 | 143 | 32 | 0.196098 | 1001.959 | 1000.069 | 0.500472 | 0.499528 | -0.18279 | 0.182795 |
| 47 | TTTGATGT | F | 5292 | 46XX | 46XX | 36 | 111 | 30 | 0.109084 | 1004.708 | 1002.777 | 0.500481 | 0.499519 | -0.17694 | 0.176939 |
| 48 | ATGGTTG | M | 5184 | 46XX | 46XY | 24 | 160 | 40 | 0.060517 | 1010.204 | 1006.291 | 0.50097 | 0.49903 | 0.143003 | -0.143 |
| 49 | GGGTAGT | M | 3996 | 46XX | 46XY | 23 | 153 | 30 | 0.151707 | 1003.952 | 998.371 | 0.501394 | 0.498606 | 0.419553 | -0.41955 |
| 50 | AGATGAT | F | 5256 | 46XX | 46XX | 26 | 118 | 26 | 0.126345 | 998.1654 | 996.1826 | 0.500497 | 0.499503 | -0.16635 | 0.166347 |
| 51 | GTGAAAG | M | 4068 | 46XX | 46XY | 33 | 140 | 29 | 0.214532 | 1004.428 | 996.9586 | 0.501866 | 0.498134 | 0.728436 | -0.72844 |
| 52 | AGTGAAG | M | 11412 | 46XX | 46XY | 18 | 196 | 24 | 0.140258 | 1007.84 | 998.7992 | 0.502253 | 0.497747 | 0.9811 | -0.9811 |
| 53 | ACAACGC | M | 3146 | 46XX | 46XY | 21 | 147 | 32 | 0.180869 | 1010.525 | 999.8358 | 0.502659 | 0.497341 | 1.24639 | -1.24639 |
| 54 | GACGAGG | F | 5508 | 46XX | 46XX | 35 | 114 | 32 | 0.053622 | 994.8149 | 1005.452 | 0.497341 | 0.502659 | -2.22916 | 2.229159 |
| 55 | GGAATAC | F | 6624 | 46XX | 46XX | 28 | 140 | 37 | 0.21238 | 999.71187 | 1006.639 | 0.498275 | 0.501725 | -1.61846 | 1.618464 |
| 56 | GTTCGCG | M | 6192 | 46XX | 46XY | 44 | 115 | 25 | 0.083131 | 1009.487 | 999.2224 | 0.502555 | 0.497445 | 1.178758 | -1.17876 |
| 57 | GTCTTAT | F | 7056 | 46XX | 46XX | 25 | 115 | 37 | 0.135201 | 1005.611 | 996.4 | 0.5023 | 0.4977 | 1.01226 | -1.01226 |
| 58 | TAGTGTT | F | 5148 | 46XX | 46XX | 22 | 99 | 38 | 0.124127 | 996.363 | 999.6895 | 0.499167 | 0.500833 | -1.03587 | 1.035871 |
| 59 | TGCTTTC | M | 4104 | 46XX | 46XY | 30 | 197 | 28 | 0.310846 | 1004.509 | 1009.571 | 0.498743 | 0.501257 | -1.31256 | 1.312564 |
| 60 | TCTGTGG | M | 5364 | 46XX | 46XY | 27 | 122 | 26 | 0.118328 | 997.1746 | 992.0824 | 0.50128 | 0.49872 | 0.345307 | -0.34531 |
| 61 | TGGGCTC | F | 3636 | 46XX | 46XX | 28 | 178 | 30 | 0.158146 | 989.5388 | 999.8624 | 0.497405 | 0.502595 | -2.18709 | 2.187092 |
| 62 | TGAGTAT | M | 17856 | 46XX | 46XY | NA | NA | 45 | 0.064088 | 993.71189 | 996.5081 | 0.499299 | 0.500701 | -0.94924 | 0.949237 |
| 63 | TGCAAAT | F | 5004 | 46XX | 46XX | 35 | 109 | 39 | 0.076783 | 1003.939 | 992.7595 | 0.5028 | 0.4972 | 1.33858 | -1.33858 |

FIG. 7 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 64 | TATCAAT | M | 8712 | 46XX | 46XY | 35 | 119 | 33 | 0.077373 | 1004.37 | 996.8203 | 0.501886 | 0.498114 | 0.741595 | -0.74159 |
| 65 | TAAGAGT | F | 2552 | 46XX | 46XX+13 | 35 | 90 | 41 | 0.144442 | 999.7136 | 988.3962 | 0.502846 | 0.497154 | 1.369064 | -1.36906 |
| 66 | TAAAGAT | F | 7668 | 46XX | 46XX+13 | 30 | 141 | 37 | 0.057703 | 998.6741 | 990.8426 | 0.501968 | 0.498032 | 0.795151 | -0.79515 |
| 67 | TCTGCAC | M | 3996 | 46XX | 46XY+13 | 35 | 161 | 26 | 0.21564 | 1001.317 | 998.1811 | 0.500784 | 0.499216 | 0.021337 | -0.02134 |
| 68 | GTGGGCT | F | 7560 | 46XX | 46XX+21 | 35 | 125 | 28 | 0.092562 | 983.1548 | 1024.755 | 0.489641 | 0.510359 | -7.2619 | 7.2619 |
| 69 | GTGACTT | F | 13248 | 46XX | 46XX+21 | 19 | 132 | 30 | 0.085949 | 980.027 | 1020.997 | 0.489763 | 0.510237 | -7.18225 | 7.182254 |
| 70 | GGTCAGC | F | 7452 | 46XX | 46XX+21 | 40 | 91 | 31 | 0.056151 | 990.5328 | 1011.076 | 0.494868 | 0.505132 | -3.84532 | 3.845324 |
| 71 | GGGCGAC | M | 5508 | 46XX | 46XY+21 | 18 | 166 | 32 | 0.140102 | 965.1286 | 1037.339 | 0.48197 | 0.51803 | -12.2758 | 12.27579 |
| 73 | GGCTAAC | M | 5184 | 46XX | 46XY+18 | 29 | 147 | 29 | 0.157072 | 1044.147 | 960.7049 | 0.52081 | 0.47919 | 13.11012 | -13.1101 |
| 75 | GAGTGCG | F | 2689 | 46XX | 46XX+18 | 40 | 93 | 24 | 0.129256 | 1038.787 | 958.3378 | 0.520141 | 0.479859 | 12.67306 | -12.6731 |
| 76 | GAATGAC | F | 7632 | 46XX | 46XX+18 | 43 | 133 | 24 | 0.048391 | 1015.894 | 982.9916 | 0.50823 | 0.49177 | 4.887983 | -4.88798 |
| 78 | GCTTGTG | F | 7128 | 46XX | 46XX+18 | 25 | 128 | 30 | 0.06035 | 1018.978 | 985.6703 | 0.508308 | 0.491692 | 4.938613 | -4.93861 |
| 79 | GCAGAAC | M | 4464 | 46XX | 46XY+18 | 40 | 82 | 31 | 0.082749 | 1022.638 | 974.749 | 0.511988 | 0.488012 | 7.344068 | -7.34407 |
| 80 | ATGGAAT | F | 2100 | 46XX | 46XX+18 | 42 | 98 | 39 | 0.094043 | 1023.162 | 977.342 | 0.511452 | 0.488548 | 6.993832 | -6.99383 |
| 81 | ATCAGAT | M | 4176 | 46XX | 46XY+21 | 35 | 147 | 33 | 0.148476 | 957.3759 | 1038.729 | 0.479622 | 0.520378 | -13.8102 | 13.81016 |
| 82 | AGTTACT | M | 4500 | 46XX | 46XY+21 | 39 | 124 | 19 | 0.205496 | 952.9748 | 1049.25 | 0.475958 | 0.524042 | -16.205 | 16.20502 |
| 83 | AGTAGAC | M | 8640 | 46XX | 46XY+21 | 37 | 125 | 30 | 0.130907 | 973.3572 | 1028.835 | 0.486146 | 0.513854 | -9.54628 | 9.546281 |
| 84 | AGGTCTT | M | 16092 | 46XX | 46XY+21 | 43 | 94 | 35 | 0.126545 | 976.6225 | 1029.797 | 0.486749 | 0.513251 | -9.1521 | 9.152097 |
| 85 | AGGATAT | M | 4212 | 46XX | 46XY+21 | 40 | 157 | 24 | 0.119821 | 969.1251 | 1025.932 | 0.485763 | 0.514237 | -9.79643 | 9.796425 |
| 86 | AGGACGG | M | 4644 | 46XX | 46XY+21 | 33 | 97 | 31 | 0.053737 | 992.2248 | 1011.59 | 0.495168 | 0.504832 | -3.64941 | 3.649405 |
| 87 | AGAGATT | M | 4320 | 46XX | 46XY+21 | 31 | 119 | 37 | 0.08022 | 978.7159 | 1014.132 | 0.491114 | 0.508886 | -6.29894 | 6.298937 |

FIG. 7 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 89 | AGCTGCC | F | 6768 | 46XX | 46XX+21 | 31 | 98 | 35 | 0.126696 | 963.2256 | 1024.818 | 0.484509 | 0.515491 | -10.616 | 10.61595 |
| 90 | AGCGCTG | M | 1375 | 46XX | 46XY+21 | 36 | 162 | 36 | 0.133202 | 961.1764 | 1032.034 | 0.482225 | 0.517775 | -12.1088 | 12.10879 |
| 91 | AGCATGC | M | 5155 | 46XX | 46XY+21 | 41 | 154 | 37 | 0.095349 | 967.2823 | 1017.613 | 0.487322 | 0.512678 | -8.77777 | 8.777767 |
| 92 | AATGGTT | F | 2549 | 46XX | 46XX+21 | 41 | 119 | 32 | 0.09505 | 965.3134 | 1025.717 | 0.484831 | 0.515169 | -10.4056 | 10.4056 |
| 93 | AAGTAAG | F | 9216 | 46XX | 46XX+21 | 42 | 253 | 32 | 0.209915 | 946.0902 | 1052.948 | 0.473273 | 0.526727 | -17.96 | 17.96002 |
| 94 | AAATAGC | F | 2041 | 46XX | 46XX+21 | 36 | 161 | 32 | 0.102554 | 973.7957 | 1025.545 | 0.487058 | 0.512942 | -8.94982 | 8.949816 |
| 95 | AAATCCT | M | 1843 | 46XX | 46XY+21 | 42 | 91 | 35 | 0.137238 | 965.4467 | 1031.552 | 0.483449 | 0.516551 | -11.309 | 11.30904 |

FIG. 7 (cont.)

ASSAY SYSTEMS FOR GENETIC ANALYSIS

CROSS-REFERENCE TO RELATED APPLICATIONS

The present application is a continuation of U.S. patent application Ser. No. 13/205,570, filed on Aug. 8, 2011, which is a continuation-in-part of U.S. patent application Ser. No. 13/013,732, filed on Jan. 25, 2011, which claims priority to U.S. Provisional Patent Application No. 61/371,605, filed Aug. 6, 2010, the disclosures of each of which are incorporated by reference herein in their entireties.

FIELD OF THE INVENTION

This invention relates to the detection and quantification of genetic abnormalities in samples from pregnant females.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including syndromes caused by chromosomal aneuploidy (e.g., Down syndrome) and those caused by germline mutations resulting in either monogenic or polygenic diseases or disorders. Diagnostic methods for determining genetic anomalies have become standard techniques for identifying specific syndromes, diseases and disorders. In particular, prenatal diagnostics have become standard practice in high-risk populations to determine the presence or absence of certain disorders. Detection of both gross chromosomal abnormalities, such as trisomies, translocations and large insertions or deletions, and single gene traits, such as single gene mutations or polymorphisms associated with Rh blood group status, autosomal dominant or X-linked disorders, or autosomal recessive disorders are useful in detecting actual and potential pathologies and disorders that may affect a fetus. For example, chromosomal abnormalities such as trisomies 13, 18, and 21, the Robertsonian translocation associated with certain forms of Down syndrome, and larger deletions such as those found on chromosome 22 in DiGeorge syndrome all impact significantly on fetal health.

Similarly, detection of single gene disorders in a fetus, e.g., mutations in genes causing Tay-Sachs disease, sickle cell anemia, and thalassemia or copy number variants in diseases such as spinal muscular atrophy (SMA), may help parents to make important decisions regarding the health and care of the child. In addition, genetic status associated with blood group system status provide important information for maternal and/or and fetal health, and in many instances such knowledge provides an opportunity for intervention to prevent any deleterious outcomes in the pregnancy or immediately following birth.

Although conventional technology provides detection methods for these different genetic abnormalities, it currently requires different techniques to interrogate different classes of mutations. Conventional methods of prenatal diagnostic testing for chromosomal aneuploidy currently requires removal of a sample of fetal cells directly from the uterus for genetic analysis, using either chorionic villus sampling (CVS) between 11 and 14 weeks gestation or amniocentesis after 15 weeks. However, these invasive procedures carry a risk of miscarriage of around one percent (see Mujezinovic and Alfirevic, Obstet. Gynecol 2007; 110: 687-694. Current analysis of fetal cells typically involve karyotyping or fluorescent in situ hybridization (FISH) and do not provide information about single gene traits, and thus additional tests are required for identification of single gene diseases and disorders. Thus, a mother desiring genetic information on the status of a fetus must undergo multiple tests to test for various genetic abnormalities.

An assay providing quantification of non-polymorphic factors such as genetic copy number variations with simultaneous identification of genetic polymorphisms or mutations in a maternal sample would be a powerful tool to identity, e.g., potential medical complications in a mother and her fetus. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides assay systems and related methods for detection of a copy number variation (CNV) and determination of status of one or more single genes in a mother and/or fetus. More particularly, the present invention provides assay systems and related methods for determining copy number variation of one or more loci and detection of polymorphisms in one or more loci in maternal samples comprising genomic material (e.g., cell free DNA) from both maternal and fetal cell free nucleic acids. The present invention utilizes a single assay system that allows the identification of both genetic copy number variations (CNVs) and single gene polymorphisms, and the ability to distinguish between fetal and maternal CNVs and polymorphisms in the maternal sample. Tin a specific aspect this allows a determination of the fetal status of both copy number variations (including chromosomal abnormalities such as aneuploidies, translocations, insertions or deletions) and polymorphisms, e.g., mutations associated with either dominant or recessive diseases and/or predispositions.

In one aspect, the assay system utilizes amplification and detection of selected loci in a maternal sample to identify the presence or absence of a chromosomal aneuploidy and to determine status of selected genes associated with monogenic or polygenic traits.

In one specific aspect, the invention provides assay systems that comprise a single assay system with the ability to determine 1) presence or absence of one or more CNV in the maternal sample; and 2) polymorphisms associated with monogenic or polygenic traits. The assay systems can specifically detect copy number of selected loci and polymorphisms present in selected loci from a fetal source within the maternal sample, and to distinguish this from the copy number and polymorphisms present in selected loci from the maternal source in the maternal sample. Thus, in some preferred aspects, the CNV and polymorphisms are determined for fetal DNA within the maternal sample. Preferably, the loci are analyzed through use of cell free nucleic acids, and preferably the cell free nucleic acids analyzed in the assay system are cell free DNA (cfDNA).

In another preferred aspect, the CNV and/or polymorphisms are determined for maternal and fetal DNA within the maternal sample the invention provides assay systems that comprise a single assay system with the ability to determine 1) presence or absence of one or more CNV in the maternal sample; and 2) fetal polymorphisms associated with monogenic or polygenic traits; and 3) maternal status for polymorphisms associated with associated with monogenic or polygenic traits.

In one aspect, the invention provides an assay system for detection of the presence or absence of a copy number variation (CNV) of a genomic region and presence or absence of one or more fetal polymorphisms in a maternal sample using a single assay, the assay comprising the steps of introducing a first set of fixed sequence oligonucleotides to a maternal sample under conditions that allow the fixed oligonucleotides to specifically hybridize to complementary regions on one or more loci in or associated with a genomic region; introducing a second set of fixed sequence oligonucleotides comprising universal primer regions to the maternal sample under conditions that allow the fixed sequence oligonucleotides to specifically hybridize to complementary regions on one or more loci with a putative polymorphism; ligating the hybridized oligonucleotides to create contiguous ligation products complementary to the loci corresponding to a genomic region and/or the loci with a putative polymorphism; amplifying the contiguous ligation products to create amplification products; and detecting the amplification products. The detection of the amplification products correlates to the copy number of one or more genomic regions and the presence or absence of a polymorphism in one or more fetal loci in the maternal sample. Preferably, the CNV is determined for one or more fetal loci.

In certain aspects, the fixed oligonucleotides hybridize to adjacent regions in the loci, and the fixed oligonucleotides are directly ligated during the ligation step of the assay. In other aspects, the fixed oligonucleotides hybridize to non-adjacent regions in the loci that are separated by one, a few, or several nucleotides, and the region between the fixed oligonucleotides is used as a template for primer extension to close the gap between the fixed oligonucleotides prior to the ligation step.

Thus, in a second aspect, the invention provides an assay system for detection of the presence or absence of copy number variation (CNV) of a genomic region and presence or absence of one or more fetal polymorphisms in a maternal sample using a single assay, the assay comprising the steps of: introducing a first set of fixed sequence oligonucleotides to a maternal sample under conditions that allow the fixed oligonucleotides to specifically hybridize to complementary regions on one or more loci in or associated with a genomic region; introducing a second set of fixed sequence oligonucleotides to the maternal sample under conditions that allow the fixed sequence oligonucleotides to specifically hybridize to complementary regions on one or more loci with a putative polymorphism; extending the region between the first and second hybridized oligonucleotide of at least one fixed sequence oligonucleotide set with a polymerase and dNTPs to create two adjacently hybridized fixed sequence oligonucleotides from that set; ligating the hybridized oligonucleotides to create contiguous ligation products complementary to the loci corresponding to a genomic region and/or the loci with a putative polymorphism; amplifying the contiguous ligation products using the universal primer regions to create amplification products; and detecting the amplification products. The detection of the amplification products correlates to the copy number of one or more genomic region and the presence or absence of a fetal polymorphism in one or more loci in the maternal sample.

The fixed sequence oligonucleotides used to interrogate the specific loci comprise universal primer regions that are common to substantially all of the fixed sequence oligonucleotides used in a particular assay. This allows substantially all of the ligation products produced in a single assay to be amplified, isolated and/or analyzed using similar mechanisms (e.g., sequence determination or hybridization). Use of such universal primer regions obviates the need for individually distinguishable detectable moieties associated with particular loci or alleles, and provides a more efficient and cost-effective mechanisms for multiplexing interrogation and/or analysis of multiple loci from one or multiple samples. In a preferred aspect, the universal primer regions are used in sequence determination of the amplification products. In another preferred aspect, the same universal primer regions are used in the fixed sequence oligonucleotides used for detection of genomic regions and the fixed sequence oligonucleotides used for detection of polymorphisms.

Each set of fixed sequence nucleic acids is designed to hybridize to at least two separate regions in a selected locus. In preferred aspects, two or more separate oligos are used in a set to hybridize to these regions to provide adjacent nucleic acids complementary to the selected loci. In some aspects, however, a set can comprise a single probe with two or more distinct non-adjacent regions that are complementary to the selected loci (e.g., padlock probes), as described in more detail herein. The sets of fixed sequence oligos can be provided in the assay sequentially or simultaneously in the assay.

The genomic region can be a single locus, or it may be a larger region, up to and including a chromosome. For determination of larger genomic regions, sets of loci may be used to determine the size and in certain aspects the boundaries of such genomic regions for which CNV has been detected.

In certain aspects, the amplification products of the assay are isolated prior to detection. Preferably, the amplification products are isolated as individual molecules prior to detection. These isolated amplification products can optionally be further amplified to create identical copies of all or a portion of the individual amplification products prior to detection, or further amplified to create identical copies of molecules complementary to all or a portion of the individual amplification products prior to detection.

The multiplexed assays of the invention allow the analysis of 5 or more, preferably 10 or more, preferably 16 or more, preferably 20 or more, preferably 30 or more, preferably 32 or more, preferably 40 or more, preferably 48 or more, preferably 50 or more, preferably 60 or more, preferably 70 or more, preferably 80 or more, preferably 90 or more, and more preferably 96 or more selected loci simultaneously. These selected loci lay be different loci from a single sample, or they may be loci from two or more individuals. In the latter case, at least one of the two fixed sequence oligonucleotides used for analysis of a selected locus may comprise a sample identifier (e.g., a "sample index") that will allow the locus to be associated with a particular sample. Alternatively, a sample index may be added during amplification of the ligation product by using a primer comprising the sample index.

Preferably, at least one locus interrogated for CNV in a maternal sample is different from all loci interrogated for polymorphisms in the maternal sample. In specific aspects, several loci interrogated for CNV in a maternal sample are different from the loci interrogated for polymorphisms in the maternal sample. In more specific aspects, the majority of loci interrogated for CNV in a maternal sample are different from the loci interrogated for polymorphisms in the maternal sample.

In some aspects of the invention, the fixed sequence oligonucleotides hybridize to adjacent regions on a locus, and ligation of these oligonucleotides results in a ligation product that joins the two fixed sequence oligonucleotides. In other aspects, the fixed sequence oligonucleotides hybridize to non-adjacent regions on a locus, and the regions between the fixed sequence oligonucleotides is extended using a polymerase and dNTPs. In preferred aspects, the fixed sequence oligonucleotides hybridize to non-adjacent regions on a locus, and one or more bridging oligonucleotides hybridize to the region between and adjacent to the set of fixed sequence oligonucleotides. In certain preferred aspects, the bridging oligonucleotides used can provide content information on polymorphisms in the loci as well as information on frequency of loci for CNV analysis.

In other preferred aspects, the interrogation of these loci utilizes universal amplification techniques that allow amplification of multiple loci in a single amplification reaction. The selected nucleic acids for detection of both the CNV and polymorphisms using the assay system of the invention can be amplified using universal amplification methods following the initial selective amplification from the maternal sample. The use of universal amplification allows multiple nucleic acids regions from a single or multiple samples to be amplified using a single or limited number of amplification primers, and is especially useful in amplifying multiple selected regions in a single reaction.

Thus, in a preferred aspect of the invention, sequences complementary to primers for use in universal amplification are introduced to the selected loci during or following selective amplification. Preferably such sequences are introduced to the ends of such selected nucleic acids, although they may be introduced in any location that allows identification of the amplification product from the universal amplification procedure.

In certain preferred aspects, one or both of the primers used comprise a sample index or other identifier. In a specific aspect, a sample index is included in one or more of the universal primers. The sample index is incorporated into the amplification products, and amplification products from different samples may then be combined. The sample index is preferably detected concurrently with the detection of the CNV or chromosomal abnormality and the detection of polymorphism such that the CNV and polymorphism may be properly assigned to the sample of origin.

Frequencies of selected loci can be determined for a genomic region of interest and compared to the frequencies of loci of one or more other genomic regions of interest and/or one or more reference genomic regions to detect potential CNVs based on loci frequencies in the maternal sample.

In the assay systems of the invention, the amplification products are optionally isolated prior to detection. When isolated, they are preferably isolated as individual molecules to assist in subsequent detection. Following isolation, the amplification products can be further amplified to create identical copies of all or a portion of the individual amplification products prior to detection. Alternatively, the isolated amplification products can be further amplified to create identical copies of molecules complementary to all or a portion of the individual amplification products prior to detection.

Various methods of detection of CNVs can be employed in conjunction with the detection of the polymorphisms in the assay systems of the invention. In one general aspect, the assay system employs a method for determination of a CNV in one or more loci in a maternal sample, comprising the steps of amplifying one or more selected nucleic acids from a first genomic region of interest in a maternal sample; amplifying one or more selected nucleic acids from a second locus of interest in the maternal sample, determining the relative frequency of the selected loci, comparing the relative frequency of the selected loci, and identifying the presence or absence of a CNV based on the compared relative frequencies of the selected nucleic acids from the first and second loci. Preferably, the assay method amplifies two or more selected loci from different genomic regions, although the loci may be located in the same general genomic region for confirmation of CNVs arising from chromosomal abnormalities rather than CNVs from a single locus.

In other aspects, the bridging oligos are degenerate oligos. In other aspects, the bridging oligos are provided as pools of oligos with random sequences that comprise substantially every combination for the particular size of the bridging oligo used with the fixed sequence oligonucleotides.

Although the aspects of the invention using bridging oligonucleotides are described primarily using a single bridging oligo, it is envisioned that multiple bridging oligos that hybridize to adjacent, complementary regions between fixed sequence oligonucleotides can be used in the described methods.

In one preferred aspect, the invention provides an assay system for detection of the presence or absence of copy number variation (CNV) of a genomic region and presence or absence of one or more polymorphisms in a maternal sample using a single assay, the assay comprising the steps of: introducing a first set of fixed sequence oligonucleotides comprising universal primer regions to a maternal sample under conditions that allow the fixed sequence oligonucleotides to specifically hybridize to complementary regions on one or more loci in or associated with a genomic region; introducing a second set of fixed sequence oligonucleotides comprising universal primer regions to the maternal sample under conditions that allow the fixed sequence oligonucleotides to specifically hybridize to complementary, non-adjacent regions on one or more loci with a putative polymorphism; introducing one or more bridging oligonucleotides under conditions that allow the bridging oligonucleotides to specifically hybridize to regions in the loci between the regions complementary to the fixed sequence oligonucleotides of the sets; ligating the hybridized oligonucleotides to create contiguous ligation products complementary to the loci corresponding to a genomic region and/or the loci with a putative polymorphism; amplifying the contiguous ligation products using the universal primer regions to create amplification products; and detecting the amplification products. The detection of the amplification products correlates to the copy number of one or more genomic region and the presence or absence of a polymorphism in one or more loci in the maternal sample. Preferably, the CNV is detected for one or more fetal loci.

In another specific aspect, the invention provides an assay system for detection of the presence or absence of CNV of a genomic region and presence or absence of one or more polymorphisms in a maternal sample using a single assay, the assay comprising the steps of: introducing a first set of fixed sequence oligonucleotides to a maternal sample under conditions that allow the fixed sequence oligonucleotides to specifically hybridize to complementary regions on one or more loci in or associated with a genomic region; introducing a second set of fixed sequence oligonucleotides to the maternal sample under conditions that allow the fixed sequence oligonucleotides to specifically hybridize to complementary regions on one or more loci with a putative polymorphism; introducing one or more bridging oligonucleotides under conditions that allow the bridging oligonucleotides to specifically hybridize to regions in the loci between the regions complementary to the fixed sequence oligonucleotides of the set; extending the region between at least one fixed sequence oligonucleotide and a bridging oligonucleotide with a polymerase and dNTPs to create adjacently hybridized fixed sequence oligonucleotides and bridging oligonucleotides; ligating the hybridized oligonucleotides to create contiguous ligation products complementary to the loci corresponding to a genomic region and/or the loci with a putative polymorphism; amplifying the contiguous ligation products using the universal primer regions to create amplification products; and detecting the amplification products. The detection of the amplification products correlates to the copy number of one or more genomic region and the presence or absence of a polymorphism in one or more loci in the maternal sample. Preferably, the CNV is detected for one or more fetal loci.

In preferred aspects of the aspects of the invention using bridging oligonucleotides, the first and second set of fixed sequence oligonucleotides are introduced prior to introduction of the bridging oligonucleotides. More preferably, the unhybridized fixed sequence oligonucleotides are removed prior to introduction of the bridging oligonucleotides. In some aspects, the bridging oligonucleotides are introduced simultaneously with the ligation mixture. In other aspects, the hybridization products of the fixed sequence oligonucleotides and the locus are isolated prior to introduction of the bridging oligonucleotides.

In a preferred aspect, the assay system provides highly multiplexed loci interrogation using one or more common bridging oligonucleotides that are complementary to regions in two or more interrogated loci. Thus, the number of bridging oligonucleotides used in the multiplexed assay system will be less than the number of loci interrogated in the assay. In certain specific aspects, the assay system uses a pool of bridging oligonucleotides that are each designed to be compatible with two or more loci interrogated using the assay system of the invention. In these aspects, the bridging oligonucleotides used in the multiplexed assay are preferably designed to have a $T_m$ in a range of ±5° C., more preferably in a range of ±2° C.

In certain aspects, the assay system multiplexes loci interrogation using one or more common bridging oligonucleotides that are complementary to regions in two or more interrogated loci. Thus, the number of bridging oligonucleotides used in the multiplexed assay system will be less than the number of loci interrogated in the assay. In certain specific aspects, the assay system uses a pool of bridging oligonucleotides that are each designed to be compatible with two or more loci interrogated using the assay system of the invention.

In certain aspects, the bridging oligonucleotides are between 2-45 nucleotides in length. In a specific aspect, the bridging oligonucleotides are between 3-9 nucleotides in length. In yet another specific aspect, the bridging oligonucleotides are between 10-30 nucleotides in length.

The loci interrogated for CNV can in some instances be indicative of a duplication of a larger genomic region, e.g., all or part of a chromosome. Preferably, the assay systems can distinguish the copy number of these loci between the maternal and fetal sources within a maternal sample.

In such aspects, the invention provides assay systems that comprise a single assay system with the ability to detect within a maternal sample from an individual 1) presence or absence of a chromosomal abnormality associated with one or more CNV; and 2) presence or absence of one or more polymorphisms at one or more selected locus. The presence or absence of the chromosomal abnormality is preferably detected through the use of informative loci that allow the assay system to distinguish between nucleic acids from a major source and a minor source.

Thus, in a specific aspect, the invention provides an assay system for detection of the presence or absence of a fetal chromosomal abnormality and the presence or absence of one or more fetal polymorphisms using a single assay, the assay comprising the steps of: introducing a first set of fixed sequence oligonucleotides comprising universal primer regions to a maternal sample under conditions that allow the fixed oligonucleotides to specifically hybridize to complementary regions on one or more loci with putative polymorphisms; introducing a second set of fixed sequence oligonucleotides comprising universal primer regions to the maternal sample under conditions that allow the fixed oligonucleotides to specifically hybridize to complementary regions on two or more loci from a first chromosome; introducing a third set of fixed sequence oligonucleotides comprising universal primer regions to the maternal sample under conditions that allow the fixed oligonucleotides to specifically hybridize to complementary regions on two or more loci from a second chromosome; introducing one or more bridging oligonucleotides under conditions that allow the bridging oligonucleotides to specifically hybridize to regions in the loci between the regions complementary to the fixed sequence oligonucleotides of the set; ligating the hybridized oligonucleotides to create contiguous ligation products complementary to the nucleic acids; amplifying the contiguous ligation products to create amplification products; and detecting the amplification products. The detection of the amplification products correlates to the presence or absence of a fetal chromosomal abnormality and the presence or absence of a fetal polymorphism in one or more loci in the maternal sample.

In another specific aspect, the invention provides an assay system for detection of the presence or absence of a fetal chromosomal abnormality and presence or absence of one or more polymorphisms in fetal loci in a maternal sample using a single assay, the assay comprising the steps of introducing a first set of fixed sequence oligonucleotides comprising universal primer regions to a maternal sample under conditions that allow the fixed sequence oligonucleotides to specifically hybridize to complementary regions on one or more loci with a putative polymorphism; introducing a second set of fixed sequence oligonucleotides comprising universal primer regions to the maternal sample under conditions that allow the fixed sequence oligonucleotides to specifically hybridize to complementary regions on two or more loci from a first chromosome; introducing a third set of fixed sequence oligonucleotides comprising universal primer regions to the maternal sample under conditions that allow the fixed sequence oligonucleotides to specifically hybridize to complementary regions on two or more loci from a second chromosome; introducing one or more bridging oligonucleotides under conditions that allow the bridging oligonucleotides to specifically hybridize to regions in the loci between the regions complementary to the fixed sequence oligonucleotides of the set; extending the region between the first and second hybridized oligonucleotide of at least one fixed sequence oligonucleotide set with a polymerase and dNTPs to create two adjacently hybridized fixed sequence oligonucleotides from that set; ligating the hybridized oligonucleotides to create contiguous ligation products complementary to the nucleic acids; amplifying the contiguous ligation products to create amplification products; and detecting the amplification products. The detection of the amplification products correlates to the presence or absence of a fetal chromosomal abnormality and the presence or absence of a polymorphism in one or more loci in the maternal sample.

In some instances, the chromosomal abnormality is associated with gene duplication or loci expansion on a chromosome of interest. In other instances, the chromosomal abnormality is associated with a translocation resulting in the presence of an extra portion of a chromosome in the genome. In yet other instances, the chromosomal abnormality is associated with aneuploidy of a chromosome of interest.

Thus, in one aspect, the invention provides an assay system for detection of the presence or absence of a chromosomal abnormality and the presence or absence of polymorphisms at one or more loci using a single assay, the assay comprising the steps of introducing a first set of fixed sequence oligonucleotides to a maternal sample under conditions that allow the fixed sequence oligonucleotides to specifically hybridize to complementary regions in two or more nucleic acids corresponding to informative loci on two or more chromosomes; introducing a second set of fixed sequence oligonucleotides to the maternal sample under conditions that allow the fixed oligonucleotides to specifically hybridize to adjacent, complementary regions in nucleic acids indicative of the genetic status of one or more loci associated with a monogenic or polygenic trait; ligating the hybridized oligonucleotides to create contiguous ligation products complementary to the nucleic acids; amplifying the contiguous ligation products to create amplification products; and detecting the amplification products. Detection of the amplification product correlates to the detection of the loci in the maternal sample, and can be used to determine the quantity of loci associated with the presence or absence of the chromosomal abnormality and the genetic status of one or more loci in the maternal sample. Detected levels of these nucleic acids can thus be used to determine the presence or absence of the chromosomal abnormality in the fetus and the status of gene associated with a monogenic or polygenic trait in the mother and/or the fetus.

In another aspect, the invention provides an assay system for detection of the presence or absence of a chromosomal abnormality and the genetic status of one or more loci in a maternal sample using a single assay, the assay comprising the steps of introducing a first set of fixed sequence oligonucleotides to a maternal sample under conditions that allow the fixed oligonucleotides to specifically hybridize to complementary regions in two or more nucleic acids corresponding to informative loci on two or more chromosomes; introducing a second set of fixed sequence oligonucleotides to the maternal sample under conditions that allow the fixed oligonucleotides to specifically hybridize to complementary regions in nucleic acids indicative of the genetic status of one or more loci associated with a monogenic or polygenic trait; introducing one or more bridging oligonucleotides under conditions that allow the fixed sequence oligonucleotides to specifically hybridize to complementary regions in the nucleic acids, wherein one or more bridging oligonucleotides are complementary to a region of the nucleic acids between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products; and detecting the amplification products. Detection of the amplification product correlates to the detection of the loci in the maternal sample, and can be used to determine the quantity of loci associated with the presence or absence of the chromosomal abnormality and the genetic status of one or more loci in the maternal sample. Detected levels of these nucleic acids can thus be used to determine the presence or absence of a fetal chromosomal abnormality (e.g., an aneuploidy) and the presence or absence of a polymorphism at one or more loci from a fetal source and/or the maternal source within a maternal sample.

In a specific aspect, the invention provides an assay system for detecting the presence or absence of a fetal aneuploidy and detecting the status of one or more genes of the blood group system in a maternal sample using a single assay, comprising the steps of introducing a first set of fixed sequence oligonucleotides to the maternal sample under conditions that allow the fixed oligonucleotides to specifically hybridize to complementary regions in two or more informative loci on two or more chromosomes; introducing a second set of fixed sequence oligonucleotides to the maternal sample under conditions that allow the fixed oligonucleotides to specifically hybridize to complementary regions in nucleic acids indicative of the genetic status of one or more genes associated with blood group status; introducing one or more bridging oligonucleotides under conditions that allow the fixed sequence oligonucleotides to specifically hybridize to complementary regions in the nucleic acids, wherein one or more bridging oligonucleotides are complementary to a region of the nucleic acids between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products having the sequence of the loci; and detecting the amplification products.

Detection of the amplification product provides detection of the loci associated with the presence or absence of an aneuploidy and the status of one or more genes of the blood group system in the maternal sample. Detected levels of these nucleic acids can be used to determine the presence or absence of an aneuploidy in the fetus and the status of one or more genes of the blood group system in the mother and/or the fetus.

In another aspect, the present invention utilizes techniques that allow the identification of both CNVs and infectious agents in a maternal sample. This may be especially helpful to monitor patients in which the clinical outcome may be compromised by the presence of an infectious agent. For example, pregnant women have changes in their immune system and thus may be more susceptible to infection with pathogens that may have an adverse effect on the mother and/or fetus. Accordingly, in specific aspects the invention provides an assay system for detection of the presence or absence of genetic copy number variation (CNV) of a genomic region and the presence or absence of an infectious agent in a maternal sample using a single assay, the assay comprising the steps of: introducing a first set of fixed sequence oligonucleotides to a maternal sample under conditions that allow the fixed oligonucleotides to specifically hybridize to complementary regions on one or more loci in or associated with a genomic region; introducing a second set of fixed sequence oligonucleotides to the maternal sample under conditions that allow the fixed oligonucleotides to specifically hybridize to complementary regions in nucleic acids indicative of an infectious agent; ligating the hybridized oligonucleotides to create a contiguous ligation product complementary to the nucleic acids; amplifying the contiguous ligation product to create amplification products; and detecting the amplification products. The detection of the amplification products correlates to copy number of the genomic region, the presence or absence of a polymorphism at one or more loci, and the presence or absence of an infectious agent in the maternal sample.

In another specific aspect, the invention provides an assay system for detection of the presence or absence of copy number variation (CNV) of a genomic region, the presence or absence of one or more polymorphisms, and the presence or absence of an infectious agent in a maternal sample from an individual using a single assay, the assay comprising the steps of: introducing a first set of fixed sequence oligonucleotides to a maternal sample under conditions that allow the fixed oligonucleotides to specifically hybridize to complementary regions on one or more loci in or associated with a genomic region; introducing a second set of fixed sequence oligonucleotides to the maternal sample under conditions that allow the fixed oligonucleotides to specifically hybridize to complementary regions on one or more loci with a putative polymorphism; introducing a third set of fixed sequence oligonucleotides to the maternal sample under conditions that allow the fixed oligonucleotides to specifically hybridize to complementary regions in nucleic acids indicative of an infectious agent; introducing one or more bridging oligonucleotides under conditions that allow the bridging oligonucleotides to specifically hybridize to complementary regions in the nucleic acids, wherein one or more bridging oligonucleotides are complementary to a region of the nucleic acids between the regions complementary to the fixed sequence oligonucleotides of the set; ligating the hybridized oligonucleotides to create a contiguous ligation product complementary to the nucleic acids; amplifying the contiguous ligation product to create amplification products; and detecting the amplification products. The detection of the amplification products correlates to copy number of the genomic region, the presence or absence of a polymorphism at one or more loci, and the presence or absence of an infectious agent in the maternal sample.

In preferred aspects, the assay systems for detection of infectious organisms further comprise introducing one or more bridging oligonucleotides under conditions that allow the bridging oligonucleotides to specifically hybridize to complementary regions in the nucleic acids, wherein the one or more bridging oligonucleotides are complementary to a region of the nucleic acids between the regions complementary to the fixed sequence oligonucleotides of each set.

Levels of selected loci can be determined for a genomic region of interest (e.g., a chromosome or a portion thereof) and compared to the quantities of loci of one or more other genomic regions of interest and/or one or more reference genomic regions to detect potential aneuploidies based on chromosome frequencies in the maternal sample.

In certain aspects, the fixed sequence oligonucleotides comprise universal primer regions that are used in amplification of the contiguous ligation product. In specific assay systems, the unhybridized fixed sequence oligonucleotides are removed prior to amplification of the contiguous ligation product.

In some specific aspects, the first and second fixed sequence oligonucleotides are introduced prior to introduction of the bridging oligonucleotides. In other specific aspects, the one or more bridged oligonucleotides are introduced to the assay simultaneously with the first and second fixed sequence oligonucleotides.

In certain aspects, the amplification products resulting from the fixed sequence oligonucleotides and the bridging oligonucleotides are optionally isolated following ligation and amplification but before detection. The amplification products are preferably isolated as individual molecules prior to detection. The isolated molecules can also be further amplified to create identical copies of all or a portion of the individual amplification products, or alternatively to create identical copies of molecules complementary to all or a portion of the individual amplification products prior to detection.

In a preferred aspect, the assay system of the invention employs fixed sequence oligonucleotides comprising one or more indices. The amplification product can be detected using detection of the indices rather than or in addition to detection of the amplified sequence itself. In specific aspects, the indices are allele-specific indices, i.e. associated with the presence of certain alleles, and detection of the index reflects a particular allele under interrogation. For example, allele-specific indices may correspond to the use of a bridging oligonucleotide complementary for a specific polymorphism or mutation in a locus.

Various methods of detection of the chromosomal abnormality can be employed in conjunction with the detection of the selected gene status in the assay systems of the invention. In one general aspect, the assay system employs a method for determination of a copy number variation in a genomic region of interest in a maternal sample, comprising the steps of enriching for one or more selected loci from a first genomic region of interest in a maternal sample; enriching for one or more selected loci from a second genomic region of interest in the maternal sample, determining the relative frequency of the selected regions from the first and second genomic regions of interest, comparing the relative frequency of the selected regions from the first and second genomic region of interest, and identifying the presence or absence of a copy number variation based on the compared relative frequencies of the selected regions. Preferably, the assay method enriches for two or more selected nucleic acids regions from the first and second genomic region of interest.

In another general aspect, the assay system employs a method for determining the presence or absence of a chromosomal abnormality associated with CNV in a genomic region, comprising the steps of amplifying one or more selected loci from a first chromosome of interest in a maternal sample; amplifying one or more selected loci from a second chromosome of interest in the maternal sample, determining the relative frequency of the selected regions from the first and second chromosomes of interest, comparing the relative frequency of the selected regions from the first and second chromosomes of interest, and identifying the presence or absence of an aneuploidy based on the compared relative frequencies of the selected regions.

In yet another general aspect, the assay system employs a method for determination of the presence or absence of an aneuploidy, comprising the steps of amplifying two or more selected loci in the cell free DNA corresponding to a first chromosome of interest in a maternal sample; amplifying two or more selected loci in the cell free DNA corresponding to a second chromosome of interest in the maternal sample, determining the relative frequency of the selected regions from the first and second chromosomes of interest, comparing the relative frequency of the selected regions from the first and second chromosomes of interest, and identifying the presence or absence of an aneuploidy based on the compared relative frequencies of the selected regions. In a specific aspect, the loci of the first and second chromosomes are amplified in a single reaction, and preferably in a single reaction contained within a single vessel.

The selected nucleic acids for detection of both the chromosomal abnormality and the status of the selected genes analyzed using the assay system of the invention can be amplified using universal amplification methods following the initial selective amplification from the maternal sample. or enrichment. Preferably, the assay system detects the presence or absence of loci in samples that can be easily obtained from a subject, such as blood, plasma, serum and the like. In one general aspect, the assay system utilizes detection of selected regions in cfDNA in a maternal sample. In one more specific aspect, the assay system utilizes detection of selected regions in cell free DNA in a maternal sample to identify the presence or absence of a chromosomal aneuploidy and the status of one or more loci. Detection of single gene status can be obtained using direct detection of specific mutations or polymorphisms in the selected locus corresponding to the gene. Aneuploidy in a genomic region of interest can be determined based on detection of quantities of selected loci and comparison to the quantities of selected loci from another genomic region of interest and/or to the quantities of selected loci from a reference genomic region of interest. In a particular aspect, the ratio of the frequencies of the nucleic acid are compared to a reference mean ratio that has been determined for a statistically significant population of genetically "normal" subjects, i.e. subjects that do not have the particular genetic anomaly that is being interrogated in a particular assay system.

In a preferred aspect of the invention, the amplification products corresponding to the selected nucleic acids are isolated as individual molecules for analysis of the selected loci. These individual amplification products are isolated from one another, and preferably physically isolated (e.g., on a substrate or in individual vessels). The individual molecules may be further amplified following isolation to make multiple, identical copies of the amplification product, a portion thereof, or a nucleic acid complementary to the amplification product or a portion thereof. The detection of the individual molecules or the amplification product may be done through sequencing.

In some aspects, the ligation product is not amplified, but rather is directly detected following hybridization, e.g., using single molecule sequencing techniques.

Thus, in a specific aspect, the invention provides an assay system for detection of the presence or absence of a chromosomal abnormality and the genetic status of one or more loci in a maternal sample using a single assay, the assay comprising the steps of: introducing a first set of fixed sequence oligonucleotides to a maternal sample under conditions that allow the fixed sequence oligonucleotides to specifically hybridize to complementary regions in two or more nucleic acids corresponding to a particular chromosome; introducing a second set of fixed sequence oligonucleotides to the maternal sample under conditions that allow the fixed sequence oligonucleotides to specifically hybridize to complementary regions in nucleic acids indicative of the genetic status of one or more loci associated with a monogenic or polygenic disease, disorder or predisposition; introducing one or more bridging oligonucleotides under conditions that allow the bridging oligonucleotides to specifically hybridize to complementary regions in the nucleic acids, wherein one or more bridging oligonucleotides are complementary to a region of the nucleic acids between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products having the sequence of the loci; isolating individual amplification products; and analyzing the individual amplification products to determine the sequence of all or part of the individual amplification products. The analysis of the individual amplification products correlates to the presence or absence of a chromosomal abnormality and the genetic status of one or more loci in the maternal sample. For example, the levels of the nucleic acids corresponding to a particular chromosome may be compared by also using nucleic acids corresponding to another chromosome, or they may be compared to reference levels for the chromosome being interrogated.

In a preferred aspect, the individual amplification products are analyzed through sequence determination. In other aspects, the individual amplification products are analyzed using hybridization techniques.

It is a feature of the present invention that copy number of the selected loci can be detected using non-polymorphic detection methods, i.e., detection methods that are not dependent upon the presence or absence of a particular polymorphism to identity the selected nucleic acid region. In a preferred aspect, the assay detection systems utilize non-polymorphic detection methods to "count" the relative numbers of selected loci present in a maternal sample. These numbers can be utilized to determine if, statistically, a maternal sample is likely to have a CNV in a genomic region of a maternal sample. Such information can be used to identify a particular pathology or genetic disorder, to confirm a diagnosis or recurrence of a disease or disorder, to determine the prognosis of a disease or disorder, to assist in determining potential treatment options, etc.

In some aspects, the methods for determination of copy number variation used by the assay system measure the relative frequencies of selected loci from different chromosomes in a sample. The levels of the different selected loci corresponding to specific chromosomes can be individually quantified and compared to determine the presence or absence of a chromosomal aneuploidy in a maternal sample. The individually quantified regions may undergo a normalization calculation or the data may be subjected to outlier exclusion prior to comparison to determine the presence or absence of an aneuploidy in a maternal sample.

In other aspects, the relative frequencies of the selected loci are used to determine a chromosome frequency of the first and second chromosomes of interest, and the presence or absence of an aneuploidy is based on the compared chromosome frequencies of the first and second chromosomes of interest.

In yet other aspects, the relative frequencies of the selected loci are used to determine a chromosome frequency of a chromosome of interest and a reference chromosome, and the presence or absence of an aneuploidy is based on the compared chromosome frequencies of the chromosome of interest and the reference chromosome.

As the assay system of the invention is preferably configured as a highly multiplexed system, multiple loci from a single or multiple chromosomes within an individual sample and/or multiple samples can be analyzed simultaneously. In such multiplexed systems, the samples can be analyzed separately, or they may be initially pooled into groups of two or more for analysis of larger numbers of samples. When pooled data is obtained, such data is preferably identified for the different samples prior to analysis of aneuploidy. In some aspects, however, the pooled data may be analyzed for potential CNVs, and individual samples from the group subsequently analyzed if initial results indicates that a potential aneuploidy is detected within the pooled group.

In certain aspects, the assay systems utilize one or more indices that provide information on specific samples. For example, an index can be used in selective or universal amplification that is indicative of a sample from which the nucleic acid was amplified.

In one particular aspect, the selected loci are isolated prior to detection. The selected loci can be isolated from the maternal sample using any means that selectively isolate the particular nucleic acids present in the maternal sample for analysis, e.g., hybridization, amplification or other form of sequence-based isolation of the nucleic acids from the maternal sample. Following isolation, the selected nucleic acids are individually distributed in a suitable detection format, e.g., on a microarray or in a flow cell, for determination of the sequence and/or relative quantities of each selected nucleic acid in the maternal sample. The relative quantities of the detected nucleic acids are indicative of the number of copies of chromosomes that correspond to the selected nucleic acids present in the maternal sample.

Following isolation and distribution of the selected nucleic acids in a suitable format, the selected sequences are identified, e.g., through sequence determination of the selected sequence.

In one specific aspect, the invention provides an assay system for detection of the presence or absence of a fetal aneuploidy, comprising the steps of providing a maternal sample comprising maternal and fetal cfDNA, amplifying two or more selected loci from a first and second chromosome of interest in the maternal sample, amplifying two or more selected loci from the first and second chromosome of interest in the maternal sample, determining the relative frequency of the selected regions from the chromosomes of interest, comparing the relative frequency of the selected loci from the first and second chromosomes of interest, and identifying the presence or absence of a fetal aneuploidy based on the compared relative frequencies of the selected loci.

In some specific aspects, the relative frequencies of the loci from a genomic region are individually calculated, and the relative frequencies of the individual loci are compared to determine the presence or absence of a chromosomal abnormality. In other specific aspects, the relative frequencies of the selected loci are used to determine a chromosome frequency of a first and second chromosome of interest and a reference chromosome, and the copy number variation for the chromosome or a genomic region of the chromosome is based on the compared chromosome frequencies of the first and second chromosomes of interest.

In another specific aspect, the invention provides an assay system for detection of the presence or absence of a fetal aneuploidy, comprising the steps of providing a maternal sample, amplifying two or more selected loci from a chromosome of interest in the maternal sample, amplifying two or more selected loci from a reference chromosome in the maternal sample, determining the relative frequency of the selected regions from the chromosomes of interest and the reference chromosome, comparing the relative frequency of the selected loci from the chromosomes of interest and the reference chromosome, and identifying the presence or absence of a fetal aneuploidy based on the compared relative frequencies of the selected loci. In some specific aspects, the relative frequencies of the loci are individually calculated, and the relative frequencies of the individual loci are compared to determine the presence or absence of a fetal aneuploidy. In other specific aspects, the relative frequencies of the loci are used to determine a chromosome frequency of the chromosome of interest and the reference chromosome, and the presence or absence of a fetal aneuploidy is based on the compared chromosome frequencies of the chromosome of interest and the reference chromosome.

The maternal sample used for analysis can be obtained or derived from any sample which contains the nucleic acid of interest to be analyzed using the assay system of the invention. For example, a maternal sample may be from any maternal fluid which comprises both maternal and fetal cell free nucleic acids, including but not limited to maternal plasma, maternal serum, or maternal blood. In certain aspects, however, the DNA of interest to be analyzed using the assay system of the invention comprises DNA from fetal cells. Such samples can be obtained from maternal sources such as amniotic fluid, placenta (e.g., the chorionic villi), and the like.

Although preferably the assay system is used to detect cfDNA in a maternal sample, in certain aspects the DNA of interest to be analyzed using the assay system of the invention comprises DNA directly from the different cell types rather than from a maternal sample containing DNA from the major and minor cell types. Such samples can be obtained from various sources depending upon the target DNA. For example, fetal cells for analysis can be derived from samples such as amniotic fluid, placenta (e.g., the chorionic villi), and the like. Samples of donor organs can be obtained in an individual by biopsy. Infectious organisms can be isolated directly from an individual and analyzed following isolation. DNA can be extracted from cancerous cells or tissues and used for analysis.

It is a feature of the invention that the nucleic acids analyzed in the assay system do not require polymorphic differences between the fetal and maternal sequences to determine potential CNVs. It is another feature of the invention that the substantial majority of the nucleic acids isolated from the maternal sample and detected in the assay system provide information relevant to the presence and quantity of a particular chromosome in the maternal sample, i.e. the detected selected nucleic acids are indicative of a particular locus associated with a chromosome. This ensures that the majority of nucleic acids analyzed in the assay system of the invention are informative.

In some aspects, multiple loci are determined for each genomic region under interrogation, and the quantity of the selected regions present in the maternal sample are individually summed to determine the relative frequency of a locus in a maternal sample. This includes determination of the frequency of the locus for the combined maternal and fetal DNA present in the maternal sample. Preferably, the determination does not require a distinction between the maternal and fetal DNA, although in certain aspects this information may be obtained in addition to the information of relative frequencies in the sample as a whole.

In preferred aspects, selected nucleic acids corresponding to regions from a chromosome are detected and summed to determine the relative frequency of a chromosome in the maternal sample. Frequencies that are higher than expected for a locus corresponding to one chromosome when compared to the quantity of a locus corresponding to another chromosome in the maternal sample are indicative of an aneuploidy. This can be a comparison of chromosomes that each may be a putative aneuploid in the fetus (e.g., chromosomes 18 and 21), where the likelihood of both being aneuploid is minimal. This can also be a comparison of chromosomes where one is putatively aneuploid (e.g., chromosome 21) and the other acts as a reference chromosome (e.g. an autosome). In yet other aspects, the comparison may utilize two or more chromosomes that are putatively aneuploid and one or more reference chromosomes.

In one aspect, the assay system of the invention analyzes multiple nucleic acids representing selected loci on chromosomes of interest, and the relative frequency of each selected locus from the sample is analyzed to determine a relative chromosome frequency for each particular chromosome of interest in the sample. The chromosomal frequency of two or more chromosomes or portions thereof is then compared to statistically determine whether a chromosomal abnormality exists.

In another aspect, the assay system of the invention analyzes multiple nucleic acids representing selected loci on chromosomes of interest, and the relative frequency of each selected nucleic acid from the sample is analyzed and independently quantified to determine a relative amount for each selected locus in the sample. The sum of the loci in the sample is compared to statistically determine whether a CNV exists in a maternal sample.

In another aspect, subsets of loci on each chromosome are analyzed to determine whether a chromosomal abnormality exists. The loci frequency can be summed for a particular chromosome, and the summations of the loci used to determine aneuploidy. This aspect of the invention sums the frequencies of the individual loci in each genomic region and then compares the sum of the loci on a genomic region of one chromosome against a genomic region of another chromosome to determine whether a chromosomal abnormality exists. The subsets of loci can be chosen randomly but with sufficient numbers of loci to yield a statistically significant result in determining whether a chromosomal abnormality exists. Multiple analyses of different subsets of loci can be performed within a maternal sample to yield more statistical power. In another aspect, particular loci can be selected that are known to have less variation between maternal samples, or by limiting the data used for determination of chromosomal frequency, e.g., by ignoring the data from loci with very high or very low frequency within a sample.

In a particular aspect, the measured quantities of one or more particular loci are normalized to account for differences in loci quantity in the sample. This can be done by normalizing for known variation from sources such as the assay system (e.g., temperature, reagent lot differences), underlying biology of the sample (e.g., nucleic acid content), operator differences, or any other variables.

In certain specific aspects, determining the relative percentage of fetal DNA in a maternal sample may be beneficial in performing the assay system, as it will provide important information on the relative statistical presence of loci that may be indicative of fetal aneuploidy. In each maternally-derived sample, the fetus will have approximately 50% of its loci inherited from the mother and 50% of the loci inherited from the father when no copy number variant is present for that locus. Determining the non-maternal loci can allow the estimation of fetal DNA in a maternal sample, and thus provide information used to calculate the statistically significant differences in chromosomal frequencies for chromosomes of interest. Such loci could thus provide two forms of information in the assay—allelic information can be used for determining the percent fetal DNA contribution in a maternal sample and a summation of the allelic information can be used to determine the relative overall frequency of that locus in a maternal sample. The allelic information is not needed to determine the relative overall frequency of that locus.

Thus, in some specific aspects, the relative fetal contribution of maternal DNA at the allele of interest can be compared to the non-maternal contribution at that allele to determine approximate fetal DNA concentration in the sample. In a particular aspect, the estimation of fetal DNA in a maternal sample is determined at those loci where the mother is homozygous at the locus for a given allele and a fetus is heterozygous at the allele. This may be due to the allele being inherited by the fetus from the father at that locus, or it may be due to a de novo polymorphism at that locus. In this situation, the fetal DNA amount will be approximately twice the amount of the fetal allele that is different from the mother. In other specific aspects, the relative quantity of solely paternally-derived sequences (e.g., Y-chromosome sequences or paternally-specific polymorphisms) can be used to determine the relative concentration of fetal DNA in a maternal sample.

In aspects utilizing autosomal loci, generally the percent fetal DNA contribution is determined by comparing one or more genetic variations on the one or more informative loci. In some particular aspects, these genetic variations are short tandem repeats. In other particular aspects, these genetic variations are one or more single nucleotide polymorphisms. In other aspects, the percent fetal DNA contribution in a maternal sample is calculated by detecting methylation differences between loci on fetal DNA and maternal DNA.

The amplified molecules in the assay samples are analyzed to determine a first number of assay samples which contain the selected nucleic acid and a second number of assay samples which contain a reference nucleic acid.

In a specific aspect, the assay system of the invention can be utilized to determine if a sample taken from a subject is a maternal sample containing fetal DNA, thus acting as a confirmatory test for pregnancy or as a quality control step before determining the presence or absence of aneuploidy.

In another specific aspect, the assay system of the invention can be utilized to determine if the maternal sample contains more than one fetal genome, thus permitting the detection of multiple fraternal fetuses, for example fraternal twins or triplets.

In another specific aspect, the assay system of the invention can be utilized to detect and quantify DNA contamination.

In another specific aspect, the assay system of the invention can be utilized to determine if one or more fetus in a multiples pregnancy is likely to have an aneuploidy and/or genetic mutation, and whether further confirmatory tests should be undertaken to confirm the identification of the fetus with the abnormality. For example, the assay system of the invention can be used to determine if one of two twins has a high likelihood of an aneuploidy or disease trait, followed by a more invasive technique that can distinguish physically between the fetuses, such as amniocentesis or chorionic villi sampling, to determine the identification of the affected fetus.

In another specific aspect, the assay system of the invention can be utilized to determine if a fetus has a potential mosaicism in a cell population, and whether further confirmatory tests should be undertaken to confirm the identification of mosaicism in the mother and/or fetus. In certain instances, determination of the percent fetal nucleic acids in a maternal sample could assist in quantification of the estimated level of mosaicism. Mosaicism could be subsequently confirmed using other testing methods that could distinguish mosaic full or partial aneuploidy in specific cells or tissue.

In another aspect, the oligonucleotides for a given selected nucleic acid can be connected at the non-sequence specific ends such that a circular or unimolecular probe may bind thereto. In this aspect, the 3' end and the 5' end of the circular probe binds to the selected locus and at least one universal amplification region is present in the non-selected specific sequence of the circular probe.

In certain aspects, the assay format allows the detection of a combination of abnormalities using different detection mechanisms applied to the maternal sample. For example, fetal aneuploidy can be determined through the identification of selected nucleic acids in a maternal sample, and specific mutations may be detected by sequence determination of mutations in one or more identified alleles of a known locus. Thus, in specific aspects, sequence determination of a selected nucleic acid can provide information on the number of copies of a particular locus in a maternal sample as well as the presence of a mutation in a fetal allele within the maternal sample.

In specific aspects, the assay system provides mechanisms for detecting chromosomal abnormalities, genetic status of one or more loci associated with a monogenic or polygenic trait, and the presence or absence of an infectious agent in a maternal sample using a single assay. Such assays are able to provide a comprehensive look at maternal and fetal health using a single assay system. This single assay comprises the steps of introducing a first set of fixed sequence oligonucleotides to a maternal sample under conditions that allow the fixed oligonucleotides to specifically hybridize to complementary regions in two or more nucleic acids corresponding to informative loci on two or more chromosomes; introducing a second set of fixed sequence oligonucleotides to the maternal sample under conditions that allow the fixed oligonucleotides to specifically hybridize to complementary regions on nucleic acids indicative of the genetic status of one or more loci associated with a monogenic or polygenic trait; introducing a third set of fixed sequence oligonucleotides to the maternal sample under conditions that allow the fixed oligonucleotides to specifically hybridize to complementary regions in nucleic acids indicative of an infectious agent; introducing one or more bridging oligonucleotides under conditions that allow the fixed sequence oligonucleotides to specifically hybridize to complementary regions in the nucleic acids, wherein one or more bridging oligonucleotides are complementary to a region of the nucleic acids between and immediately adjacent to the regions complementary to the fixed sequence oligonucleotides of each set; ligating the hybridized oligonucleotides to create a contiguous ligation product complementary to the nucleic acids; amplifying the contiguous ligation product to create amplification products; and detecting the amplification products. The detection of the amplification products correlates to the presence or absence of a chromosomal abnormality, the genetic status of one or more loci associated with a monogenic or polygenic trait and/or the presence or absence of an infectious agent in the maternal sample.

It is an important feature of the assay that the amplification products are analyzed directly without the need for enrichment of polymorphic regions from the initial maternal sample. Thus, the current invention allows detection of both CNV and polymorphisms from a maternal sample without an intervening polymorphic enrichment step prior to sequence determination of the selected loci.

It is another important feature of the assay that both CNV and polymorphism detection are determined using a targeted approach of selected amplification and detection. This allows the majority of information gathered in the assay to be useful for the determination of the CNV and/or polymorphism interrogated in the locus of interest, and obviates the need to generate sequence reads that must be aligned with a reference sequence.

These and other aspects, features and advantages will be provided m more detail as described herein.

BRIEF DESCRIPTION OF THE FIGURES

FIG. 7 is a summary of patient and sample information and data for a subset of a second cohort of pregnant subjects.

DEFINITIONS

Figure 1:
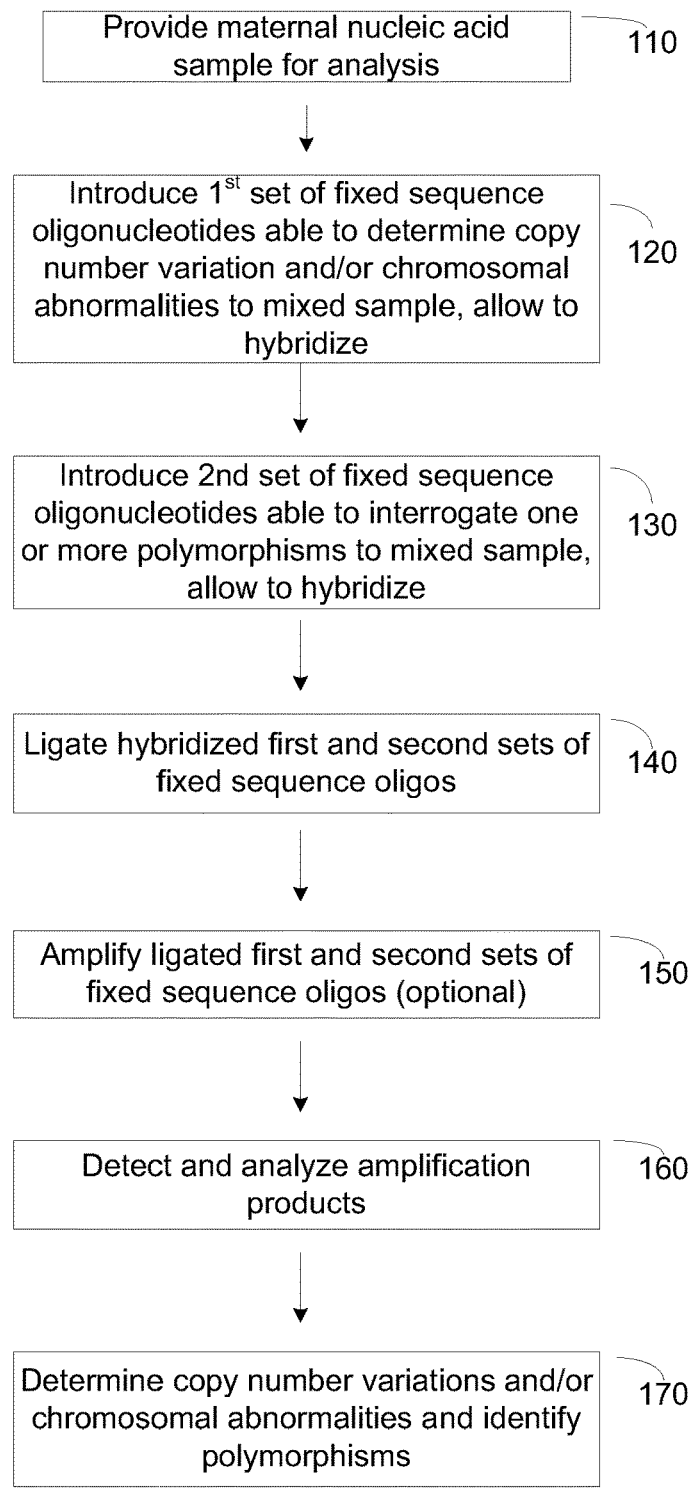
FIG. 1 is a simplified flow chart of the general steps utilized in the assay systems of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication method performed in vitro as compared to its starting amount in a maternal sample.

The term "amplification product" as used herein refers to the product resulting from an amplification reaction using the contiguous ligation product as a template, or the product resulting from an amplification reaction using a molecule complementary to the contiguous ligation product as a template.

The term "chromosomal abnormality" refers to any genetic variation that affects all or part of a chromosome larger than a single locus. The genetic variants may include but not be limited to any copy number variant such as duplications or deletions, translocations, inversions, and mutations. Examples of chromosomal abnormalities include, but are not limited to, Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8, Trisomy 16, Turner Syndrome, Robertsonian translocation, DiGeorge Syndrome and Wolf-Hirschhorn Syndrome.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures (Tm).

The term "correction index" refers to nucleotides incorporated into amplification products that allow for identification and correction of amplification, sequencing or other experimental errors including the detection of deletion, substitution, or insertion of one or more bases during sequencing as well as nucleotide changes that may occur outside of sequencing such as oligo synthesis, amplification, and any other aspect of the assay. These correction indices may be stand-alone indices that are separate sequences, or they may be embedded within other indices to assist in confirming accuracy of the experimental techniques used, e.g., a correction index may be a subset of sequences used for universal amplification or a subset of nucleotides of a sample locus.

The term "diagnostic tool" as used herein refers to any composition or assay of the invention used in combination as, for example, in a system in order to carry out a diagnostic test or assay on a patient sample.

The term "disease trait" refers to a monogenic or polygenic trait associated with a pathological condition, e.g., a disease, disorder, syndrome or predisposition.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "informative locus" as used herein refers to a locus that is homozygous for the mother and heterozygous for the fetus on a particular chromosome or portion of a chromosome interrogated for purposes of determining a chromosomal abnormality, e.g., aneuploidy. Informative loci for use in the assay system of the invention include loci used for interrogation of a reference chromosome as well as loci used for interrogation of a chromosome that is putatively aneuploid.

The terms "locus" and "loci" as used herein refer to a locus of known location in a genome.

The term "maternal sample" as used herein refers to any sample taken from a pregnant mammal which comprises both fetal and maternal cell free genomic material (e.g., DNA). Preferably, maternal samples for use in the invention are obtained through relatively non-invasive means, e.g., phlebotomy or other standard techniques for extracting peripheral samples from a subject.

The term "melting temperature" or Tm is commonly defined as the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $T_m=81.5+16.6(\log 10[Na+]) 0.41(\%[G+C])-675/n-1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual*, 3rd Ed., Cold Spring Harbor Laboratory Press (2001)). Other references include more sophisticated computations, which take structural as well as sequence characteristics into account for the calculation of $T_m$.

"Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., sequence analysis, of one or more biological molecules using a microarray.

The term "monogenic trait" as used herein refers to any trait, normal or pathological, that is associated with a mutation or polymorphism in a single gene. Such traits include traits associated with a disease, disorder, or predisposition caused by a dysfunction in a single gene. Traits also include non-pathological characteristics (e.g., presence or absence of cell surface molecules on a specific cell type (e.g., blood group status)).

The term "non-maternal" allele means an allele with a polymorphism and/or mutation that is found in a fetal allele (e.g., an allele with a de novo SNP or mutation) and/or a paternal allele, but which is not found in the maternal allele.

By "non-polymorphic", when used with respect to detection of selected loci, is meant a detection of such locus, which may contain one or more polymorphisms, but in which the detection is not reliant on detection of the specific polymorphism within the region. Thus a selected locus may contain a polymorphism, but detection of the region using the assay system of the invention is based on occurrence of the region rather than the presence or absence of a particular polymorphism in that region.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

According to the present invention, a "nucleotide" may be unlabeled or detectably labeled by well known techniques. Fluorescent labels and their attachment to oligonucleotides are described in many reviews, including Haugland, *Handbook of Fluorescent Probes and Research Chemicals*, 9th Ed., Molecular Probes, Inc., Eugene Oreg. (2002); Keller and Manak, *DNA Probes*, 2nd Ed., Stockton Press, New York (1993); Eckstein, Ed., *Oligonucleotides and Analogues: A Practical Approach*, IRL Press, Oxford (1991); Wetmur, *Critical Reviews in Biochemistry and Molecular Biology*, 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both incorporated herein by reference, or by other chemical methods such as using a commercial automated oligonucleotide synthesizer.

The term "polygenic trait" as used herein refers to any trait, normal or pathological, that is associated with a mutation or polymorphism in more than a single gene. Such traits include traits associated with a disease, disorder, syndrome or predisposition caused by a dysfunction in two or more genes. Traits also include non-pathological characteristics associated with the interaction of two or more genes.

As used herein the term "polymerase" refers to an enzyme that links individual nucleotides together into a long strand, using another strand as a template. There are two general types of polymerase-DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes or variants in a locus that may be indicative of that particular loci, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "sample index" refers generally to a series of unique nucleotides (i.e., each sample index is unique to a sample in a multiplexed assay system for analysis of multiple samples). The sample index can thus be used to assist in loci identification for multiplexing of different samples in a single reaction vessel, such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely. The index may be combined with any other index to create one index that provides information for two properties (e.g., sample-identification index, sample-locus index).

The term "selected locus" as used herein refers to one or more loci corresponding to a chromosome or one or more selected loci associated with a monogenic and/or polygenic trait. Such selected loci may be directly isolated and enriched from the sample for detection, e.g., based on hybridization and/or other sequence-based techniques, or they may be amplified using the sample as a template prior to detection of the sequence. Loci for use in the assay systems of the present invention may be selected on the basis of DNA level variation between individuals, based upon specificity for a particular chromosome, based on CG content and/or required amplification conditions of the selected loci, or other characteristics that will be apparent to one skilled in the art upon reading the present disclosure.

The terms "sequencing", "sequence determination" and the like as used herein refers generally to any and all biochemical methods that may be used to determine the order of nucleotide bases in a nucleic acid.

The term "specifically binds", "specific binding" and the like as used herein, when referring to a binding partner (e.g., a nucleic acid probe or primer, antibody, etc.) that results in the generation of a statistically significant positive signal under the designated assay conditions. Typically the interaction will subsequently result in a detectable signal that is at least twice the standard deviation of any signal generated as a result of undesired interactions (background).

The term "status" as used herein in relationship to a gene refers to the sequence status of the alleles of a particular gene, including the coding regions and the non-coding regions that affect the translation and/or protein expression from that gene. The status of a gene associated with an autosomal dominant disease such as achondroplasia (e.g., the gene encoding the fibroblast growth factor receptor) or Huntington's disease (e.g., the Huntingtin gene), or for an X-linked disease in the case of a male fetus, can be classified as affected i.e., one allele possesses mutation(s) that is causative of the diseases or disorder, or non-affected, i.e. both alleles lack such mutations(s). The status of a gene associated with an autosomal recessive disease or a maternal gene associated with an X-linked recessive disorder, may be classified as affected, i.e., both alleles possess mutation(s) causative of the diseases or disorder; carrier, i.e. one allele possesses mutation(s) causative of the diseases or disorder; or non-affected, i.e. both alleles lack such mutations(s). The status of a gene may also indicate the presence or absence of a particular allele associated with a risk of developing a polygenic disease, e.g., a polymorphism that is protective against a particular disease or disorder or a polymorphism associated with an enhanced risk for a particular disease or disorder.

DETAILED DESCRIPTION OF THE INVENTION

The assay systems and methods described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "*Oligonucleotide Synthesis: A Practical Approach*" IRL Press, London (1984); Nelson and Cox, *Lehninger, Principles of Biochemistry*, 3rd Ed., W. H. Freeman Pub., New York (2000); and Berg et al., *Biochemistry*, 5th Ed., W.H. Freeman Pub., New York (2002), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "an," and "the" include plural referents unless the context clearly dictates otherwise. Thus, for example, reference to "a locus" refers to one, more than one, or mixtures of such loci, and reference to "an assay" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The use of selected loci in the assay methods of the invention provides amplification of loci from chromosomes of interest and/or reference chromosomes for detection of chromosomal abnormalities such as aneuploidies and large insertions or deletions. For example, the most common fetal aneuploidies associated with clinical outcomes in live births include chromosomes 13, 18, 21 and the sex chromosomes. Thus, the nucleic acids of interest for use in the assay of the invention are selected to detect aneuploidy of these particular chromosomes.

The sets of fixed sequence nucleic acids are designed to hybridize to at least two separate regions in a selected nucleic acid region. In preferred aspects, two or more separate oligos are used to hybridize to these regions to provide adjacent nucleic acids complementary to the selected nucleic acid region. In some aspects, however, a single probe can be used which comprises two or more distinct non-adjacent regions that are complementary to the selected loci (e.g., padlock probes) as described in more detail herein.

A distinct advantage of the invention is that the selected loci corresponding to copy number variation and/or polymorphisms can be further analyzed using a variety of detection and quantification techniques, including but not limited to hybridization techniques, digital PCR and high throughput sequencing determination techniques. Selection probes can be designed against any number of loci for any chromosome. Although amplification of the mixed sample prior to the identification and quantification of the selection nucleic acids regions is not mandatory, limited amplification prior to detection can be performed, in particular if the initial amounts of nucleic acid are limited.

FIG. 1 is a simplified flow chart of the general steps utilized in the assay systems of the invention. FIG. 1 shows method 100, where in a first step 110, a maternal nucleic acid sample is provided for analysis. At step 120, a first set of fixed sequence oligonucleotides are introduced to and combined with the maternal sample. The maternal sample can be prepared from virtually any sample as such techniques are known to those of skill in the art (see, e.g., Tietz Textbook of Clinical Chemistry and Molecular Diagnostics, 4th Ed., Chapter 2, Burtis, C. Ashwood E. and Bruns, D, eds. (2006); Chemical Weapons Convention Chemicals Analysis: Sample Collection, Preparation and Analytical Methods, Mesilaakso, M., ed., (2005); Pawliszyn, J., Sampling and Sample Preparation for Field and Laboratory, (2002); Venkatesh Iyengar, G., et al., Element Analysis of Biological Samples: Principles and Practices (1998); Drielak, S., Hot Zone Forensics: Chemical, Biological, and Radiological Evidence Collection (2004); Wells, D., High Throughput Bioanalytical Sample Preparation (Progress in Pharmaceutical and Biomedical Analysis) (2002)), each of which is incorporated by reference). Depending on the type of mixed sample chosen, additional processing and/or purification steps may be performed to obtain nucleic acid fragments of a desired purity or size, using processing methods including but not limited to sonication, nebulization, gel purification, PCR purification systems, nuclease cleavage, or a combination of these methods. In a preferred aspect, samples comprising cell-free DNA (cfDNA) are used.

At step 120, a first set of fixed sequence oligonucleotides are introduced to the mixed nucleic acid sample, under conditions that allow the first set of fixed sequence oligonucleotides to hybridize to selected loci in the maternal sample. The first set of fixed sequence oligonucleotides are capable of amplifying the loci and determining copy number variations and/or chromosomal abnormalities via detection of loci frequency and/or content. The nucleic acid sequences capable of determining copy number variations or chromosomal abnormalities include sequences that allow for identification of chromosomal abnormalities such as duplications or deletions, aneuploidies, translocations, or inversions.

At step 130, a second set of fixed sequence oligonucleotides are introduced to and combined with the maternal sample and first set of fixed sequence oligonucleotides under conditions that allow the second set of fixed sequence oligonucleotides to hybridize to the maternal sample. The second set of fixed sequence oligonucleotides comprise nucleic acid sequences that are complementary to a selected locus or locus in the maternal sample, able to detect polymorphisms. Washing steps optionally may be included between steps 120 and 130, and 130 and 140.

Although the invention is described as the two sets of oligos introduced to the maternal sample sequentially, the order of the sets may be reversed from that described in the figures or, in preferred aspects, they can be introduced simultaneously.

At step 140, first and second sets of fixed sequence oligonucleotides that have hybridized to adjacent regions of the selected loci in the maternal sample are ligated, and at step 150, the ligated oligonucleotides are amplified. The ligated and amplified oligonucleotides are then detected and analyzed, which allows for determination of copy number variations or chromosomal abnormalities and identification of polymorphisms at step 160.

The sets of fixed sequence nucleic acids are designed to hybridize to at least two separate regions in a selected locus. In preferred aspects, two or more separate oligos are used to hybridize to these regions to provide adjacent nucleic acids complementary to the selected locus. In some aspects, however, a single probe can be used which comprises two or more distinct non-adjacent regions that are complementary to the selected loci including precircular probes such as so-called "padlock probes" or "molecular inversion probes (MIPs)".

The present invention provides an improved assay system over more random techniques such as massively parallel sequencing, shotgun sequencing, and the use of random digital PCR which have been used by others to detect copy number variations in maternal samples such as maternal blood. These aforementioned approaches rely upon sequencing of all or a statistically significant population of DNA fragments in a sample, followed by mapping of these fragments or otherwise associating the fragments to their appropriate chromosomes. The identified fragments are then compared against each other or against some other reference (e.g., normal chromosomal makeup) to determine CNVs on particular chromosomes. These methods are inherently inefficient as compared to the present invention, as the primary chromosomes of interest only constitute a minority of data that is generated from the detection of such DNA fragments in the maternal samples.

The assays of the present invention provide targeted detection of selected loci, which provides information on both the content of the selected region (i.e., presence of a polymorphic region) and information on the frequency of the detected region in a sample (with or without detecting any putative polymorphisms in that region). This key feature provides the ability to detect both copy number of selected regions and the presence or absence of polymorphisms in a selected region as a single data set from performance of a multiplexed assay of the invention.

Techniques that are dependent upon a very broad sampling of DNA in a sample provide a very broad coverage of the DNA analyzed, but in fact are sampling the DNA contained within a sample on a IX or less basis (i.e., subsampling). In contrast, the selective amplification used in the present assays are specifically designed to provide depth of coverage of particular loci of interest, and provide a "super-sampling" of such selected loci with an average sequence coverage of preferably 2× or more, more preferably sequence coverage of 100× of more, even more preferably sequence coverage of 1000× or more of the selected loci (including from fetal sources) present in the initial maternal sample. Thus, the assay systems of the invention provide a more efficient and economical use of data, and the substantial majority of ligated oligonucleotides analyzed following amplification (i.e., the amplification products) result in affirmative information about the presence of selected loci in the maternal sample.

A distinct advantage of the invention is that the ligation products resulting from the assays corresponding to chromosomal abnormalities and/or chromosomal abnormalities and polymorphisms can be analyzed using a variety of detection and quantification techniques, including but not limited to hybridization techniques, digital PCR and high throughput sequencing determination techniques.

The assay systems of the invention provide a more efficient and economical use of data, and the substantial majority of sequences analyzed following sample amplification result in affirmative information about the presence of a particular CNV in the mixed sample. Thus, unlike techniques relying on massively parallel sequencing or random digital "counting" of chromosome regions and subsequent identification of relevant data from such counts, the assay system of the invention provides a much more efficient use of data collection than the random approaches taught by others in the art.

Assay Methods

The assay systems of the invention utilize a general scheme as described above, though many different configurations and variations can be employed, a few of which are described below and more of which are exemplified in U.S. Ser. No. 61/371,605 filed Aug. 6, 2010, and U.S. Ser. No. 13/013,732, both of which are incorporated by reference herein in their entirety.

Figure 2:
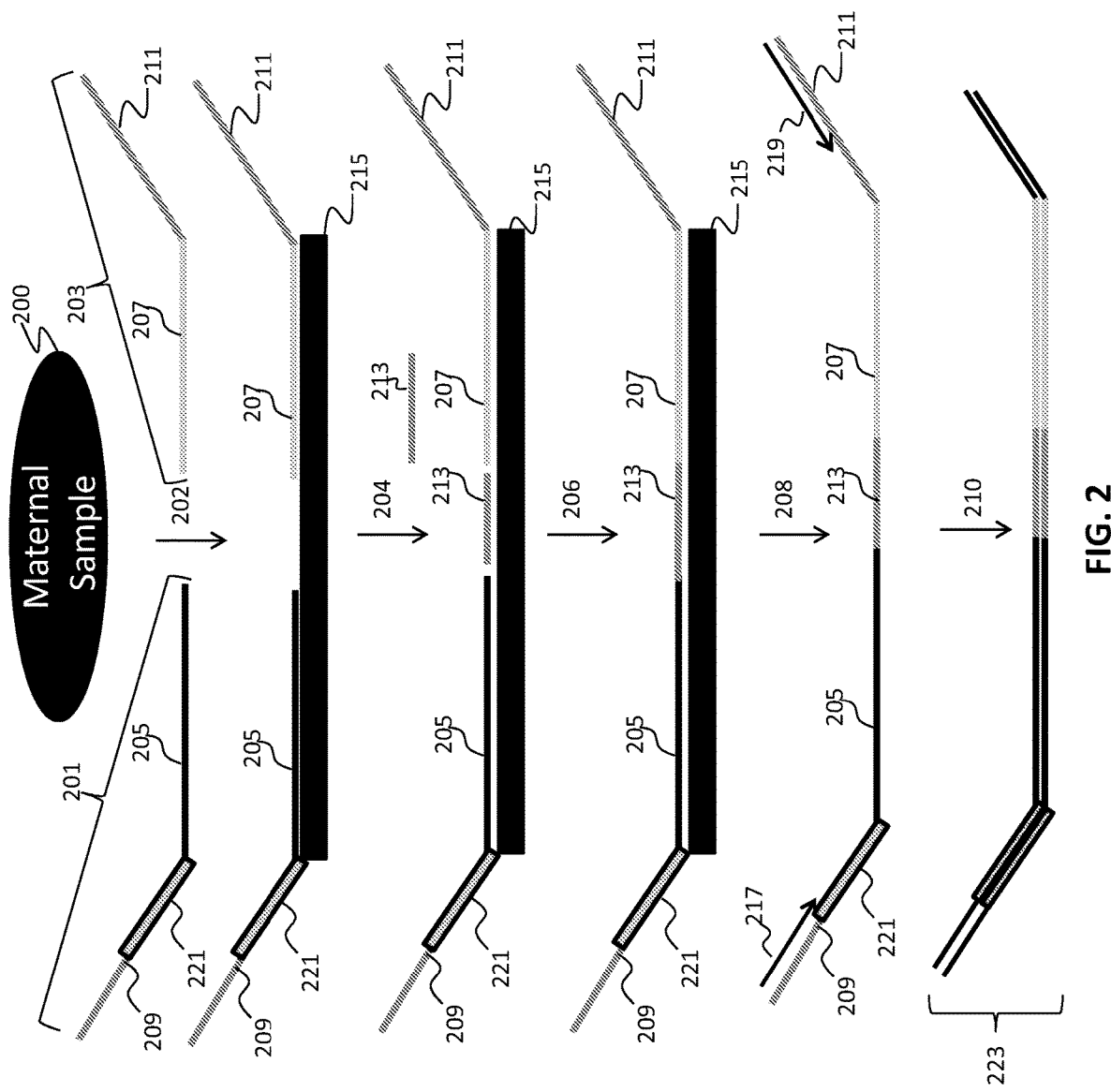
FIG. 2 illustrates a first general schematic for a ligation-based assay system of the invention.

FIG. 2 illustrates a first general schematic for a ligation-based assay system of the invention. The fixed sequence oligonucleotides 201, 203 comprise universal primer regions 209 and 211, respectively, and regions complementary to the selected locus 205 and 207, respectively. However, in addition, the assay system in FIG. 2 employs a sample index region 221 on the first fixed sequence oligonucleotide 201. In certain aspects, all or a portion of the sequences of the selected loci are directly detected using the described techniques, e.g., by sequence determination or hybridization techniques. In the example of FIG. 2, a sample index is associated with the first fixed sequence oligonucleotide 201. The detection of the indices can identify a sequence from a specific sample in a highly multiplexed assay system.

At step 202, the fixed sequence oligonucleotides 201, 203 are introduced in step 202 to the maternal sample 200 and allowed to specifically bind to the selected locus 215. Following hybridization, the unhybridized fixed sequence oligonucleotides are preferably separated from the remainder of the genetic sample (by, e.g., washing—not shown). A bridging oligo is then introduced and allowed to hybridize in step 204 to the region of the locus 215 between the first 201 and second 203 fixed sequence oligonucleotides. The bound oligonucleotides are ligated at step 206 to create a contiguous nucleic acid spanning and complementary to the locus of interest. In certain aspects of the invention, the bridging oligonucleotides of are between 2-45 nucleotides in length. In a specific aspect, the bridging oligonucleotides are between 3-9 nucleotides in length. In yet another specific aspect, the bridging oligonucleotides are between 10-30 nucleotides in length.

Following ligation, the ligation product is eluted from the gDNA template. Universal primers 217, 219 are introduced in step 208 to amplify the ligated first and second fixed sequence oligonucleotides to create 210 amplification products 223 that comprise the sequence of the locus of interest. These products 223 are isolated, detected, identified and quantified to provide information regarding the presence and amount of the selected loci in the maternal sample. Preferably, the amplification products are detected and quantified through sequence determination. In specific aspects, it is desirable to determine the sequences of both the index and the amplification products, for example, to provide identification of the sample as well as the locus. The indices envisioned in the invention may be associated with the first fixed sequence oligonucleotides, the second fixed sequence oligonucleotides or both. Alternatively or in addition, indices may be associated with primers that are used to amplify the ligated first and second fixed sequence oligonucleotides, which also serves to incorporate indices into the amplification products.

In preferred aspects, indices representative of the maternal sample from which a nucleic acid may be isolated are used to identify the source of the selected loci in a multiplexed assay system. In such aspects, the nucleic acids are uniquely identified with the sample index. Uniquely identified oligonucleotides may then be combined into a single reaction vessel with nucleic acids from other maternal samples prior to sequencing. In such a case, the sequencing data is segregated by the unique sample index to determine the frequency of each target locus for each maternal sample and to determine whether there is a chromosomal abnormality in an individual sample.

In aspects of the invention using sample indices, the fixed sequence oligonucleotides preferably are designed so that sample indices comprising identifying information are located between the universal primer regions 209 and 211 and the regions complementary to the selected loci in the sample 205 and 207. Alternatively, the indices and universal amplification sequences can be added to the ligated first and second fixed sequence oligos (and the bridging oligo, if present) by including these indices in the primers used to amplify the ligation products for separate samples. In either case, preferably the indices are encoded upstream of the locus-specific sequences but downstream of the universal primers so that they are preserved upon amplification.

Figure 3:
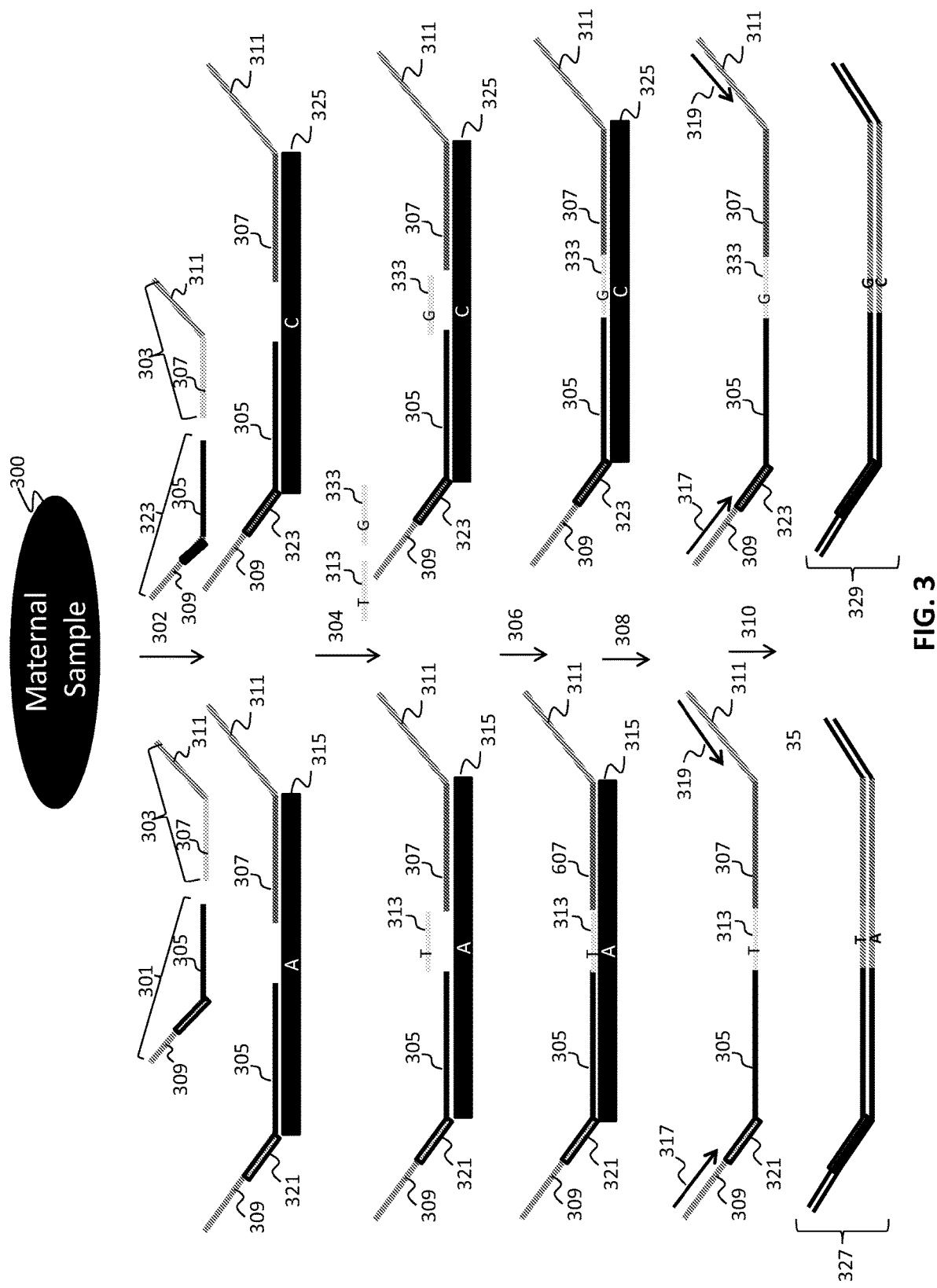
FIG. 3 illustrates a first general schematic for a ligation-based assay system of the invention.

FIG. 3 exemplifies methods of the assay system in which one or more bridging oligonucleotides are employed and exemplifies how polymorphisms may be detected and identified. In FIG. 3, two fixed sets of sequence oligonucleotides are used which comprise substantially the same universal primers 309, 311 and sequence-specific regions 305, 307, but comprise different sample indices, 321, 323 on the fixed sequence oligonucleotides of the set where the different indices correspond to different base sequences for the single nucleotide polymorphism present in a particular sample. The ligation reactions are carried out with material from the same maternal sample 300, but in separate tubes with the different allele-specific oligo sets. Bridging oligonucleotides corresponding to two possible nucleotides for this SNP in the selected loci 313, 333 are used to detect of the selected locus in each ligation reaction. Two allele indices 321, 323 that are indicative of the particular polymorphic alleles are incorporated into the amplification products so that sequence determination of the actual sequence of the ligated first, second and bridging oligonucleotides are not necessarily needed, although the sequences of the entire ligation products may still be determined to identify and/or provide confirmation.

Each of the fixed sequence oligonucleotides comprises a region complementary to the selected locus 305, 307, and universal primer regions 309, 311 used to amplify the different selected loci following initial selection and/or isolation of the selected loci from the maternal sample. The universal primer regions are located at the ends of the fixed sequence oligonucleotides 301, 303, and 323 flanking the indices and the regions complementary to the nucleic acid of interest, thus preserving the nucleic acid-specific sequences and the sample indices in the products of any universal amplification methods. The fixed sequence oligonucleotides 301, 303, 323 are introduced at step 302 to an aliquot of the genetic sample 300 and allowed to specifically bind to the selected loci 315 or 325. Following hybridization, the unhybridized fixed sequence oligonucleotides are preferably separated from the remainder of the genetic sample by, e.g., washing (not shown).

The bridging oligos corresponding to an A/T SNP 313 or a G/C SNP 333 are introduced and allowed to bind in step 304 to the region of the selected locus 315 or 325 between the first 305 and second 307 nucleic acid-complementary regions of the fixed sequence oligonucleotides. Alternatively, the bridging oligos 313, 333 can be introduced to the sample simultaneously with the fixed sequence oligonucleotides. The bound oligonucleotides are ligated in step 306 in the single reaction mixture to create a contiguous nucleic acid spanning and complementary to the selected locus.

Following ligation, the separate reactions may preferably be combined for the universal amplification and detection steps. Universal primers 317, 319 are introduced to the combined reactions at step 308 to amplify the ligated template regions and create at step 310 ligated first and second fixed sequence oligos and bridging oligo products 327, 329 that comprise the sequence of the selected locus representing both SNPs in the selected locus. These ligation products 327, 329 are detected and quantified through sequence determination of the ligation product, through the sample index and/or the region of the product containing the SNP in the selected locus.

Figure 4:
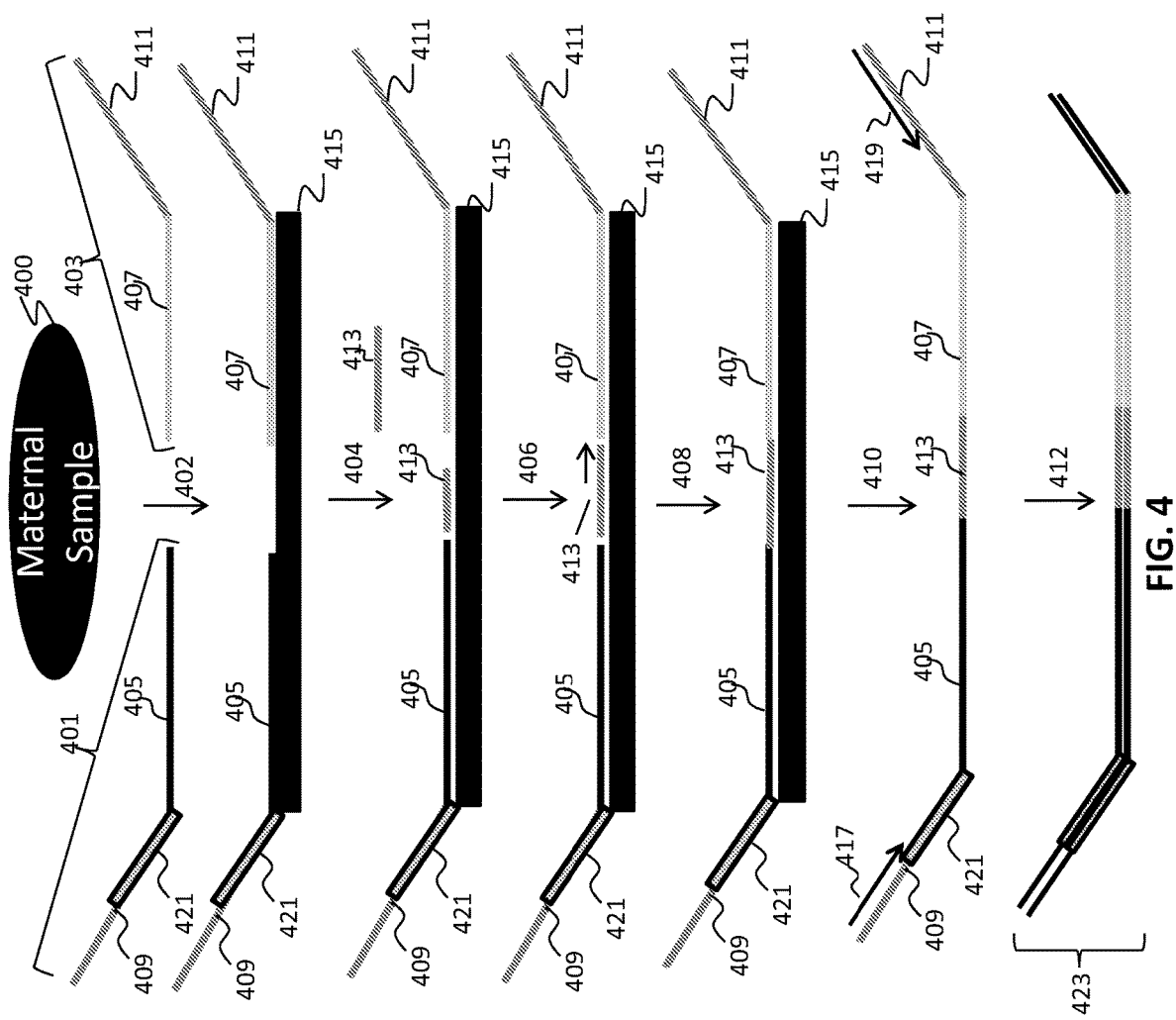
FIG. 4 is a third general schematic for a ligation-based assay system of the invention.

In an alternative configuration of the methods of the assay systems of the invention, the bridging oligo may hybridize to a region that is not directly adjacent to the region complementary to one or both of the fixed sequence oligos, and an intermediate step requiring extension of one or more of the oligos is necessary prior to ligation. For example, as illustrated in FIG. 4, each set of oligonucleotides preferably contains two oligonucleotides 401, 403 of fixed sequence and one or more bridging oligonucleotides 413. Each of the fixed sequence oligonucleotides comprises a region complementary to the selected locus 405, 407, and primer sequences, preferably universal primer sequences, 409, 411, i.e., oligo regions complementary to universal primers. The primer sequences 409, 411 are located at or near the ends of the fixed sequence oligonucleotides 401, 403, and thus preserve the nucleic acid-specific sequences in the products of any universal amplification methods. The fixed sequence oligonucleotides 401, 403 are introduced at step 402 to the maternal sample 400 and allowed to specifically bind to the complementary portions of the locus of interest 415. Following hybridization, the unhybridized fixed sequence oligonucleotides are preferably separated from the remainder of the genetic sample (not shown).

The bridging oligonucleotide is then introduced at step 404 and allowed to bind to the region of the selected locus 415 between the first 401 and second 403 fixed sequence oligonucleotides. Alternatively, the bridging oligo can be introduced simultaneously with the fixed sequence oligonucleotides. In this exemplary aspect, the bridging oligo hybridizes to a region directly adjacent to the first fixed sequence oligo region 405, but is separated by one or more nucleotides from the complementary region of the second fixed sequence oligonucleotide 407. Fallowing hybridization of the fixed sequence and bridging oligos, the bridging oligo 413 is extended at step 406, e.g., using a polymerase and dNTPs, to fill the gap between the bridging oligo 413 and the second fixed sequence oligo 403. Following extension, the bound oligonucleotides are ligated at step 408 to create a contiguous nucleic acid spanning and complementary to the locus of interest 415. After ligation, universal primers 417, 419 are introduced at step 410 to amplify the ligated first, second and bridging oligos to create at step 412 amplification products 423 that comprise the sequence of the selected locus of interest. Amplification products 423 are optionally isolated, detected, and quantified to provide information on the presence and amount of the selected locus(s) in the maternal sample.

Detecting Copy Number Variations

The assay systems utilize nucleic acid probes designed to identify, and preferably to isolate, selected nucleic acids regions in a maternal sample. Certain of the probes identity sequences of interest in selected loci interrogated for copy number (i.e. loci frequency), and other probes identify sequences that correspond to polymorphisms of interest (i.e. loci content) in nucleic acids corresponding to a fetal or maternal source in a maternal sample.

In specific aspects, the assay systems of the invention employ one or more selective amplification steps (e.g., using one or more primers that specifically hybridize to a selected locus) for isolating, amplifying or analyzing substantially all of the selected loci analyzed. This is in direct contrast to the random amplification approach used by others employing, e.g., massively parallel sequencing, as such amplification techniques generally involve random amplification of all or a substantial portion of the genome. In addition, although the initial sample can be enriched using methods such as general amplification to increase the copy number of nucleic acids in the maternal sample, preferably no enrichment steps are used prior to the hybridization, ligation, and amplification steps used to identify the loci of interest.

In a general aspect, the user of the invention analyzes multiple selected loci on different chromosomes. When multiple loci are analyzed for a sample, a preferred embodiment is to amplify all of the selected loci for each sample in one reaction vessel. The frequency or amount of the multiple selected loci are analyzed to determine whether a chromosomal abnormality exists, and the presence or absence of a polymorphism is analyzed to determine the presence or absence or likelihood calculation of a fetal chromosomal abnormality in a source in the maternal sample.

In preferred aspects, multiple selected loci from two or more samples may be amplified in a single reaction vessel, and the information simultaneously analyzed in a single data set, e.g., through sequence determination. The resulting data is then analyzed to separate the results for the different sample and used to determine the presence of absence of CNV and/or the presence of absence of polymorphisms for individual samples.

In one aspect, chromosomal abnormalities are identified in the assay system of the invention using multiple selected loci on multiple chromosomes, and the frequency of the selected loci on the multiple chromosomes compared to identity an increase likelihood of aneuploidy based on the ratios of the chromosomes. Normalization or standardization of the frequencies can be performed for one or more selected loci.

In another aspect, the assay system sums the frequencies of the selected loci on two or more chromosomes and then compares the sum of the selected loci on one chromosome against another chromosome to determine whether a chromosomal aneuploidy exists. In another aspect, the assay system analyzes subsets of selected loci on two or more chromosomes to determine whether a chromosomal aneuploidy exists for one of the two chromosomes. The comparison can be made either within the same or different chromosomes.

In certain aspects, the data used to determine the frequency of the selected loci may exclude outlier data that appear to be due to experimental error, or that have elevated or depressed levels based on an idiopathic genetic bias within a particular sample. In one example, the data used for summation may exclude DNA regions with a particularly elevated frequency in one or more samples. In another example, the data used for summation may exclude selected loci that are found in a particularly low abundance in one or more samples.

In another aspect subsets of loci can be chosen randomly but with sufficient numbers of loci to yield a statistically significant result in determining whether a chromosomal abnormality exists. Multiple analyses of different subsets of loci can be performed within a maternal sample to yield more statistical power. For example, if there are 100 selected regions for chromosome 21 and 100 selected regions for chromosome 18, a series of analyses could be performed that evaluate fewer than 100 regions for each of the chromosomes. In this example, selected loci are not being selectively excluded.

The quantity of different nucleic acids detectable on certain chromosomes may vary depending upon a number of factors, including general representation of loci in different cell sources in maternal samples, degradation rates of the different nucleic acids representing different loci in maternal samples, sample preparation methods, and the like. Thus, in another aspect, the quantity of particular loci on a chromosome is summed to determine the loci quantity for different chromosomes in the sample. The loci frequencies are summed for a particular chromosome, and the sum of the loci are used to determine aneuploidy. This aspect of the invention sums the frequencies of the individual loci on each chromosome and then compares the sum of the loci on one chromosome against another chromosome to determine whether a chromosomal abnormality exists.

The nucleic acids analyzed using the assay systems of the invention are preferably selectively amplified and optionally isolated from the maternal sample using primers specific to the locus of interest (e.g., to a locus of interest in a maternal sample). The primers for such selective amplification designed to isolate regions may be chosen for various reasons, but are preferably designed to 1) efficiently amplify a region from the chromosome of interest; 2) have a predictable range of expression from maternal and/or fetal sources in different maternal samples; 3) be distinctive to the particular chromosome, i.e., not amplify homologous regions on other chromosomes. The following are exemplary techniques that may be employed in the assay system or the invention.

The assay system of the invention detects both fetal aneuploidies and specific chromosomal abnormalities through identification and quantification of specific loci of interest. Such additional abnormalities include, but are not limited to, deletion mutations, insertion mutations, copy number polymorphisms, copy number variants, chromosome 22q11 deletion syndrome, 11q deletion syndrome on chromosome 11, 8p deletion syndrome on chromosome 8, and the like. Generally, at least two selected nucleic acid sequences present on the same or separate chromosomes are analyzed, and at least one of the selected loci is associated with the fetal allelic abnormality. The sequences of the two selected loci and number of copies of the two selected loci are then compared to determine whether the chromosomal abnormality is present, and if so, the nature of the abnormality.

While much of the description contained herein describes detecting aneuploidy by counting the abundance of loci on one or more putative aneuploid chromosomes and the abundance of loci on one or more normal chromosomes, the same techniques may be used to detect copy number variations where such copy number variation occurs on only a portion of a chromosome. In this detection of the copy number variations, multiple loci within the putative copy number variation location are compared to multiple loci outside of the putative copy number variation location. For instance, one may detect a chromosome 22q11 deletion syndrome in a fetus in a maternal sample by selecting two or more nucleic regions within the 22q11 deletion and two or more loci outside of the 22q11 deletion. The loci outside of the 22q11 deletion may be on another region of Chromosome 22 or may be on a completely different chromosome. The abundance of each loci is determined by the methods described in this application.

In some aspects a universal amplification may be used for amplifying the loci. In some aspects, the loci for each sample are assayed in a single reaction in a single vessel. In other aspects, loci from multiple samples can be assayed in a single reaction in a single vessel.

Certain aspects of the invention can detect a deletion, including the boundaries of such deletions. In some aspects, at least 24 selected loci may be used within the region of the putative deletion and at least 24 selected loci may be used outside of the region of the putative deletion. In another aspect at least 48 selected loci may be used within the region of the putative deletion and at least 48 selected loci may be used outside of the region of the putative deletion. In another aspect at least 48 selected loci may be used within the region of the putative deletion and at least 96 selected loci may be used outside of the region of the putative deletion. In another aspect at least 48 selected loci may be used within the region of the putative deletion and at least 192 selected loci may be used outside of the region of the putative deletion. In a preferred aspect at least 384 selected loci may be used within the region of the putative deletion and at least 384 selected loci may be used outside of the region of the putative deletion. The loci within the deletion are then summed as are the loci outside of the deletion. These sums are then compared to each other to determine the presence or absence of a deletion. Optionally, the sums are put into a ratio and that ratio may be compared to an average ratio created from a normal population. When the ratio for a sample falls statistically outside of an expected ratio, the deletion is detected. The threshold for the detection of a deletion may be twice or more, preferably four or more times the variation calculated in the normal population.

Polymorphisms Associated with Diseases or Predispositions

The assay systems of the invention are utilized to detect polymorphisms, such as those associated with an autosomal dominant or recessive disease or predisposition disorder. Given the multiplexed nature of the assay systems of the invention, this detection takes place in the same assay as the detection of chromosomal abnormalities in the fetus. Thus a single assay system can provide diagnostic information on different classes of genetic mutations. Accordingly, as the preferred assay systems of the invention are highly multiplexed and able to interrogate hundreds or even thousands of nucleic acids within a maternal sample, in certain aspects it is desirable to interrogate the sample for nucleic acid markers within the maternal sample, e.g., nucleic acids associated with genetic risk or that identify the presence or absence of infectious organisms. Thus, the assay systems provide detection of such nucleic acids in conjunction with the detection of nucleic acids for copy number determination within a maternal sample.

Thus, the assay system of the invention can be used to detect polymorphisms in a maternal sample, where such polymorphisms are associated with genes associated with autosomal recessive disorders including but not limited to blood disorders (e.g., sickle cell anemia, hemophilia or thalassemia), Tay-Sachs, cystic fibrosis, muscular dystrophy, Parkinson's disease, Alzheimer's disease and the like; mutations associated with autosomal dominant disorders such as Huntington's disease or achondroplasia; and copy number variations associated with single gene disorders (e.g., spinal muscular atrophy).

In other specific aspects, the assay system of the invention can be used to detect fetal mutations or polymorphisms in a maternal sample, where such mutations or polymorphisms are associated with polygenic disorders such as coronary heart disease, diabetes, hypertension, congenital heart defects, and epilepsy. Examples include mutations in genes associated with predispositions such as mutations in cancer susceptibility genes, (e.g. mutations in BRCA1 or II or in p53); polymorphisms associated with increased risk of developing later onset diseases, such as the apoE3 gene polymorphism associated with Alzheimer's risk, In addition to detection of chromosomal abnormalities and single gene mutations or polymorphisms associated with monogenic or polygenic disease, disorders or predispositions, the assay systems of the invention may identify infectious agents in the maternal sample. Specifically, changes in immunity and physiology during pregnancy may make pregnant women more susceptible to or more severely affected by infectious diseases. In fact, pregnancy itself may be a risk factor for acquiring certain infectious diseases, such as toxoplasmosis, Hansen disease, and listeriosis. In addition, for pregnant women or subjects with suppressed immune systems, certain infectious diseases such as influenza and varicella may have a more severe clinical course, increased complication rate, and higher case-fatality rate. Identification of infectious disease agents may therefore allow better treatment for maternal disease during pregnancy, leading to a better overall outcome for both mother and fetus.

Moreover, certain infectious agents can be passed to the fetus via vertical transmission, i.e. spread of infections from mother to baby. These infections may occur while the fetus is still in the uterus, during labor and delivery, or after delivery (such as while breastfeeding).

Thus, is some preferred aspects, the assay system may include detection of exogenous sequences, e.g., sequences from infectious organisms that may have an adverse effect on the health and/or viability of the fetus or infant, in order to protect maternal, fetal, and or infant health.

Exemplary infections which can be spread via vertical transmission, and which can be tested for using the assay methods of the invention, include but are not limited to congenital infections, perinatal infections and postnatal infections.

Congenital infections are passed in utero by crossing the placenta to infect the fetus. Many infectious microbes can cause congenital infections, leading to problems in fetal development or even death. TORCH is an acronym for several of the more common congenital infections. These are: toxoplasmosis, other infections (e.g., syphilis, hepatitis B, Coxsackie virus, Epstein-Barr virus, varicella-zoster virus (chicken pox), and human parvovirus B19 (fifth disease)), rubella, cytomegalovirus (CMV), and herpes simplex virus.

Perinatal infections refer to infections that occur as the baby moves through an infected birth canal or through contamination with fecal matter during delivery. These infections can include, but are not limited to, sexually-transmitted diseases (e.g., gonorrhea, chlamydia, herpes simplex virus, human papilloma virus, etc.) CMV, and Group B Streptococci (GBS).

Infections spread from mother to baby following delivery are known as postnatal infections. These infections can be spread during breastfeeding through infectious microbes found in the mother's breast milk. Some examples of postnatal infections are CMV, Human immunodeficiency virus (HIV), Hepatitis C Virus (HCV), and GBS.

Selected Amplification

Numerous selective amplification methods can be used to provide the amplified nucleic acids that are analyzed in the assay systems of the invention, and such methods are preferably used to increase the copy numbers of a locus of interest in a maternal sample in a manner that allows preservation of information concerning the initial content of the locus in the maternal sample. Although not all combinations of amplification and analysis are described herein in detail, it is well within the skill of those in the art to utilize different amplification methods and/or analytic tools to isolate and/or analyze the nucleic acids of region consistent with this specification, and such variations will be apparent to one skilled in the art upon reading the present disclosure.

Such amplification methods include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al., Nucleic Acids Res. 20(7):1691-6 (1992), and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR. In a preferred aspect the DNA is amplified using adaptor-ligation and single primer PCR. Other available methods of amplification, such as balanced PCR (Makrigiorgos, et al., Nature Biotechnol, 20:936-9 (2002)) and isothermal amplification methods such as nucleic acid sequence based amplification (NASBA) and self-sustained sequence replication (Guatelli et al., PNAS USA 87:1874 (1990)). Based on such methodologies, a person skilled in the art readily can design primers in any suitable regions 5' and 3' to a locus of interest. Such primers may be used to amplify DNA of any length so long that it contains the locus of interest in its sequence.

The length of an amplified selected locus from a genomic region of interest is long enough to provide enough sequence information to distinguish it from other nucleic acids that are amplified and/or selected. Generally, an amplified nucleic acid is at least about 16 nucleotides in length, and more typically, an amplified nucleic acid is at least about 20 nucleotides in length. In a preferred aspect of the invention, an amplified nucleic acid is at least about 30 nucleotides in length. In a more preferred aspect of the invention, an amplified nucleic acid is at least about 32, 40, 45, 50, or 60 nucleotides in length. In other aspects of the invention, an amplified nucleic acid can be about 100, 150 or up to 200 in length.

In certain aspects, the selected amplification comprises an initial linear amplification step. This can be particularly useful if the starting amount of DNA from the maternal sample is quite limited, e.g., where the cell-free DNA in a sample is available in limited quantities. This mechanism increases the amount of DNA molecules that are representative of the original DNA content, and help to reduce sampling error where accurate quantification of the DNA or a fraction of the DNA (e.g., fetal DNA contribution in a maternal sample) is needed.

Thus, in one aspect, a limited number of cycles of sequence-specific linear amplification are performed on the starting maternal sample comprising cfDNA. The number of cycles is generally less than that used for a typical PCR amplification, e.g., 5-30 cycles or fewer. Primers or probes may be designed to amplify specific genomic segments or regions. The primers or probes may be modified with an end label at the 5' end (e.g. with biotin) or elsewhere along the primer or probe such that the amplification products could be purified or attached to a solid substrate (e.g., bead or array) for further isolation or analysis. In a preferred aspect, the primers are multiplexed such that a single reaction yields multiple DNA fragments from different regions. Amplification products from the linear amplification could then be further amplified with standard PCR methods or with additional linear amplification.

For example, cfDNA can be isolated from blood, plasma, or serum from a pregnant woman, and incubated with primers against a set number of loci that correspond to chromosomes of interest. Preferably, the number of primers used for initial linear amplification will be 12 or more, more preferably 24 or more, more preferably 36 or more, even more preferably 48 or more, and even more preferably 96 or more. Each of the primers corresponds to a single locus, and is optionally tagged for identification and/or isolation. A limited number of cycles, preferably 10 or fewer, are performed with linear amplification. The amplification products are subsequently isolated, e.g., when the primers are linked to a biotin molecule the amplification products can be isolated via binding to avidin or streptavidin on a solid substrate. The products are then subjected to further biochemical processes such as further amplification with other primers and/or detection techniques such as sequence determination and hybridization.

Efficiencies of linear amplification may vary between sites and between cycles so that in certain systems normalization may be used to ensure that the products from the linear amplification are representative of the nucleic acid content starting material. One practicing the assay system of the invention can utilize information from various samples to determine variation in nucleic acid levels, including variation in different loci in individual samples and/or between the same loci in different samples following the limited initial linear amplification. Such information can be used in normalization to prevent skewing of initial levels of DNA content.

Universal Amplification

In preferred aspects of the invention, the selectively amplified loci are preferably further amplified through universal amplification of all or substantially all of the various loci to be analyzed using the assay systems of the invention. Universal primer regions are added to the fixed sequence oligonucleotides so that the selectively amplified loci may be further amplified in a single universal amplification reaction. These universal primer sequences may be added to the nucleic acids regions during the selective amplification process, i.e., the primers for selective amplification have universal primer sequences that flank a locus. Alternatively, adapters comprising universal amplification sequences can be added to the ends of the selected nucleic acids as adapters following amplification and isolation of the selected nucleic acids from the maternal sample.

In one exemplary aspect, nucleic acids are initially amplified from a maternal sample using primers complementary to selected regions of the chromosomes of interest, followed by a universal amplification step to increase the number of loci for analysis. This introduction of primer regions to the initial amplification products from a maternal sample allows a subsequent controlled universal amplification of all or a portion of selected nucleic acids prior to or during analysis, e.g. sequence determination.

Bias and variability can be introduced during DNA amplification, such as that seen during polymerase chain reaction (PCR). In cases where an amplification reaction is multiplexed, there is the potential that loci will amplify at different rates or efficiency. Part of this may be due to the variety of primers in a multiplex reaction with some having better efficiency (i.e. hybridization) than others, or some working better in specific experimental conditions due to the base composition. Each set of primers for a given locus may behave differently based on sequence context of the primer and template DNA, buffer conditions, and other conditions. A universal DNA amplification for a multiplexed assay system will generally introduce less bias and variability.

Accordingly, in a one aspect, a small number (e.g., 1-10, preferably 3-5) of cycles of selected amplification or nucleic acid enrichment of the initial sample in a multiplexed mixture reaction are performed, followed by universal amplification using introduced universal primers. The number of cycles using universal primers will vary, but will preferably be at least 10 cycles, more preferably at least 5 cycles, even more preferably 20 cycles or more. By moving to universal amplification following a lower number of amplification cycles, the bias of having certain loci amplify at greater rates than others is reduced.

Optionally, the assay system will include a step between the selected amplification and universal amplification to remove any excess nucleic acids that are not specifically amplified in the selected amplification.

The whole product or an aliquot of the product from the selected amplification may be used for the universal amplification. The same or different conditions (e.g., polymerase, buffers, and the like) may be used in the amplification steps, e.g., to ensure that bias and variability are not inadvertently introduced due to experimental conditions. In addition, variations in primer concentrations may be used to effectively limit the number of sequence specific amplification cycles.

In certain aspects, the universal primer regions of the primers or adapters used in the assay system are designed to be compatible with conventional multiplexed assay methods that utilize general priming mechanisms to analyze large numbers of nucleic acids simultaneously in one reaction in one vessel. Such "universal" priming methods allow for efficient, high volume analysis of the quantity of loci present in a maternal sample, and allow for comprehensive quantification of the presence of loci within such a maternal sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420.

Some aspects utilize coupled reactions for multiplex detection of nucleic acid sequences where oligonucleotides from an early phase of each process contain sequences which may be used by oligonucleotides from a later phase of the process. Exemplary processes for amplifying and/or detecting nucleic acids in samples can be used, alone or in combination, including but not limited to the methods described below, each of which are incorporated by reference in their entirety.

In certain aspects, the assay system of the invention utilizes one of the following combined selective and universal amplification techniques: (1) ligase detection reaction ("LDR") coupled with polymerase chain reaction ("PCR"); (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe LDR coupled PCR for nucleic acid detection.

Barany et al., U.S. Pat. Nos. 7,556,924 and 6,858,412, describe the use of precircle probes (also called "padlock probes" or "multi-inversion probes") with coupled LDR and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping.

Ronaghi et al., U.S. Pat. No. 7,622,281 describes amplification techniques for labeling and amplifying a nucleic acid using an adapter comprising a unique primer and a barcode.

In some cases, a single assay may employ a combination of the above-described methods. For example, some of the loci may be detected using fixed sequence oligonucleotides that bind to adjacent, complementary regions on a locus, while other loci may be detected using bridging loci in the same assay. In another example, some of the loci may be detected using fixed sequence oligonucleotides that bind to adjacent, complementary regions on a locus, while other loci may require a primer extension step to join the fixed sequence oligonucleotides.

In a preferred aspect, the amplification products are multiplexed, as described previously. In a preferred aspect, the multiplex amplification products are quantified by analysis of the amplification products. In a preferred aspect, a representational sample of individual molecules from the amplification processes is isolated from the other molecules for further analysis. To obtain a representational sample of individual molecules, the average number of molecules per locus must exceed the sampling noise created by the multiplexed reaction. In one aspect, the average number per locus is greater than 100. In another aspect, the average number per locus is greater than 500. In another aspect the average number per locus is greater than 1000.

Individual molecules from the amplification product are preferably isolated physically from the other molecules in a manner that allows the different amplification products to be distinguished from one another in analysis. In a preferred aspect, this isolation occurs on a solid substrate. The isolated molecule may be associated with a particular identifiable or physical address either prior to analysis, or the address may become known for the particular amplification products based on the outcome of the analysis. The substrate may be a planar surface or three-dimensional surface such as a bead.

Once isolated, the individual amplification product may be further amplified to make multiple identical copies of that molecule at the same known or identifiable location. The amplification may occur before or after that location becomes an identifiable or physical address. The amplification product and or its copies (which may be identical or complementary to the amplification product) are then analyzed based on the sequence of the amplification product or its copies to identify the particular locus and/or allele it represents.

In a preferred aspect, the entire length of the amplification product or a portion of the amplification product may be analyzed using sequence determination. The number of bases that need to be determined must be sufficient to uniquely identify the amplification product as belonging to a specific locus and/or allele. In one preferred aspect, the amplification product is analyzed through sequence determination of the selected amplification product.

Numerous methods of sequence determination are compatible with the assay systems of the inventions. Exemplary methods for sequence determination include, but are not limited to, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100:414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Sequence information may be determined using methods that determine many (typically thousands to billions) of nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

Alternatively, in another aspect, the entire length of the amplification product or a portion of the amplification product may be analyzed using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Variation Minimization within and Between Samples

One challenge with the detection of chromosomal abnormalities in a fetus by detection in a maternal sample is that the nucleic acids from the fetal cell are present in much lower abundance than the nucleic acids from normal cell type. In the case of a maternal sample containing fetal and maternal cell free DNA, the cell free fetal DNA as a percentage of the total cell free DNA may vary from less than one to forty percent, and most commonly is present at or below twenty percent and frequently at or below ten percent. In the detection of an aneuploidy such as Trisomy 21 (Down Syndrome) in the fetal DNA of such maternal sample, the relative increase in Chromosome 21 is 50% in the fetal DNA and thus as a percentage of the total DNA in a maternal sample where, as an example, the fetal DNA is 5% of the total, the increase in Chromosome 21 as a percentage of the total is 2.5%. If one is to detect this difference robustly through the methods described herein, the variation in the measurement of Chromosome 21 has to be much less than the percent increase of Chromosome 21.

The variation between levels found between samples and/or for loci within a sample may be minimized in a combination of analytical methods, many of which are described in this application. For instance, variation is lessened by using an internal reference in the assay. An example of an internal reference is the use of a chromosome present in a "normal" abundance (e.g., disomy for an autosome) to compare against a chromosome present in putatively abnormal abundance, such as aneuploidy, in the same sample. While the use of one such "normal" chromosome as a reference chromosome may be sufficient, it is also possible to use two or more normal chromosomes as the internal reference chromosomes to increase the statistical power of the quantification.

One method of using an internal reference is to calculate a ratio of abundance of the putatively abnormal chromosomes to the abundance of the normal chromosomes in a sample, called a chromosomal ratio. In calculating the chromosomal ratio, the abundance or counts of each of the loci for each chromosome are summed together to calculate the total counts for each chromosome. The total counts for one chromosome are then divided by the total counts for a different chromosome to create a chromosomal ratio for those two chromosomes.

Alternatively, a chromosomal ratio for each chromosome may be calculated by first summing the counts of each of the loci for each chromosome, and then dividing the sum for one chromosome by the total sum for two or more chromosomes. Once calculated, the chromosomal ratio is then compared to the average chromosomal ratio from a normal population.

The average may be the mean, median, mode or other average, with or without normalization and exclusion of outlier data. In a preferred aspect, the mean is used. In developing the data set for the chromosomal ratio from the normal population, the normal variation of the measured chromosomes is calculated. This variation may be expressed a number of ways, most typically as the coefficient of variation, or CV. When the chromosomal ratio from the sample is compared to the average chromosomal ratio from a normal population, if the chromosomal ratio for the sample falls statistically outside of the average chromosomal ratio for the normal population, the sample contains an aneuploidy. The criteria for setting the statistical threshold to declare an aneuploidy depend upon the variation in the measurement of the chromosomal ratio and the acceptable false positive and false negative rates for the desired assay. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is determined by summing the counts of loci by chromosome. Typically, the same number of selected loci for each chromosome is used. An alternative method for generating the chromosomal ratio would be to calculate the average counts for the loci for each chromosome. The average may be any estimate of the mean, median or mode, although typically an average is used. The average may be the mean of all counts or some variation such as a trimmed or weighted average. Once the average counts for each chromosome have been calculated, the average counts for each chromosome may be divided by the other to obtain a chromosomal ratio between two chromosomes, the average counts for each chromosome may be divided by the sum of the averages for all measured chromosomes to obtain a chromosomal ratio for each chromosome as described above. As highlighted above, the ability to detect an aneuploidy in a maternal sample where the putative DNA is in low relative abundance depends greatly on the variation in the measurements of different selected loci in the assay. Numerous analytical methods can be used which reduce this variation and thus improve the sensitivity of this method to detect aneuploidy. One method for reducing variability of the assay is to increase the number of selected loci used to calculate the abundance of the chromosomes. In general, if the measured variation of a single selected locus of a chromosome is X % and Y different selected loci are measured on the same chromosome, the variation of the measurement of the chromosomal abundance calculated by summing or averaging the abundance of each selected locus on that chromosome will be approximately X % divided by $Y^{1/2}$. Stated differently, the variation of the measurement of the chromosome abundance would be approximately the average variation of the measurement of each selected locus' abundance divided by the square root of the number of loci.

In a preferred aspect of this invention, the number of loci measured for each chromosome is at least 24. In another preferred aspect of this invention, the number of selected loci measured for each chromosome is at least 48. In another preferred aspect of this invention, the number of selected loci measured for each chromosome is at least 100. In another preferred aspect of this invention the number of selected loci measured for each chromosome is at least 200. There is incremental cost to measuring each locus and thus it is important to minimize the number of each selected locus. In a preferred aspect of this invention, the number of selected loci measured for each chromosome is less than 2000. In a preferred aspect of this invention, the number of selected loci measured for each chromosome is less than 1000. In a most preferred aspect of this invention, the number of selected loci measured for each chromosome is at least 48 and less than 1000. In one aspect, following the measurement of abundance for each selected locus, a subset of the selected loci may be used to determine the presence or absence of aneuploidy. There are many standard methods for choosing the subset of selected loci. These methods include outlier exclusion, where the selected loci with detected levels below and/or above a certain percentile are discarded from the analysis. In one aspect, the percentile may be the lowest and highest 5% as measured by abundance. In another aspect, the percentile may be the lowest and highest 10% as measured by abundance. In another aspect, the percentile may be the lowest and highest 25% as measured by abundance.

Another method for choosing the subset of selected loci includes the elimination of regions that fall outside of some statistical limit. For instance, selected loci that fall outside of one or more standard deviations of the mean abundance may be removed from the analysis. Another method for choosing the subset of selected loci may be to compare the relative abundance of a selected locus to the expected abundance of the same selected locus in a healthy population and discard any selected loci that fail the expectation test. To further minimize the variation in the assay, the number of times each selected locus is measured may be increased. As discussed, in contrast to the random methods of detecting aneuploidy where the genome is measured on average less than once, the assay systems of the present invention intentionally measures each selected locus multiple times. In general, when counting events, the variation in the counting is determined by Poisson statistics, and the counting variation is typically equal to one divided by the square root of the number of counts. In a preferred aspect of the invention, the selected loci are each measured on average at least 100 times. In a preferred aspect to the invention, the selected loci are each measured on average at least 500 times. In a preferred aspect to the invention, the selected loci are each measured on average at least 1000 times. In a preferred aspect to the invention, the selected loci are each measured on average at least 2000 times. In a preferred aspect to the invention, the selected loci are each measured on average at least 5000 times.

In another aspect, subsets of loci can be chosen randomly but with sufficient numbers of loci to yield a statistically significant result in determining whether a chromosomal abnormality exists. Multiple analyses of different subsets of loci can be performed within a maternal sample to yield more statistical power. In this example, it may or may not be necessary to remove or eliminate any loci prior to the random analysis. For example, if there are 100 selected loci for chromosome 21 and 100 selected loci for chromosome 18, a series of analyses could be performed that evaluate fewer than 100 loci for each of the chromosomes.

In addition to the methods above for reducing variation in the assay, other analytical techniques, many of which are described earlier in this application, may be used in combination. In general, the variation in the assay may be reduced when all of the loci for each sample are interrogated in a single reaction in a single vessel. Similarly, the variation in the assay may be reduced when a universal amplification system is used. Furthermore, the variation of the assay may be reduced when the number of cycles of amplification is limited.

Determination of Fetal DNA Content in Maternal Sample

In certain specific aspects, determining the relative percentage of fetal DNA in a maternal sample may be beneficial in performing the assays, as it will provide important information on the expected statistical presence of chromosomes and variation from that expectation may be indicative of fetal aneuploidy. This may be especially helpful in circumstances where the level of fetal DNA in a maternal sample is low, as the percent fetal contribution can be used in determining the quantitative statistical significance in the variations of levels of identified loci in a maternal sample. In other aspects, the determining of the relative percent fetal cell free DNA in a maternal sample may be beneficial in estimating the level of certainty or power in detecting a fetal aneuploidy.

In some specific aspects, the relative fetal contribution of maternal DNA at the allele of interest can be compared to the paternal contribution at that allele to determine approximate fetal DNA concentration in the sample. In other specific aspects, the relative quantity of solely paternally-derived sequences (e.g., Y-chromosome sequences or paternally-specific polymorphisms) can be used to determine the relative concentration of fetal DNA in a maternal sample.

Another exemplary approach to determining the percent fetal contribution in a maternal sample through the analysis of DNA fragments with different patterns of DNA methylation between fetal and maternal DNA. In a preferred aspect, the amplified DNA from plasma free DNA is by polymerase chain reaction (PCR). Other mechanisms for amplification can be used as well, including those described in more detail herein, as will be apparent to one skilled in the art upon reading the present disclosure.

In particular aspects, the percentage of free fetal DNA in the maternal sample can determined by PCR using serially diluted DNA isolated from the maternal sample, which can accurately quantify the number of genomes comprising the amplified genes.

In circumstances where the fetus is male, percent fetal DNA in a sample can be determined through detection of Y-specific nucleic acids and comparison to calculated maternal DNA content. Quantities of an amplified Y-specific nucleic acid, such as a region from the sex-determining region Y gene (SRY), which is located on the Y chromosome and is thus representative of fetal DNA, can be determined from the sample and compared to one or more amplified genes which are present in both maternal DNA and fetal DNA and which are preferably not from a chromosome believed to potentially be aneuploid in the fetus, e.g., an autosomal region that is not on chromosome 21 or 18. Preferably, this amplification step is performed in parallel with the selective amplification step, although it may be performed either before or after the selective amplification depending on the nature of the multiplexed assay.

PCR using serially diluted DNA isolated from the maternal sample may be preferred when determining percent fetal DNA with a male fetus. For example, if the blood sample contains 100% male fetal DNA, and 1:2 serial dilutions are performed, then on average the Y-linked signal will disappear 1 dilution before the autosomal signal, since there is 1 copy of the Y-linked gene and 2 copies of the autosomal gene.

In a specific aspect, the percentage of free fetal DNA in maternal plasma is calculated for a male fetus using the following formula: percentage of free fetal DNA=(No. of copies of Y-linked gene×2×100)/(No. of copies of autosomal gene), where the number of copies of each gene is determined by observing the highest serial dilution in which the gene was detected. The formula contains a multiplication factor of 2, which is used to normalize for the fact that there is only 1 copy of the Y-linked gene compared to two copies of the autosomal gene in each genome, fetal or maternal.

Detection of Loci Associated with Pathological Conditions

The assay systems of the invention can be used to identify any loci associated with a disease trait. This includes loci associated with autosomal recessive diseases and disorders, sex linked diseases and disorders, and dominant diseases and disorders.

Autosomal Dominant Disease Traits

A disease trait that is inherited in an autosomal dominant manner can occur in either sex and can be transmitted by either parent. Exemplary diseases that are inherited in an autosomal dominant fashion include, but are not limited to, achondroplasia, Huntington's disease, Familial hypercholesterolemia, Neurofibromatosis Type I, Hereditary spherocytosis, and Marfan syndrome. In addition, many of the cancer predisposition diseases, such as mutations in Rb, p53, and BRCA I and II are inherited in an autosomal dominant fashion.

Autosomal Recessive Disease Traits

Nearly 2000 genes have been identified that are associated with autosomal recessive diseases. Examples of detectable genetic diseases include, but are not limited to, 21 hydroxylase deficiency, cystic fibrosis, phenylketonuria and other inborn errors in metabolism, sickle cell anemia, Tay-Sachs Syndrome, Roberts syndrome, -thalassemia, albinism, adrenal hyperplasia, Fanconi anemia, spinal muscularatrophy, myotonic dystrophy, Angelman syndrome, RhD Syndrome, tuberous sclerosis, Mucopolysaccharidoses, Galactosemia, Glycogen storage diseases, Ataxia-telangiectasia, and Prader-Willi syndrome.

X-Linked Disease Traits

In humans, there are hundreds of genes located on the X chromosome that have no counterpart on the Y chromosome, and the traits governed by these genes thus display X-linked inheritance. Most sex-linked traits are recessively inherited, so that heterozygous females generally do not display the trait. The maternal carrier female (heterozygote) has a 50 percent chance of passing the mutant gene to each of her children, and so sons who inherit the mutant gene will be hemizygotes and will manifest the trait, while daughters who receive the mutant gene will be unaffected carriers. Examples of sex-linked disease traits include, but are not limited to, Hemophilia A, Hemophilia B, Duchenne muscular dystrophy, Becker's muscular dystrophy, X-linked ichthyosis, X-linked agammaglobulinemia (XLA), and color blindness.

Non-Mendelian Inherited Disease Traits

Although disorders resulting from single-gene defects that demonstrate Mendelian inheritance are perhaps better understood, it is now clear that a significant number of single-gene diseases also exhibit distinctly non-Mendelian patterns of inheritance. Among these are such disorders that result from triplet repeat expansions within or near specific genes (e.g., Huntington disease and fragile-X syndrome); a collection of neurodegenerative disorders, such as Leber hereditary optic neuropathy (LHON), that result from inherited mutations in the mitochondrial DNA; and diseases that result from mutations in imprinted genes (e.g., Angelman syndrome and Prader-Willi syndrome).

Blood Group System Traits

In certain preferred aspects of the invention, the assay systems are used to detect a fetal chromosomal abnormality and fetal status of one or more genes of the human blood group systems. The International Society of Blood Transfusion (ISBT) currently recognizes 30 major blood group systems (including the ABO and Rh systems). Thus, in addition to the ABO antigens and Rhesus antigens, many other antigens are expressed on the red blood cell surface membrane. For example, an individual can be AB RhD positive, and at the same time M and N positive (MNS system), K positive (Kell system), and Lea or Leb positive (Lewis system). Many of the blood group systems were named after the patients in whom the corresponding antibodies were initially encountered.

The ISBT definition of a blood group system is where one or more antigens are controlled at a single gene locus or by two or more very closely linked homologous genes with little or no observable recombination between them. See, e.g., ISBT Committee on Terminology for Red Cell Surface Antigens, "Terminology Home Page". A summary of the blood group systems known at the present time are summarized below in Table 1.

TABLE 1

Human Blood Group Systems

| ISBT No. | System name | System symbol | Epitope type | Chromosome |
|---|---|---|---|---|
| 001 | ABO | ABO | Carbohydrate (N-Acetylgalactosamine, galactose). A, B and H antigens. | 9 |
| 002 | MNS | MNS | GPA/GPB (glycophorins A and B). Main antigens M, N, S, s. | 4 |
| 003 | P | P1 | Glycolipid. Antigen P1. | 22 |
| 004 | Rh | RH | Protein. C, c, D, E, e antigens (there is no "d" antigen; lowercase "d" indicates the absence of D). | 1 |
| 005 | Lutheran | LU | Protein (member of the immunoglobulin superfamily). Set of 21 antigens. | 19 |
| 006 | Kell | KEL | Glycoprotein. Kell-1 ($K_1$) | 7 |
| 007 | Lewis | LE | Carbohydrate (fucose residue). Main antigens $Le^a$ and $Le^b$ - associated with tissue ABH antigen secretion. | 19 |
| 008 | Duffy | FY | Protein (chemokine receptor). Main antigens $Fy^a$ and $Fy^b$. | 1 |
| 009 | Kidd | JK | Protein (urea transporter). Main antigens $Jk^a$ and $Jk^b$. | 18 |
| 010 | Diego | DI | Glycoprotein (band 3, AE 1, or anion exchange). | 17 |
| 011 | Yt or Cartwright | YT | Protein (AChE, acetylcholinesterase). | 7 |
| 012 | XG | XG | Glycoprotein. | X |
| 013 | Scianna | SC | Glycoprotein. | 1 |
| 014 | Dombrock | DO | Glycoprotein (fixed to cell membrane by GPI, or glycosyl-phosphatidyl-inositol). | 12 |
| 015 | Colton | CO | Aquaporin 1. Main antigens Co(a) and Co(b). | 7 |
| 016 | Landsteiner-Wiener | LW | Protein (member of the immunoglobulin superfamily). | 19 |
| 017 | Chido/Rodgers | CH/RG | C4A C4B (complement fractions). | 6 |
| 018 | Hh/Bombay | H | Carbohydrate (fucose residue). | 19 |
| 019 | Kx | XK | Glycoprotein. | X |
| 020 | Gerbich | GE | GPC/GPD (Glycophorins C and D). | 2 |
| 021 | Cromer | CROM | Glycoprotein (DAF or CD55, regulates complement fractions C3 and C5, attached to the membrane by GPI). | 1 |
| 022 | Knops | KN | Glycoprotein (CR1 or CD35, immune complex receptor). | 1 |
| 023 | Indian | IN | Glycoprotein (CD44). | 11 |
| 024 | Ok | OK | Glycoprotein (CD147). | 19 |
| 025 | Raph | MER2 | Transmembrane glycoprotein. | 11 |
| 026 | JMH | JMH | Protein (fixed to cell membrane by GPI). | 6 |
| 027 | Ii | I | Branched (I)/unbranched (i) polysaccharide. | 6 |
| 028 | Globoside | GLOB | Glycolipid. Antigen P. | 3 |
| 029 | GIL | GIL | Aquaporin 3. | 9 |
| 030 | Rh-associated glycoprotein | | | |

Hemolytic Disease of the Newborn

The hemolytic condition occurs when there is an incompatibility between the blood types of the mother and the fetus. Multiple different antigen-antibody incompatibilities are implicated as causative, and many of these are preventable or immediately treatable after birth.

The most common cause of severe hemolytic diseases of newborns is a maternal-fetal mismatch in an antigen of the Rh (Rhesus) blood group system (including the Rh factor). The Rh blood group system currently consists of 50 defined blood-group antigens, among which the 5 antigens D, C, c, E, and e are the most clinically relevant. For example, the disorder in the fetus due to Rh D antigen incompatibility is known as erythroblastosis fetalis, and this can be prevented through inoculation of the mother with IgG anti-D (anti-RhD) antibodies that bind to, and lead to the destruction of, fetal Rh D positive red blood cells that have passed from the fetal circulation to the maternal circulation. Therefore, in an Rh-negative mother it can prevent sensitization of the maternal immune system to Rh D antigens, which can cause rhesus disease in the current or in subsequent pregnancies.

Hemolytic disease of the newborn (anti-$Kell_1$) is the second most common cause of severe hemolytic diseases of newborns after Rh disease. Anti-$Kell_1$ is becoming relatively more important as prevention of Rh disease is also becoming more effective. Hemolytic disease of the newborn (anti-$Kell_1$) is caused by a mismatch between the Kell antigens of the mother and fetus. About 91% of the population are $Kell_1$ negative and about 9% are $Kell_1$ positive. A fraction of a percentage are homozygous for $Kell_1$. Therefore, about 4.5% of babies of a $Kell_1$ negative mother are $Kell_1$ positive.

The disease results when maternal antibodies to $Kell_1$ are transferred to the fetus across the placental barrier. These antibodies can cause severe anemia by interfering with the early proliferation of red blood cells as well as causing alloimmune hemolysis. Very severe disease can occur as early as 20 weeks gestation. Hydrops fetalis can also occur early.

Determination of Fetal DNA Content in a Maternal Sample Using Fetal Autosomal Polymorphisms and Genetic Variations In each maternally-derived sample, the DNA from a fetus will have approximately 50% of its loci inherited from the mother and 50% of the loci inherited from the father. Determining the loci contributed to the fetus from paternal sources can allow the estimation of fetal DNA in a maternal sample, and thus provide information used to calculate the statistically significant differences in chromosomal frequencies for chromosomes of interest.

In certain aspects, the determination of fetal polymorphisms requires targeted SNP and/or mutation analysis to identify the presence of fetal DNA in a maternal sample. In some aspects, the use of prior genotyping of the father and mother can be performed. For example, the parents may have undergone such genotype determination for identification of disease markers, e.g., determination of the genotype for disorders such as cystic fibrosis, muscular dystrophy, spinal muscular atrophy or even the status of the RhD gene may be determined. Such difference in polymorphisms, copy number variants or mutations can be used to determine the percentage fetal contribution in a maternal sample.

In one preferred aspect, the percent fetal cell free DNA in a maternal sample can be quantified using multiplexed SNP detection without using prior knowledge of the maternal or paternal genotype. In this aspect, two or more selected polymorphic nucleic acid regions with a known SNP in each region are used. In a preferred aspect, the selected polymorphic nucleic acid regions are located on an autosomal chromosome that is unlikely to be aneuploidy, e.g. Chromosome 2. The selected polymorphic nucleic acid regions from the maternal are amplified. In a preferred aspect, the amplification is universal. In a preferred embodiment, the selected polymorphic nucleic acid regions are amplified in one reaction in one vessel. Each allele of the selected polymorphic nucleic acid regions in the maternal sample is determined and quantified. In a preferred aspect, high throughput sequencing is used for such determination and quantification. Loci are identified where the maternal and fetal genotypes are different, e.g., the maternal genotype is homozygous and the fetal genotype is heterozygous. This identification is done by observing a high relative frequency of one allele (>80%) and a low relative frequency (<20% and >0.15%) of the other allele for a particular selected nucleic acid region. The use of multiple loci is particularly advantageous as it reduces the amount of variation in the measurement of the abundance of the alleles. All or a subset of the loci that meet this requirement are used to determine fetal concentration through statistical analysis. In one aspect, fetal concentration is determined by summing the low frequency alleles from two or more loci together, dividing by the sum of the high frequency alleles and multiplying by two. In another aspect, the percent fetal cell free DNA is determined by averaging the low frequency alleles from two or more loci, dividing by the average of the high frequency alleles and multiplying by two.

For many alleles, maternal and fetal sequences may be homozygous and identical, and as this information is not distinguishing between maternal and fetal DNA it is not useful in the determination of percent fetal DNA in a maternal sample. The present invention utilizes allelic information where there is a distinguishable difference between the fetal and maternal DNA (e.g., a fetal allele containing at least one allele that differs from the maternal allele) in calculations of percent fetal. Data pertaining to allelic regions that are the same for the maternal and fetal DNA are thus not selected for analysis, or are removed from the pertinent data prior to determination of percentage fetal DNA so as not to swamp out the useful data.

Exemplary methods for quantifying fetal DNA in maternal plasma can be found, e.g., in Chu et al., *Prenat Diagn* 2010; 30:1226-1229, which is incorporated herein by reference.

In one aspect, selected nucleic acid regions may be excluded if the amount or frequency of the region appears to be an outlier due to experimental error, or from idiopathic genetic bias within a particular sample. In another aspect, selected nucleic acids may undergo statistical or mathematical adjustment such as normalization, standardization, clustering, or transformation prior to summation or averaging. In another aspect, selected nucleic acids may undergo both normalization and data experimental error exclusion prior to summation or averaging.

In a preferred aspect, 12 or more loci are used for the analysis. In another preferred aspect, 24 or more loci are used for the analysis. In another preferred aspect, 48 or more loci are used for the analysis. In another aspect, one or more indices are used to identify the sample, the locus, the allele or the identification of the nucleic acid.

In one preferred aspect, the percentage fetal contribution in a maternal sample can be quantified using tandem SNP detection in the maternal and fetal alleles. Techniques for identifying tandem SNPs in DNA extracted from a maternal sample are disclosed in Mitchell et al, U.S. Pat. No. 7,799,531 and U.S. patent application Ser. Nos. 12/581,070, 12/581,083, 12/689,924, and 12/850,588. These describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

Determination of Fetal DNA Content in a Maternal Sample Using Epigenetic Allelic Ratios Certain genes have been identified as having epigenetic differences between the placenta and maternal blood cells, and such genes are candidate loci for fetal DNA markers in a maternal sample. See, e.g., Chim S S C, et al. *Proc Natl Acad Sci USA* (2005); 102:14753-14758. These loci, which are unmethylated in the placenta but not in maternal blood cells, can be readily detected in maternal plasma and were confirmed to be fetus specific. Unmethylated fetal DNA can be amplified with high specificity by use of methylation-specific PCR (MSP) even when such fetal DNA molecules were present among an excess of background plasma DNA of maternal origin. The comparison of methylated and unmethylated amplification products in a maternal sample can be used to quantify the percent fetal DNA contribution to the maternal sample by calculating the epigenetic allelic ratio for one or more of such sequences known to be differentially regulated by methylation in the fetal DNA as compared to maternal DNA.

To determine methylation status of nucleic acids in a maternal sample, the nucleic acids of the sample are subjected to bisulfite conversion of the samples and then subjected them to MSP, followed by allele-specific primer extension. Conventional methods for such bisulphite conversion include, but are not limited to, use of commercially available kits such as the Methylamp™ DNA Modification Kit (Epigentek, Brooklyn, N.Y.). Allelic frequencies and ratios can be directly calculated and exported from the data to determine the relative percentage of fetal DNA in the maternal sample.

Use of Percent Fetal Cell Free DNA to Detect Aneuploidy

Once the percent fetal cell free DNA has been calculated, this data may be combined with methods for aneuploidy detection to determine the likelihood that a maternal sample may contain an aneuploidy. In one aspect, an aneuploidy detection methods that utilizes analysis of random DNA segments is used, such as that described in, e.g., Quake, U.S. patent application Ser. No. 11/701,686; Shoemaker et al., U.S. patent application Ser. No. 12/230,628. In a preferred aspect, aneuploidy detection methods that utilize analysis of selected nucleic acid regions is used. In this aspect, the percent fetal cell free DNA for a sample is calculated. The chromosomal ratio for that sample, a chromosomal ratio for the normal population and a variation for the chromosomal ratio for the normal population is determined, as described herein. In one preferred aspect, the chromosomal ratio and its variation for the normal population are determined from normal samples that have a similar percentage of fetal DNA. An expected aneuploidy chromosomal ratio for a DNA sample with that percent fetal cell free DNA is calculated by adding the percent contribution from the aneuploidy chromosome. The chromosomal ratio for the sample may then be compared to the chromosomal ratio for the normal population and to the expected aneuploidy chromosomal ratio to determine statistically, using the variation of the chromosomal ratio, to determine if the sample is more likely normal or aneuploidy, and the statistical probability that it is one or the other.

In a preferred aspect, the selected regions of a maternal sample include both regions for determination of fetal DNA content as well as non-polymorphic regions from two or more chromosomes to detect a fetal chromosomal abnormality in a single reaction. The single reaction helps to minimize the risk of contamination or bias that may be introduced during various steps in the assay system which may otherwise skew results when utilizing fetal DNA content to help determine the presence or absence of a chromosomal abnormality.

In other aspects, a selected region or regions may be utilized both for determination of fetal DNA content as well as detection of fetal chromosomal abnormalities. The alleles for selected regions can be used to determine fetal DNA content and these same selected regions can then be used to detect fetal chromosomal abnormalities ignoring the allelic information. Utilizing the same regions for both fetal DNA content and detection of chromosomal abnormalities may further help minimize any bias due to experimental error or contamination.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: General Aspects of the Assay Systems of the Invention

A number of assay formats were tested to demonstrate the ability to perform selective amplification and detection of independent loci to demonstrate multiplexed, ligation-based detection of a large number (e.g., 96 or more) of loci of interest. These loci included loci that were indicative of the presence of a particular chromosome or the presence or absence of a mutation or polymorphism in a particular allele.

These assays were designed based on human genomic sequences, and each interrogation consisted of two fixed sequence oligos per selected locus interrogated in the assay. The first oligo, complementary to the 3' region of a genomic region, comprised the following sequential (5' to 3') oligo elements: a universal PCR priming sequence common to all assays:

(SEQ ID NO: 1)
TACACCGGCGTTATGCGTCGAGAC;

a nine nucleotide identification index specific to the selected locus; a 9 base locus- or locus/allele-specific sequence that acts as a locus index in the first SNP-independent set and a locus/allele index in the polymorphism-specific second set; a hybridization breaking nucleotide which is different from the corresponding base in the genomic locus; and a 20-24 bp sequence complementary to the selected genomic locus. In cases where a SNP or mutation was detected in this portion of the selected genomic locus, the allele-specific interrogation set consisted of two first fixed sequence tandem ligation primers, each with a different locus/allele index and a different allele-specific base at the SNP position. These first oligos were designed for each selected nucleic acid to provide a predicted uniform $T_m$ with a two degree variation across all interrogations in the assay set.

The second fixed sequence oligo, complementary to the 5' region of the genomic loci, comprised the following sequential (5' to 3') elements: a 20-24b sequence complimentary to the 5' region in the genomic locus; a hybridization breaking nucleotide different from the corresponding base in the genomic locus; and a universal PCR priming sequence which was common to all third oligos in the assay set:

(SEQ ID NO: 2)
ATTGCGGGGACCGATGATCGCGTC.

In cases where a SNP or mutation was detected in the selected genomic locus, the allele-specific interrogation set consisted of two tandem ligation primers, each with a different locus/allele index and a different allele-specific base at the mutation/SNP position. This second fixed sequence oligo was designed for each selected nucleic acid to provide a predicted uniform $T_m$ with a two degree variation across all interrogations in the assay set that was substantially the same $T_m$ range as the first oligo set.

In certain tested aspects, one or more bridging oligos were used that were complementary to the genomic locus sequence between the region complementary to the first and second fixed sequence oligos used for each selected locus. In specific aspects tested, more than one bridging oligo was used to span the gap between the fixed sequence oligonucleotides, and the one or more bridging oligo may optionally be designed to identify one or more mutations or SNPs in the sequence. The length of the bridging oligonucleotides used in the assay systems varied from 5 to 36 base pairs.

All oligonucleotides used m the tandem ligation formats were synthesized using conventional solid-phase chemistry. The second fixed sequence oligos and the bridging oligonucleotides were synthesized with 5' phosphate moieties to enable ligation to 3' hydroxyl termini of adjacent oligonucleotides.

Example 2: Preparation of DNA for Use in Tandem Ligation Procedures

Genomic DNA from a Caucasian male (NA12801) or a Caucasian female (NA11995) was obtained from Coriell Cell Repositories (Camden, N.J.) and fragmented by acoustic shearing (Covaris, Woburn, Mass.) to a mean fragment size of approximately 200 bp.

The Coriell DNA was biotinylated using standard procedures. Briefly, the Covaris fragmented DNA was end-repaired by generating the following reaction in a 1.5 ml microtube: 5 µg DNA, 12 µl 10× T4 ligase buffer (Enzymatics, Beverly Mass.), 50 U T4 polynucleotide kinase (Enzymatics, Beverly Mass.), and $H_2O$ to 120 µl. This was incubated at 37° C. for 30 minutes. The DNA was diluted using 10 mM Tris 1 mM EDTA pH 8.5 to desired final concentration of ~2 ng/µl.

5 µl DNA was placed in each well of a 96-well plate, and the plate sealed with an adhesive plate sealer and spun for 10 seconds at 250×g. The plate was then incubated at 95° C. for 3 minutes, cooled to 25° C., and spun again for 10 seconds at 250×g. A biotinylation master mix was prepared in a 1.5 ml microtube to final concentration of: 1× TdT buffer (Enzymatics, Beverly, Mass.), 8 U TdT (Enzymatics, Beverly, Mass.), 250 µM $CoCl_2$, 0.01 nmol/µl biotin-16-dUTP (Roche, Nutley N.J.), and $H_2O$ to 1.5 ml. 15 µl of the master mix was aliquoted into each well of a 96 well plate, and the plate sealed with adhesive plate sealer. The plate was spun for 10 seconds at 250×g and incubated for 37° C. for 60 minutes. Following incubation, the plate was spun again for 10 seconds at 250×g, and 7.5 µl precipitation mix (1).µg/µl Dextran Blue, 3 mM NaOAC) was added to each well.

The plate was sealed with an adhesive plate sealer and mixed using an IKA plate vortexer for 2 minutes at 3000 rpm. 27.5 µl of isopropanol was added into each well, the plate sealed with adhesive plate sealer, and vortexed for 5 minutes at 3000 rpm. The plate was spun for 20 minutes at 3000×g, the supernatant was decanted, and the plate inverted and centrifuged at 10×g for 1 minute onto an absorbent wipe. The plate was air-dried for 5 minutes, and the pellet resuspended in 30 µl 10 mM Tris pH8.0, 1 mM EDTA.

Example 3: Exemplary Assay Formats Using Tandem Ligation

Numerous tandem ligation assay formats using the biotinylated DNA were tested to illustrate proof of concept for the assay systems of the invention, and demonstrated the ability to perform highly multiplexed, targeted detection of a large number of independent loci using the series of different assay formats. The exemplary assay systems of the invention were designed to comprise 96 or more interrogations per loci in a genetic sample, and in cases where SNPs were detected the assay formats utilized 192 or more separate interrogations, each utilizing the detection of different alleles per 96 loci in genetic samples. The examples described for each assay format utilized two different sets of fixed sequence oligonucleotides and/or bridging oligos (as described in Example 1), comprising a total 96 or 192 interrogation reactions for the selected loci depending upon whether or not SNPs were identified.

A first exemplary assay format used locus-specific fixed sequence oligos and bridging oligos, where there was a one base gap between the first fixed sequence oligo and the bridging oligos, and a second one base gap between the bridging oligos and the second fixed sequence oligo. Each of the two gaps encompassed two different SNPs. In this format, a DNA polymerase was used to incorporate each of the SNP bases, and ligase was used to seal the nicks formed thereby. SNP base discrimination derived from the fidelity of base incorporation by the polymerase, and in the event of mis-incorporation, the tendency of ligase to not seal nicks adjacent to mismatched bases.

The second exemplary assay format used two locus-specific fixed sequence oligonucleotides without a bridging oligo, where there was a 15-35 base gap between the fixed sequence oligos, and where the gap spanned one or more SNPs. In this format, a polymerase was used to incorporate the missing bases of the gap, and a ligase was used to seal the nick formed thereby. SNP base discrimination derived from the fidelity of base incorporation by the polymerase, and in the event of misincorporation, the tendency of ligase to not seal nicks adjacent to mismatched bases.

A third exemplary assay format used allele-specific first and second fixed sequence oligos without a bridging oligo, where there was a 15-35 base gap between the first and second fixed sequence oligos, and where the gap spanned one or more SNPs. Two separate allele-specific first fixed sequence oligos and two separate allele-specific second fixed sequence oligos were used. A polymerase was used to incorporate the missing bases, and a ligase was used to seal the nick formed thereby. SNP base discrimination derived from hybridization specificity, the tendency of non-proofreading polymerase to not extend annealed primers with mismatches near the 3' end, and the tendency of the ligase to not seal nicks adjacent to mismatched bases.

A fourth exemplary format used allele-specific fixed sequence oligos and a locus-specific bridging oligo. In this format, two separate fixed sequence oligos complementary to the 3'end of the loci of interest, the first with a 3' base specific for one allele of the targeted SNP, and the second with a 3' base specific for the other allele of the targeted SNP. Similarly, two separate second fixed sequence oligos were used, the first with a 5' base specific for one allele of a second targeted SNP, and the second with a 5' base specific for the other allele of the second targeted SNP. The bridging oligos were complementary to the region directly adjacent to the locus regions complementary to the first and second fixed sequence oligos, and thus no polymerase was needed prior to ligation. Ligase was used to seal the nicks between the fixed sequence oligos and the bridging oligo. SNP base discrimination in this assay format derived from hybridization specificity and the tendency of the ligase to not seal nicks adjacent to mismatched bases. This exemplary format was tested using either T4 ligase or Taq ligase for creation of the contiguous template, and both were proved effective in the reaction as described below.

A fifth exemplary format used locus-specific fixed sequence oligos that were complementary to adjacent regions on the nucleic acid of interest, and thus no gap was created by hybridization of these oligos. In this format, no polymerase was required, and a ligase was used to seal the single nick between the oligos.

A sixth exemplary format used allele-specific fixed sequence oligos and locus-specific bridging oligos, where there was a short base gap of five bases between the loci region complementary to the fixed sequence oligos. The locus-specific bridging oligo in this example was a 5mer complementary to the regions directly adjacent to the regions complementary to the first and second fixed sequence oligos. In this format, no polymerase was required, and a ligase was used to seal the two nicks between the oligos.

A seventh exemplary format used locus-specific fixed sequence oligos and a locus-specific bridging oligo, where there was a shorter base gap of five bases containing a SNP in the region complementary to the bridging oligo. Allele-specific bridging oligos corresponding to the possible SNPs were included in the hybridization and ligation reaction. In this format, no polymerase was required, and a ligase was used to seal the two nicks between the oligos. SNP base discrimination in this assay format derived from hybridization specificity and the tendency of the ligase to not seal nicks adjacent to mismatched bases.

An eighth exemplary format used locus-specific fixed sequence oligos and two adjacent locus-specific bridging oligos, where there was a 10 base gap between the regions complementary to the first and second fixed sequence oligos. Locus-specific bridging oligos were included in the ligation reaction, with the gap requiring two contiguous 5mers to bridge the gap. In this format, no polymerase was required, and a ligase was used to seal the three nicks between the oligos.

For each of the above-described assay formats, an equimolar pool (40 nM each) of sets of first and second loci- or allele-specific fixed sequence oligonucleotides was created from the oligos prepared as set forth in Example 2. A separate equimolar pool (20 µM each) of bridging oligonucleotides was likewise created for the assay processes based on the sequences of the selected genomic loci.

100 µg of streptavidin beads were transferred into the wells of a 96 well plate, and the supernatant was removed. 60 µl BB2 buffer (100 mM Tris pH 8.0, 10 mM EDTA, 500 mM NaCl$_2$, 58% formamide, 0.17% Tween-80), 10 µL 40 nM fixed sequence oligo pool and 30 µL of the biotinylated template DNA prepared in Example 2 were added to the beads. The plate was sealed with an adhesive plate sealer and vortexed at 3000 rpm until beads were resuspended. The oligos were annealed to the template DNA by incubation at 70° C. for 5 minutes, followed by slow cooling to room temperature.

The plate was placed on a raised bar magnetic plate for 2 minutes to pull the magnetic beads and associated DNA to the side of the wells. The supernatant was removed by pipetting, and was replaced with 50).11 of 60% BB2 (v/v in water). The beads were resuspended by vortexing, placed on the magnet again, and the supernatant was removed. This bead wash procedure was repeated once using 50 µl 60% BB2, and repeated twice more using 50 µl wash buffer (10 mM Tris pH 8.0, 1 mM EDTA, 50 mM NaCl$_2$).

The beads were resuspended in 37 µl ligation reaction mix consisting of IX Taq ligase buffer (Enzymatics, Beverly, Mass.), 1UTaq ligase, and 2 µM bridging oligo pool (depending on the assay format), and incubated at 37° C. for one hour. Where appropriate, and depending on the assay format, a non-proofreading thermostable polymerase plus 200 nM each dNTP was included in this mixture. The plate was placed on a raised bar magnetic plate for 2 minutes to pull the magnetic beads and associated DNA to the side of the wells. The supernatant was removed by pipetting, and was replaced with 50 µL wash buffer. The beads were resuspended by vortexing, placed on the magnet again, and the supernatant was removed. The wash procedure was repeated once.

To elute the products from the streptavidin beads, 30 µl of 10 mM Tris 1 mM EDTA, pH 8.0 was added to each well of 96-well plate. The plate was sealed and mixed using an IKA vortexer for 2 minutes at 3000 rpm to resuspend the beads. The plate was incubated at 95° C. for 1 minute, and the supernatant aspirated using an 8-channel pipetter. 25 µl of supernatant from each well was transferred into a fresh 96-well plate for universal amplification.

Example 4: Universal Amplification of Tandem Ligated Products

The polymerized and/or ligated nucleic acids were amplified using universal PCR primers complementary to the universal sequences present in the first and second fixed sequence oligos hybridized to the loci of interest. 25 µl of each of the reaction mixtures of Example 3 were used in each amplification reaction. A 50 µl universal PCR reaction consisting of 25 µl eluted ligation product plus IX Pfusion buffer, 1M Betaine, 400 nM each dNTP, 1 U Pfusion error-correcting thermostable DNA polymerase (Thermo Fisher, Waltham Mass.), and the following primer pairs:

```
                                              (SEQ ID NO: 3)
TAATGATACGGCGACCACCGAGATCTACACCGGCGTTATGCGTCGAGA
and
                                              (SEQ ID NO: 4)
TCAAGCAGAAGACGGCATACGAGATXAAACGACGCGATCATCGGTCCCCG

CAA,
``` where X represents one of 96 different sample indices used to uniquely identify individual samples prior to pooling and sequencing. The PCR was carried out under stringent conditions using a BioRad Tetrad™ thermocycler.

10 µl of universal PCR product from each of the samples were pooled and the pooled PCR product was purified using AMPureXP™ SPRI beads (Beckman-Coulter, Danvers, Mass.), and quantified using Quant-iT™ PicoGreen, (Invitrogen, Carlsbad, Calif.).

Example 5: Detection and Analysis of Selected Loci

The purified PCR products of each assay format were sequenced on a single lane of a slide on an Illumina HiSeq™ 2000 (Illumina, San Diego, Calif.). Sequencing runs typically give rise to ~100M raw reads, of which ~85M (85%) mapped to expected assay structures. This translated to an average of ~885K reads/sample across the experiment, and (in the case of an experiment using 96 loci) 9.2K reads/replicate/locus across 96 loci. The mapped reads were parsed into replicate/locus/allele counts, and various metrics were computed for each condition, including:

Yield: a metric of the proportion of input DNA that was queried in sequencing, computed as the average number of unique reads per locus (only counting unique identification index reads per replicate/locus) divided by the total number of genomic equivalents contained in the input DNA.

80 percentile locus frequency range: a metric of the locus frequency variability in the sequencing data, interpreted as the fold range that encompasses 80% of the loci. It was computed on the distribution of total reads per locus, across all loci, as the 90th percentile of total reads per locus divided by the $10^{th}$ percentile of the total reads per locus.

SNP error rate: a metric of the error rate at the SNP position, and computed as the proportion of reads containing a discordant base at the SNP position.

These results are summarized in Table 2:

TABLE 2

Results Summary of Tandem Ligation Assay Formats

| ASSAY FORMAT | FIXED SEQUENCE OLIGO ($1^{st}$ and/or $2^{nd}$) | BRIDGING OLIGO USED | ENZYME USED | YIELD | 80% LOC FREQ RANGE | SNP ERROR RATE |
|---|---|---|---|---|---|---|
| 1 | LOCUS-SPECIFIC | Locus specific | pol + lig | 9.5% | 5.3 | 0.18% |
| 2 | LOCUS-SPECIFIC | No | pol + lig | 1.4% | 58.3 | 0.19% |
| 3 | ALLELE-SPECIFIC | No | pol + lig | 0.4% | 61.7 | 1.00% |
| 4 | ALLELE-SPECIFIC | Locus specific | Taq lig | 5.0% | 5.9 | 0.92% |
| 4 | ALLELE-SPECIFIC | Locus specific | T4 lig | 5.3% | 4.4 | 0.95% |
| 5 | LOCUS-SPECIFIC | No | Taq lig | 22.5% | 1.7 | NA |
| 6 | LOCUS-SPECIFIC | Locus specific | Taq lig | 12.5 | 2.9 | NA |
| 7 | LOCUS-SPECIFIC | Allele specific | Taq lig | 14.3 | 2.8 | 0.20% |
| 8 | LOCUS-SPECIFIC | 2 Locus specific | Taq lig | 18.5% | 2.8 | NA |

Table 2 indicates that the locus-specific tandem ligation assay using a bridging oligo converted template DNA into targeted product with high yield (10%), with a high proportion of product derived from targeted loci (15% of reads did not contain expected assay structures), with limited locus bias (80% of loci fall within a 5-fold concentration range), and with high SNP accuracy (0.2% SNP error rate). The locus-specific tandem ligation assay without the use of a bridging oligo produced reduced yields and substantial locus bias, but still produced high accuracy SNP genotyping data. The allele-specific tandem ligation assay with a bridging oligo produced intermediate yields compared to the locus-specific assay using both T4 and Taq ligase, but still produced limited locus bias and high accuracy SNP genotyping data. The allele-specific tandem ligation assay without a bridging produced reduced yields and substantial locus bias, but still produced high accuracy SNP genotyping data.

Figure 5:
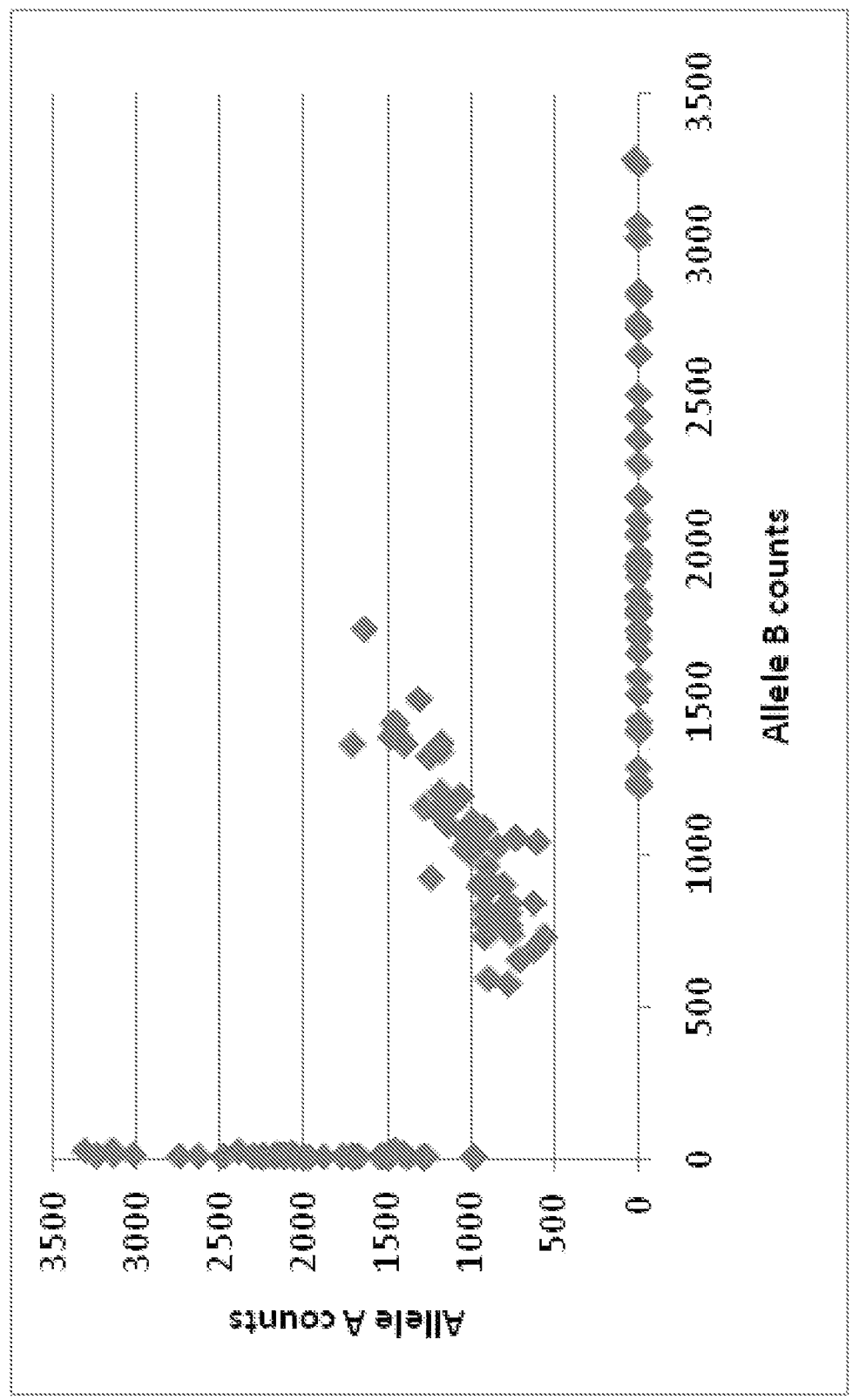
FIG. 5 illustrates the genotyping performance that was obtained using one assay system of the invention.

Assay formats six through eight showed that template DNA can be converted into targeted product with high yield (12-18%), with a high proportion of product derived from targeted loci (76% of reads contained expected assay structures), and with limited locus bias (80% of loci fall within a 2-3-fold concentration range). FIG. 5 illustrates the genotyping performance that was obtained using assay format seven, comparing the sequence counts for the two alleles of all polymorphic assays observed in a single sample. Note the clear separation of the homozygous and heterozygous clusters, as well as the low background counts observed amongst the homozygous clusters.

Example 6: Detection of Aneuploidy in Patient Samples from Pregnant Subjects The assay systems of the invention were used in the detection of polymorphisms and chromosomal abnormalities in two separate cohorts of pregnant females. A first cohort of 190 normal, 36 T21, and 8 T18 pregnancies and a second cohort of 126 normal, 36 T21, and 8 T18 pregnancies were tested for fetal aneuploidy. The chromosomal aneuploidies were detected using 576 chromosome 21 and 576 chromosome 18 assays, pooled together and assayed in a single reaction, as set forth below.

Figure 6:
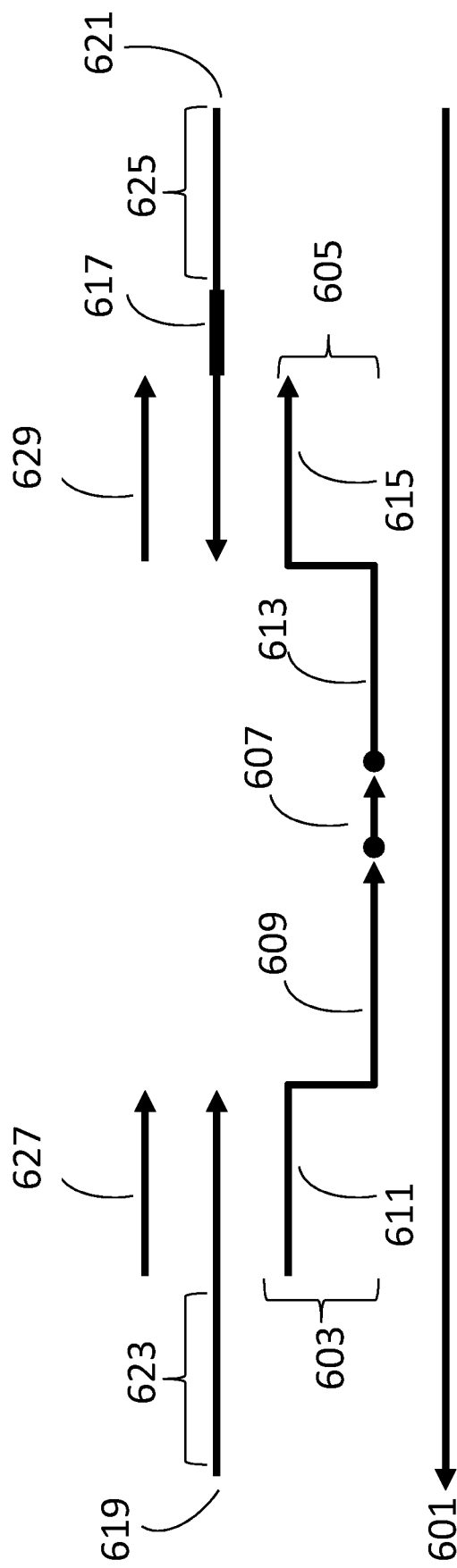
FIG. 6 illustrates the elements used for a detection of aneuploidy and polymorphism for two cohorts of maternal samples.

The elements used in the aneuploidy detection assays are illustrated in FIG. 6. The cfDNA 601 isolated from maternal samples was used as a template for hybridization, ligation, and amplification of multiple selected loci from both chromosome 21 and chromosome 18 in each maternal sample. Three oligonucleotides were hybridized to each selected locus to create ligation products for amplification and detection. The left (or first) fixed sequence oligonucleotide comprised a region complementary to a selected locus 609 and a first universal primer region 611. The right (or second) fixed sequence oligonucleotide 605 comprised a second region complementary to the selected locus 613 and a second universal primer region 615. The bridging oligonucleotides 607 used were designed so that each would hybridize to bridging regions of two or more selected loci used in the aneuploidy detection assay. When the fixed sequence oligonucleotides 603, 605 and the bridging oligonucleotide 607 hybridized to the complementary region on the cfDNA 601, their termini formed two nicks. Upon ligation of the hybridized oligonucleotides to the cfDNA, a ligation product was created for each selected locus comprising 603, 605 and 607 which was used as a template for amplification primers 619, 621.

Two amplification primers 619, 621 comprising regions complementary to the first and second universal primer regions, respectively, were then used to amplify the ligation product. This amplification product comprised the sequence of the selected locus. The right amplification primer also comprised a sample index 617 to identify the particular sample from which the locus was obtained in the multiplexed assay. Amplification with 96 distinct right amplification primers 629 enabled pooling and simultaneous sequencing of 96 different amplification products on a single lane.

The amplification primers 619, 621 also contained a left cluster sequence 623

(SEQ ID NO: 7)
(TAATGATACGGCGACCACCGA)

and a right cluster sequence 625

(SEQ ID NO: 8)
(ATCTCGTATGCCGTCTTCTGCTTGA)

that supported cluster amplification for sequencing using the Illumina HiSeq™ 2000 system (Illumina, San Diego, Calif.). A sequencing primer 627 comprising the first universal primer sequence was used to determine the sequence of the amplification product, and a second sequencing primer 629 was used to determine the sample index 617 of the amplification product.

Briefly, approximately 10 mL peripheral blood was collected from each patient into a BCT tube (Streck, Omaha, Nebr.), which was shipped via overnight courier to Tandem Diagnostics. Plasma was isolated from BCT tubes within 72 h of blood collection by centrifugation at 1600 g for 10 m. The plasma was transferred to a second tube and centrifuged at 16000 g for 10 m to remove any remaining cells. cfDNA was isolated from 4-5 mL plasma per patient. Approximately 15 ng cfDNA was isolated from each patient sample and arrayed into individual wells of a 96 well plate. All subsequent processing occurred on multiplexed batches of up to 96 cfDNA patient samples per array system method.

cfDNA isolated from the maternal samples in each well was biotinylated precipitated and resuspended in 30 uL TE as in Example 3 above. The biotinylated template DNA was mixed with 100 ug MyOneC1 streptavidin-coated magnetic beads (Life Technologies, Carlsbad, Calif.), 60 µl BB2 buffer (100 mM Tris pH 8.0, 10 mM EDTA, 500 mM $NaCl_2$, 58% formamide, 0.17% Tween-80), and 10 µL of pooled 40 nM left 603 and right 605 fixed sequence oligonucleotides. The mixture was heated to 70° C., and cooled 2 hours. The beads were then magnetically immobilized to the side of the well, washed twice with 50 uL 60% BB2 (v/v with H20), washed twice more with 50 µl wash buffer (10 mM Tris pH 8.0, 1 mM EDTA, 50 mM NaCl2), and then resuspended in a 50 µL reaction containing 1 U Taq ligase (Enzymatics, Beverly Mass.), IX Taq ligase buffer (Enzymatics), and 10 uM of a 5'-phosphorylated 5mer bridging oligonucleotide 607. The mixture was incubated at 37° C. for 1 hour. The beads were again magnetically immobilized to the side of the well, washed twice with 50 uL wash buffer and then resuspended in 30 µL TE.

The ligation products were eluted from the immobilized beads by incubation at 95° C. for 3 minutes. The eluted ligation products were amplified by 26 cycles of PCR in a 50 uL reaction containing 1 U Pfusion (Finnzymes), 1M Betaine, IX Pfusion buffer, and 400 nM left and right amplification primers (619, 621 respectively). The right primer contained a 7 base sample index (617) that enabled 96 sample multiplexed sequencing on the HiSeq2000 (Illumina, San Diego, Calif.). The sequence of the left fixed sequence oligo was:

(SEQ ID NO: 5)
TAATGATACGGCGACCACCGAGATCTACACCGGCGTTATGCGTCGAGAC

And the sequence of the right fixed sequence oligo was:

(SEQ ID NO: 6)
TCAAGCAGAAGACGGCATACGAGATNNNNNNNAAACGACGCGATCATCGG
TCCCCGCAAT

Amplification products from a single 96 well plate were pooled in equal volume, and the pooled amplification products were purified with AMPureXP™ SPRI beads (Beckman-Coulter, Danvers, Mass.) according to the manufacturer's instructions. Each purified pooled library was used as template for cluster amplification on an Illumina TruSeq v2 SR cluster kit flow cell (Illumina, San Diego, Calif.) according to manufacturer's protocols. The slide was processed on an Illumina HiSeq™ 2000 (Illumina, San Diego, Calif.) to produce 56 bases of locus-specific sequence from a left sequence primer 623 and a separate read of 8 bases of sample specific sequence was obtained from the second sequence primer 625. An average of 903K raw reads per sample were collected. An average of 876K (97%) of the reads was assigned to expected assay structures.

FIG. 7 shows exemplary data for a subset of the patient samples from the second cohort, which were all analyzed in one multiplexed assay on a single lane of a sequencing run. Initially 96 different samples were run in this particular run, but—six samples were later excluded from this analytical set as not meeting sample quality control thresholds.

A trimmed mean was calculated for each chromosome 18 and chromosome 21 for the samples based on reads produced in the assay. The trimmed mean was computed by removing 10% of high and low counts for each chromosome by sample. The detected amplification products corresponding to the various selected loci were used to compute a chromosome 21 proportion metric and a chromosome 18 proportion metric for each sample. For chromosome 21 proportion, this was calculated as the trimmed mean of counts in the 384 chromosome 21 selected loci divided by the sum of trimmed means of counts for all 576 chromosome 21 loci and 576 chromosome 18 loci for each sample.

On average 834 read counts were observed per selected locus in the maternal samples of the first cohort, and 664 read counts were observed per selected locus from the second cohort. These counts were used to compute chromosome proportion z-scores for chromosome 21 and chromosome 18.

Briefly, the z-scores were calculated by scaling the median per locus count to a common value (e.g., 1000) for each sample, and the scaled counts were transformed by log base 2. An RMA log linear modeling and median polish were performed (Bolstad, B. M et al. (2003) *Bioinformatics* 19(2):185-193; Rafael. A. (2003) *Nucleic Acids Research* 31(4):e15; Irizarry, R A et al. (2003) *Biostatistics* 4(2):249-64) to estimate chromosome effects, locus effects, sample effects, and residuals. The estimated chromosome effects were set to a common value, e.g., 0, and 2 A (chromosome effect+sample effect+residual) was calculated for each locus to create normalized counts. The Z scores were scaled using iterative censoring so that they had a mean of 0 and a standard deviation of 1.

Figure 8:
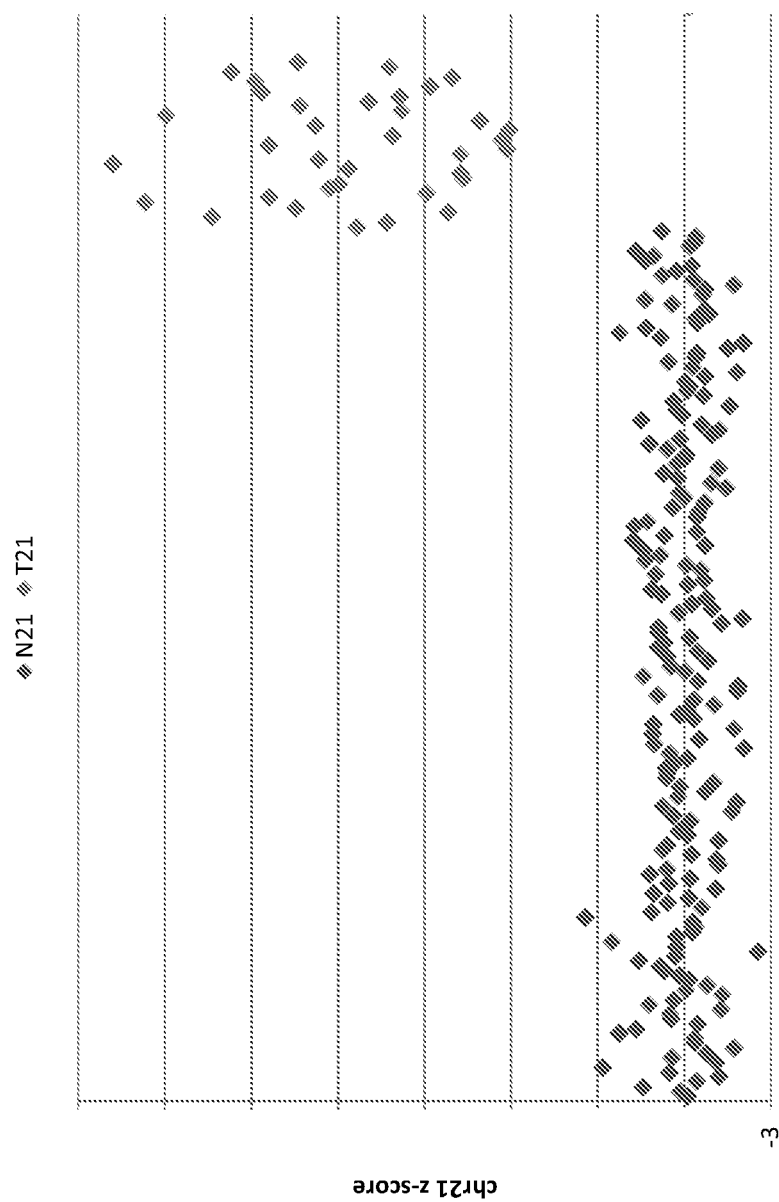
FIG. 8 illustrates the chromosome 21 aneuploidy detection achieved using one aspect of the invention for a first cohort.
Figure 9:
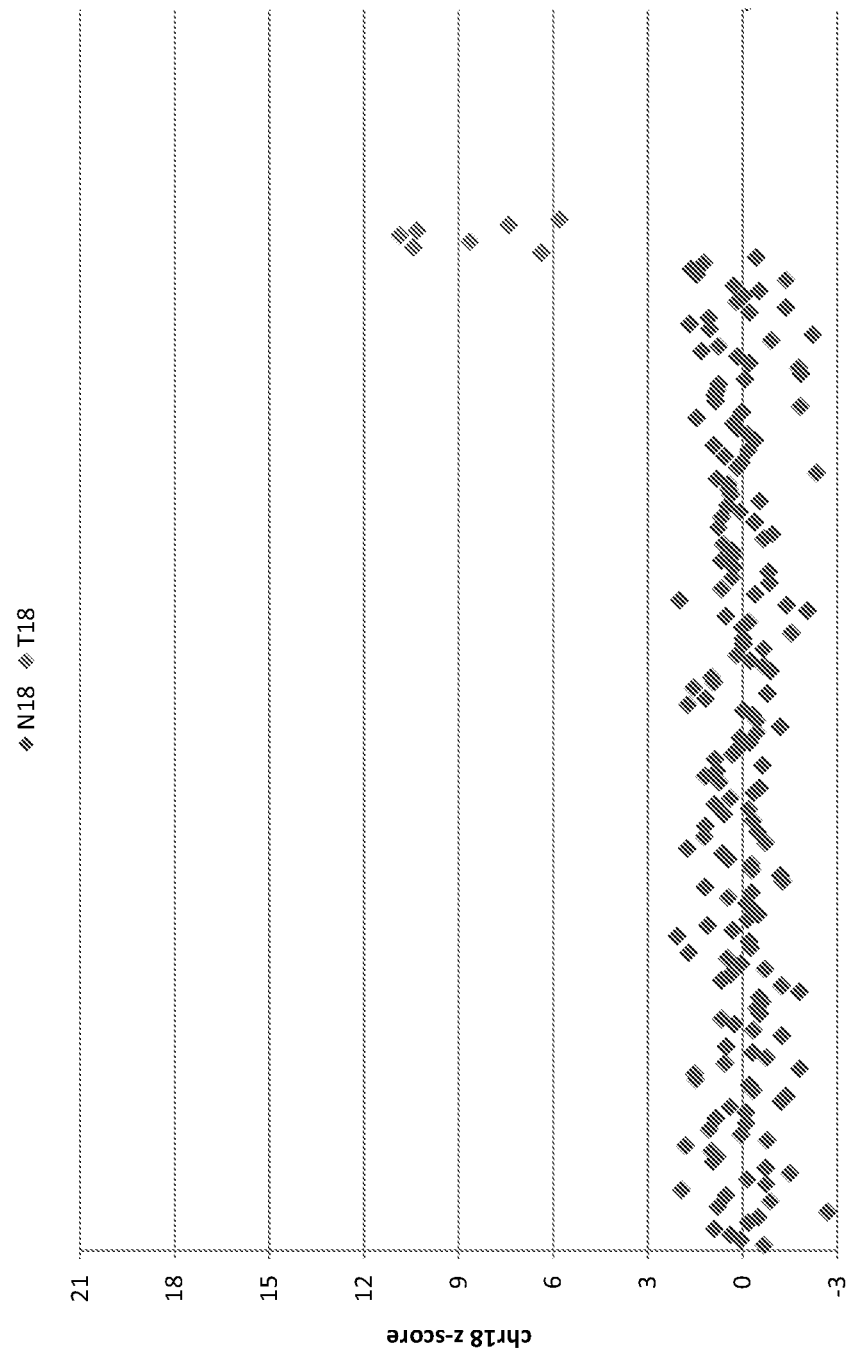
FIG. 9 illustrates the chromosome 18 aneuploidy detection achieved using one aspect of the invention for a first cohort.

Data obtained from the first cohort of samples was used to determine first cohort z-scores for chromosome 21 and chromosome 18 are illustrated in FIGS. 8 and 9, respectively. The normal samples are shown as dark grey diamonds, and the samples with a trisomy are shown as light grey diamonds. 179/180 (99.4%) normal samples (dark grey diamonds) had z-scores <3; one normal sample had a chromosome 21 z-score of 3.4 and a chromosome 18 z-score of 3.0. 35/35 (100%) T21 and 7/7 (100%) T18 samples had chromosome proportion z-scores >3. The mean T18 z-score was 8.5, and the range was 5.8-10.9. The mean T21 z-score was 11.5, and the range was 6.1-19.8.

Figure 10:
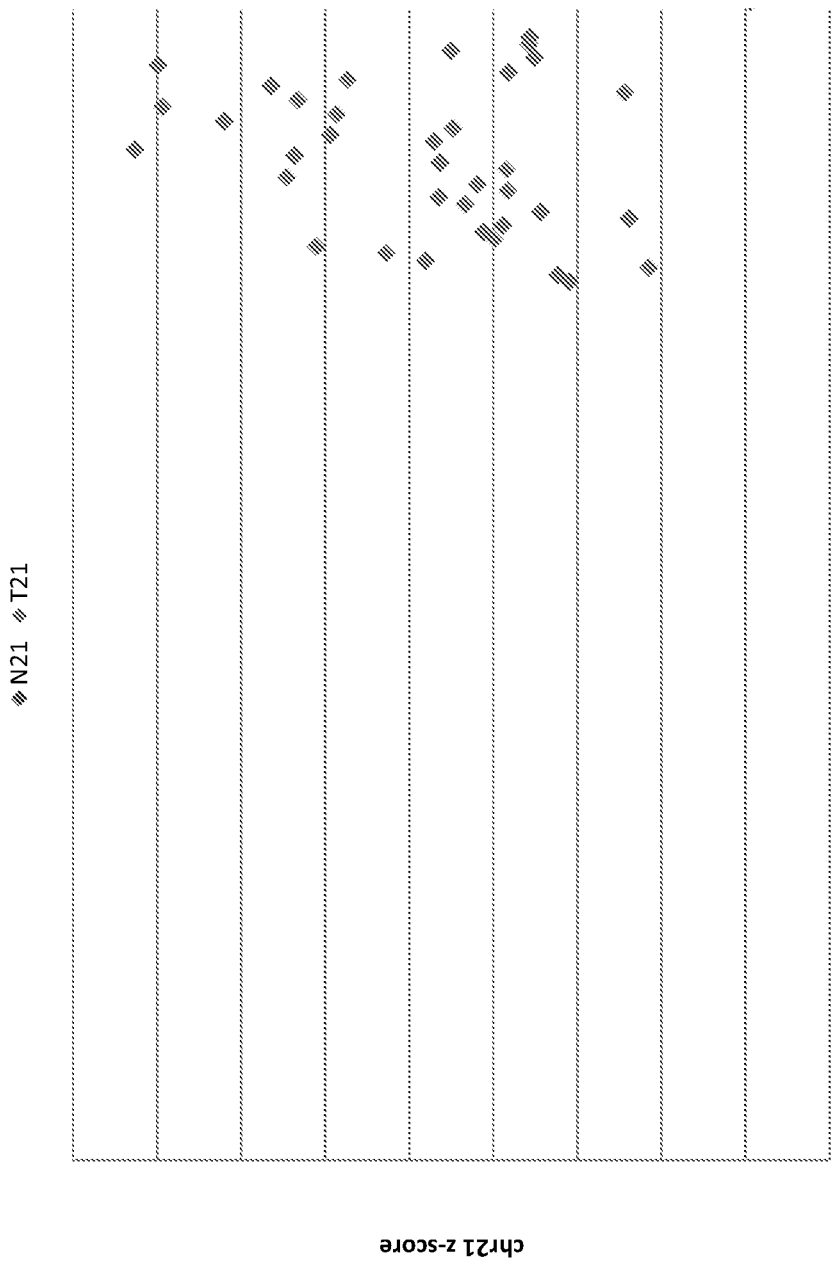
FIG. 10 illustrates the chromosome 21 aneuploidy detection achieved using one aspect of the invention for a second cohort.
Figure 11:
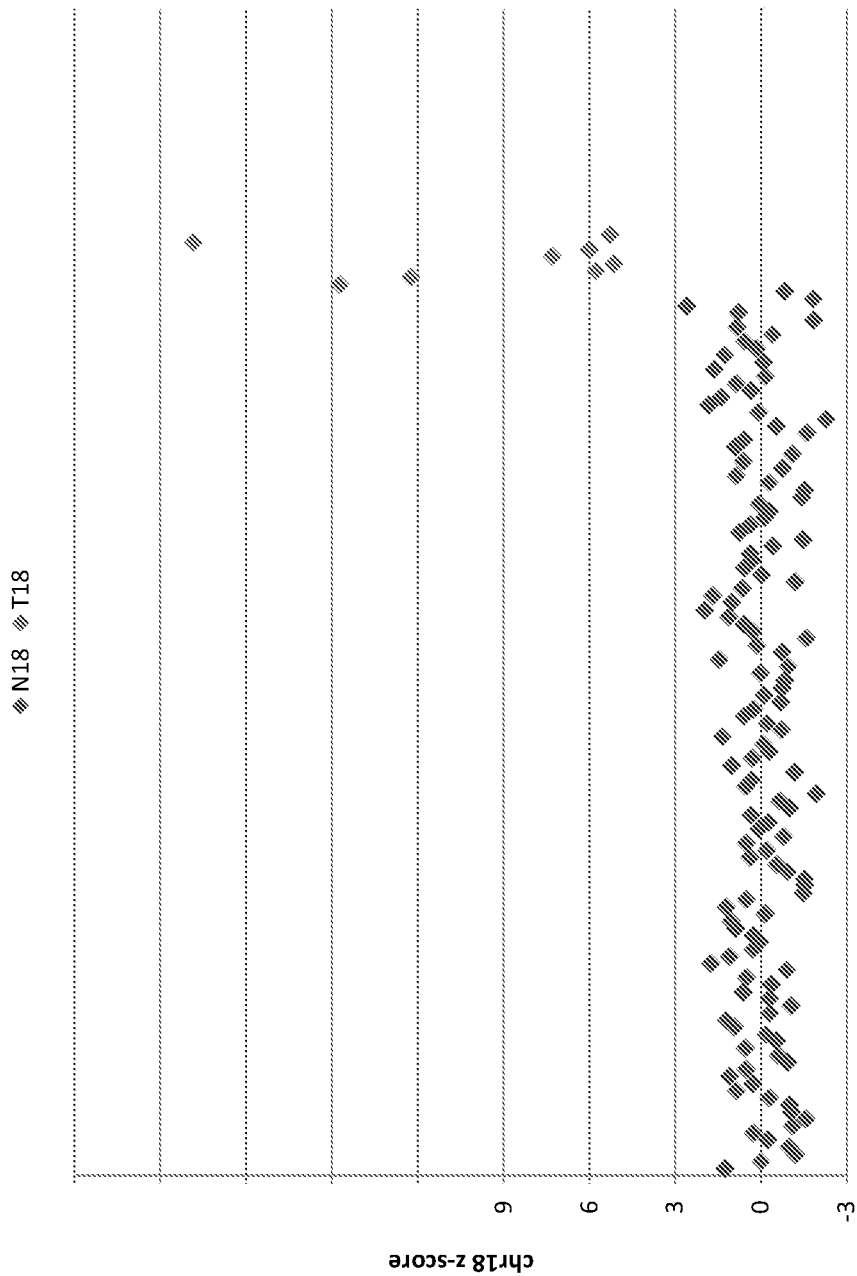
FIG. 11 illustrates the chromosome 18 aneuploidy detection achieved using one aspect of the invention for a second cohort.

The data provided in FIG. 7 was combined with data from the remaining samples of the second cohort to determine z-scores for chromosome 21 and chromosome 18 are illustrated in FIGS. 10 and 11, respectively. The normal samples are shown as dark grey diamonds, and the samples with a trisomy are shown as light grey diamonds. 125/125 normal samples had z-scores <3, 36/36 (100%) T21 and 8/8 (100%) T18 samples had z-scores >3. The mean T18 z-score was 9.5 and the range was 5.1-19.8. The mean T21 z-score was 11.4 and the range was 3.4-21.8.

In addition to the detection of aneuploidy in these cohorts, specific polymorphisms were also determined for these samples in a same assay. Specific information was obtained for individual loci as well as more general polymorphic information, such as the number of loci in which the fetal locus displayed a single nucleotide polymorphism in one allele different from the single nucleotide polymorphisms at the maternal locus (FIG. 7, #Locus DiffPoly). This determination also identified the presence of specific polymorphisms in the fetal genome. For example, the status of three exemplary polymorphism were determined using a combination of bridging oligos that were designed to bind to both the A and the T residue in the following exemplary polymorphic regions:

TABLE 3

Individual Polymorphisms Queried Using the Invention Assay

| Chromosome | Location | RSID |
|---|---|---|
| Ch01 | 01_010303942 | rs11582123 |
| TTTACATGTCTTTGGGCATTTTAGGT[A/T]GAGTGAAATCTAGGCCTTG CAAATC (SEQ ID NO: 7) | | |
| Ch03 | 03_098690592 | rs2470750 |
| TTGTGTAACGTTAACCTCAGGGACCA[A/T]GAGATGTACTTAGTATTAA TTTGCC (SEQ ID NO: 8) | | |
| Ch04 | 04_055495793 | rs6815910 |
| GGAAGAAGTGCAGTGTAGTAGACAAC[A/T]CTGGCATTGTGTTTTGTGA ACTGGG (SEQ ID NO: 9) | | |

TABLE 4

Predicted Maternal and Fetal Status for SNP rs11582123

| Sample | SNP | A counts | T counts | Predicted Fetal Status | Predicted Maternal Status |
|---|---|---|---|---|---|
| 1 | rs11582123 | 294 | 26 | A/T | A/A |
| 2 | | 181 | 134 | A/A | A/T |
| 4 | | 34 | 330 | A/T | T/T |
| 5 | | 241 | 21 | A/T | A/A |
| 6 | | 166 | 134 | A/T | A/T |
| 7 | | 137 | 182 | T/T | A/T |
| 8 | | 199 | 135 | A/A | A/T |
| 9 | | 0 | 267 | T/T | T/T |
| 10 | | 0 | 284 | T/T | T/T |
| 11 | | 151 | 154 | A/T | A/T |
| 12 | | 294 | 1 | A/T | A/A |
| 13 | | 131 | 114 | A/A | A/T |
| 14 | | 118 | 159 | T/T | A/T |
| 15 | | 257 | 10 | A/T | A/A |
| 16 | | 309 | 31 | A/T | A/A |
| 17 | | 20 | 289 | A/T | T/A |
| 18 | | 137 | 166 | T/T | A/T |
| 19 | | 138 | 143 | A/T | A/T |
| 20 | | 24 | 242 | A/T | T/T |
| 21 | | 140 | 161 | A/T | A/T |
| 22 | | 159 | 118 | A/A | A/T |
| 23 | | 119 | 122 | A/T | A/T |
| 24 | | 0 | 250 | T/T | T/T |
| 25 | | 0 | 285 | T/T | T/T |
| 26 | | 120 | 130 | A/T | A/T |
| 28 | | 134 | 113 | A/A | A/T |
| 29 | | 109 | 118 | A/T | A/T |
| 30 | | 0 | 271 | T/T | T/T |
| 31 | | 148 | 139 | A/T | A/T |
| 32 | | 29 | 253 | A/T | T/T |
| 33 | | 0 | 304 | T/T | T/T |
| 34 | | 0 | 278 | T/T | T/T |
| 35 | | 103 | 188 | T/T | A/T |
| 36 | | 18 | 269 | A/T | T/T |

TABLE 4-continued

Predicted Maternal and Fetal Status for SNP rs11582123

| Sample | SNP | A counts | T counts | Predicted Fetal Status | Predicted Maternal Status |
|---|---|---|---|---|---|
| 37 | | 279 | 34 | A/T | A/A |
| 38 | | 0 | 250 | T/T | T/T |
| 39 | | 0 | 263 | T/T | T/T |
| 40 | | 136 | 142 | A/T | A/T |
| 41 | | 147 | 145 | A/T | A/T |
| 42 | | 15 | 270 | A/T | T/T |
| 43 | | 44 | 222 | A/T | T/T |
| 44 | | 140 | 159 | T/T | A/T |
| 45 | | 0 | 259 | T/T | T/T |
| 46 | | 1 | 304 | T/T | T/T |
| 47 | | 162 | 127 | A/A | A/T |
| 48 | | 0 | 335 | T/T | T/T |
| 49 | | 1 | 247 | T/T | T/T |
| 50 | | 153 | 154 | A/T | A/T |
| 51 | | 118 | 182 | T/T | A/T |
| 52 | | 145 | 134 | A/T | A/T |
| 53 | | 146 | 132 | A/T | A/T |
| 54 | | 7 | 319 | A/T | T/T |
| 55 | | 152 | 174 | T/T | A/T |
| 56 | | 1 | 319 | T/T | T/T |
| 57 | | 147 | 150 | A/T | A/T |
| 58 | | 136 | 157 | T/T | A/T |
| 59 | | 83 | 162 | A/A | T/T |
| 60 | | 14 | 215 | A/T | T/T |
| 61 | | 157 | 121 | A/A | A/T |
| 62 | | 281 | 0 | A/A | A/A |
| 63 | | 0 | 260 | T/T | T/T |
| 64 | | 0 | 305 | T/T | T/T |
| 65 | | 18 | 252 | A/T | T/T |
| 66 | | 0 | 303 | T/T | T/T |
| 67 | | 99 | 161 | T/T | A/T |
| 68 | | 141 | 127 | A/T | A/T |
| 69 | | 0 | 237 | T/T | T/T |
| 70 | | 0 | 315 | T/T | T/T |
| 71 | | 132 | 139 | A/T | A/T |
| 73 | | 112 | 120 | A/T | A/T |
| 75 | | 1 | 268 | T/T | T/T |
| 76 | | 166 | 123 | A/A | A/T |
| 78 | | 0 | 245 | T/T | T/T |
| 79 | | 12 | 264 | A/T | T/T |
| 80 | | 15 | 281 | A/T | T/T |
| 81 | | 21 | 269 | A/T | T/T |
| 82 | | 108 | 160 | T/T | A/T |
| 83 | | 106 | 144 | T/T | A/T |
| 84 | | 137 | 135 | A/T | A/T |
| 85 | | 115 | 151 | T/T | A/T |
| 86 | | 0 | 262 | T/T | T/T |
| 87 | | 0 | 269 | T/T | T/T |
| 89 | | 0 | 284 | T/T | T/T |
| 90 | | 0 | 261 | T/T | T/T |
| 91 | | 143 | 137 | A/T | A/T |
| 92 | | 0 | 308 | T/T | T/T |
| 93 | | 1 | 256 | T/T | T/T |
| 94 | | 158 | 105 | A/A | A/T |
| 95 | | 149 | 103 | A/A | A/T |

TABLE 5

Predicted Maternal and Fetal Status for SNP rs2470750

| Sample | SNP | A counts | T counts | Predicted Fetal Status | Predicted Maternal Status |
|---|---|---|---|---|---|
| 1 | rs2470750 | 243 | 15 | A/T | A/A |
| 2 | | 265 | 0 | A/A | A/A |
| 4 | | 170 | 107 | A/A | A/T |
| 5 | | 196 | 30 | A/T | A/A |
| 6 | | 141 | 144 | A/T | A/T |
| 7 | | 139 | 137 | A/T | A/T |
| 8 | | 272 | 0 | A/A | A/A |

TABLE 5-continued

Predicted Maternal and Fetal Status for SNP rs2470750

| Sample | SNP | A counts | T counts | Predicted Fetal Status | Predicted Maternal Status |
|---|---|---|---|---|---|
| 9 | | 218 | 0 | A/A | A/A |
| 10 | | 216 | 0 | A/A | A/A |
| 11 | | 228 | 0 | A/A | A/A |
| 12 | | 6 | 224 | A/T | T/T |
| 13 | | 126 | 93 | A/A | A/T |
| 14 | | 125 | 123 | A/T | A/T |
| 15 | | 234 | 20 | A/A | A/A |
| 16 | | 147 | 113 | A/A | A/T |
| 17 | | 235 | 2 | A/T | A/A |
| 18 | | 129 | 142 | A/T | A/T |
| 19 | | 132 | 114 | A/A | A/T |
| 20 | | 214 | 0 | A/A | A/A |
| 21 | | 1 | 245 | T/T | T/T |
| 22 | | 141 | 111 | A/A | A/T |
| 23 | | 135 | 128 | A/A | A/T |
| 24 | | 121 | 160 | T/T | A/T |
| 25 | | 209 | 21 | A/T | A/A |
| 26 | | 0 | 239 | T/T | T/T |
| 27 | | 203 | 4 | A/T | A/A |
| 28 | | 101 | 115 | T/T | A/T |
| 29 | | 212 | 10 | A/T | A/A |
| 30 | | 86 | 101 | T/T | A/T |
| 31 | | 118 | 116 | A/T | A/T |
| 32 | | 135 | 121 | A/A | A/T |
| 33 | | 111 | 128 | T/T | A/T |
| 34 | | 120 | 118 | A/T | A/T |
| 35 | | 246 | 0 | A/A | A/A |
| 36 | | 113 | 115 | A/T | A/T |
| 37 | | 96 | 126 | T/T | A/T |
| 38 | | 107 | 88 | A/A | A/T |
| 39 | | 241 | 0 | A/A | A/A |
| 40 | | 116 | 118 | A/T | A/T |
| 41 | | 135 | 89 | A/A | A/T |
| 42 | | 129 | 85 | A/A | A/T |
| 43 | | 0 | 205 | T/T | T/T |
| 44 | | 138 | 88 | A/A | A/T |
| 45 | | 129 | 86 | A/A | A/T |
| 46 | | 108 | 123 | T/T | A/T |
| 47 | | 14 | 246 | A/T | T/T |
| 48 | | 129 | 148 | T/T | A/T |
| 49 | | 108 | 110 | A/T | A/T |
| 50 | | 120 | 124 | A/T | A/T |
| 51 | | 212 | 22 | A/T | A/T |
| 52 | | 237 | 0 | A/A | A/A |
| 53 | | 104 | 147 | T/T | A/T |
| 54 | | 134 | 126 | A/T | A/T |
| 55 | | 128 | 82 | A/A | A/T |
| 56 | | 225 | 5 | A/T | A/A |
| 57 | | 213 | 11 | A/T | A/A |
| 58 | | 125 | 116 | A/T | A/T |
| 59 | | 226 | 1 | A/A | A/A |
| 60 | | 103 | 119 | T/T | A/T |
| 61 | | 84 | 91 | T/T | A/T |
| 62 | | 130 | 104 | A/A | A/T |
| 63 | | 251 | 0 | A/A | A/A |
| 64 | | 243 | 0 | A/A | A/A |
| 65 | | 127 | 115 | A/A | A/T |
| 66 | | 113 | 104 | A/A | A/T |
| 67 | | 26 | 190 | A/T | T/T |
| 68 | | 80 | 83 | A/T | A/T |
| 69 | | 122 | 132 | T/T | A/T |
| 70 | | 0 | 235 | T/T | T/T |
| 71 | | 90 | 123 | T/T | A/T |
| 73 | | 174 | 0 | A/A | A/A |
| 75 | | 0 | 233 | T/T | T/T |
| 76 | | 220 | 0 | A/A | A/A |
| 78 | | 115 | 115 | A/T | A/T |
| 79 | | 112 | 144 | T/T | A/T |
| 80 | | 10 | 248 | A/T | T/T |
| 81 | | 241 | 0 | A/A | A/A |
| 82 | | 228 | 0 | A/A | A/A |
| 83 | | 243 | 16 | A/T | A/A |
| 84 | | 133 | 104 | A/A | A/T |
| 85 | | 101 | 99 | A/T | A/T |
| 86 | | 1 | 209 | A/A | A/A |
| 87 | | 224 | 7 | A/T | A/A |
| 89 | | 122 | 101 | A/A | A/T |
| 90 | | 130 | 89 | A/A | A/T |
| 91 | | 128 | 151 | T/T | A/T |
| 92 | | 231 | 0 | A/A | A/A |
| 93 | | 107 | 118 | T/T | A/T |
| 94 | | 93 | 100 | A/T | A/T |
| 95 | | 132 | 119 | A/A | A/T |

TABLE 6

Predicted Maternal and Fetal Status for SNP rs6815910.

| Sample | SNP | A counts | T counts | Predicted Fetal Status | Predicted Maternal Status |
|---|---|---|---|---|---|
| 1 | rs6815910 | 295 | 32 | A/T | A/A |
| 10 | | 133 | 107 | A/A | A/T |
| 11 | | 115 | 131 | T/T | A/T |
| 12 | | 311 | 10 | A/T | A/A |
| 13 | | 18 | 252 | A/T | T/T |
| 14 | | 132 | 178 | T/T | A/T |
| 15 | | 288 | 0 | A/A | A/A |
| 16 | | 325 | 1 | A/A | A/A |
| 17 | | 11 | 276 | A/T | T/T |
| 18 | | 282 | 0 | A/A | A/A |
| 19 | | 131 | 133 | A/T | A/T |
| 2 | | 7 | 311 | A/T | T/T |
| 20 | | 135 | 116 | A/T | A/T |
| 21 | | 121 | 140 | T/T | A/T |
| 22 | | 287 | 11 | A/T | A/A |
| 23 | | 148 | 146 | A/T | A/T |
| 24 | | 185 | 138 | A/A | A/T |
| 25 | | 116 | 126 | T/T | A/T |
| 26 | | 235 | 0 | A/A | A/A |
| 27 | | 288 | 0 | A/A | A/A |
| 28 | | 242 | 0 | A/A | A/A |
| 29 | | 239 | 12 | A/T | A/A |
| 30 | | 235 | 24 | A/T | A/A |
| 31 | | 126 | 148 | T/T | A/T |
| 32 | | 25 | 256 | A/T | T/T |
| 33 | | 286 | 1 | A/A | A/A |
| 34 | | 158 | 156 | A/T | A/T |
| 35 | | 287 | 0 | A/A | A/A |
| 36 | | 118 | 133 | T/T | A/T |
| 37 | | 163 | 119 | A/A | A/T |
| 38 | | 273 | 10 | A/A | A/A |
| 39 | | 132 | 148 | T/T | A/T |
| 4 | | 0 | 343 | T/T | T/T |
| 40 | | 143 | 177 | T/T | A/T |
| 41 | | 0 | 308 | T/T | T/T |
| 42 | | 297 | 0 | A/A | A/A |
| 43 | | 117 | 130 | T/T | A/T |
| 44 | | 296 | 1 | A/A | A/A |
| 45 | | 276 | 0 | A/A | A/A |
| 46 | | 140 | 134 | A/T | A/T |
| 47 | | 158 | 139 | A/T | A/T |
| 48 | | 0 | 304 | T/T | T/T |
| 49 | | 251 | 13 | A/T | A/A |
| 5 | | 138 | 115 | A/A | A/T |
| 50 | | 142 | 162 | T/T | A/T |
| 51 | | 0 | 306 | T/T | T/T |
| 52 | | 249 | 21 | A/T | A/A |
| 53 | | 111 | 170 | T/T | A/T |
| 54 | | 140 | 151 | A/T | A/T |
| 55 | | 102 | 217 | T/T | A/T |
| 56 | | 315 | 0 | A/A | A/A |
| 57 | | 123 | 158 | T/T | A/T |
| 58 | | 146 | 168 | T/T | A/T |

TABLE 6-continued

Predicted Maternal and Fetal Status for SNP rs6815910.

| Sample | SNP | A counts | T counts | Predicted Fetal Status | Predicted Maternal Status |
|---|---|---|---|---|---|
| 59 | | 226 | 50 | A/T | A/A |
| 6 | | 309 | 0 | A/A | A/A |
| 60 | | 122 | 133 | T/T | A/T |
| 61 | | 240 | 28 | A/T | A/A |
| 62 | | 132 | 124 | A/T | A/T |
| 63 | | 291 | 9 | A/T | A/A |
| 64 | | 0 | 304 | T/T | T/T |
| 65 | | 273 | 0 | A/A | A/A |
| 66 | | 154 | 139 | A/T | A/T |
| 67 | | 145 | 153 | A/T | A/T |
| 68 | | 110 | 163 | T/T | A/T |
| 69 | | 131 | 134 | A/T | A/T |
| 7 | | 186 | 127 | A/A | A/T |
| 70 | | 167 | 163 | A/T | A/T |
| 71 | | 238 | 26 | A/T | A/A |
| 73 | | 18 | 244 | A/T | T/T |
| 75 | | 130 | 129 | A/T | A/T |
| 76 | | 133 | 113 | A/A | A/T |
| 78 | | 237 | 2 | A/T | A/A |
| 79 | | 0 | 278 | T/T | T/T |
| 8 | | 192 | 159 | A/A | A/T |
| 80 | | 153 | 131 | A/A | A/T |
| 81 | | 25 | 229 | A/T | T/T |
| 82 | | 0 | 256 | T/T | T/T |
| 83 | | 152 | 142 | A/T | A/T |
| 84 | | 290 | 2 | A/T | A/A |
| 85 | | 270 | 0 | A/A | A/A |
| 86 | | 0 | 242 | T/T | T/T |
| 87 | | 150 | 134 | A/A | A/T |
| 89 | | 169 | 117 | A/A | A/T |
| 9 | | 271 | 1 | A/A | A/A |
| 90 | | 109 | 144 | T/T | A/T |
| 91 | | 261 | 12 | A/T | A/A |
| 92 | | 258 | 0 | A/A | A/A |
| 93 | | 0 | 309 | T/T | T/T |
| 94 | | 116 | 146 | T/T | A/T |
| 95 | | 123 | 116 | A/T | A/T |

The location of these SNPS is denoted using dbSNP version 132 and GRCH37/UCSC hg 19. The data for these polymorphisms was obtained in the same data set as the aneuploidy data illustrated in FIGS. 10 and 11. Thus, a single assay demonstrated the ability to identity fetal aneuploidy, polymorphic differences between fetal and maternal loci, and the actual SNP information for selected fetal loci in a single assay.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. A method for simultaneous detection of a presence or absence of a fetal copy number variation (CNV) of a genomic region and a presence or absence of one or more fetal polymorphisms in a maternal sample comprising fetal and maternal cell-free DNA, comprising the steps of:
(a) hybridizing at least 24 first sets of two fixed sequence oligonucleotides to the cell-free DNA in the maternal sample, wherein each first set is complementary to a locus in a first genomic region from a first chromosome or a first portion of a chromosome, wherein at least one of the two fixed sequence oligonucleotides in each first set comprises a universal primer region, wherein the two fixed sequence oligonucleotides of each first set hybridize immediately adjacent to each other, and wherein the melting temperatures ($T_m$s) of first fixed sequence oligonucleotides of each first set vary in a range of two degrees centigrade;
(b) hybridizing at least 24 second sets of two fixed sequence oligonucleotides to the cell-free DNA in the maternal sample, wherein each second set is complementary to a locus in a second genomic region from a second chromosome or a second portion of a chromosome, wherein at least one of the two fixed sequence oligonucleotides in each second set comprises a universal primer region, wherein the two fixed sequence oligonucleotides of each second set hybridize immediately adjacent to each other, and wherein the $T_m$s of first fixed sequence oligonucleotides of each second set vary in a range of two degrees centigrade;
(c) hybridizing a third set of two fixed sequence oligonucleotides to the cell-free DNA in the maternal sample, wherein the third set is complementary to a polymorphic locus, wherein at least one of the two fixed sequence oligonucleotides of the third set comprises a universal primer region, and wherein the two fixed sequence oligonucleotides of the third set hybridize immediately adjacent to each other;
(d) ligating the hybridized oligonucleotides of each first, second, and third set to create contiguous ligation products complementary to the loci in the first genomic region, the second genomic region, and the polymorphic locus;
(e) amplifying the contiguous ligation products using primers complementary to the universal primer regions of each first, second, and third set of two fixed sequence oligonucleotides to create amplification products;
(f) isolating the amplification products; and
(g) detecting
   (i) the presence or absence of a fetal polymorphism in the polymorphic locus; and
   (ii) the presence or absence of a fetal CNV by observing a statistical variation in the quantity of isolated amplification products of the first genomic region and the quantity of isolated amplification products of the second genomic region.

2. The method of claim 1, wherein the first and second genomic regions are located on the same chromosome.

3. The method of claim 1, wherein the first and second genomic regions are located on different chromosomes.

4. The method of claim 1, wherein the first genomic region, the second genomic region, and the polymorphic locus are located on different chromosomes.

5. The method of claim 1, wherein the isolated amplification products of the first genomic region, the second genomic region, and the polymorphic locus are detected by sequencing or hybridization.

6. The method of claim 5, wherein the isolated amplification products are isolated as individual molecules prior to sequencing or hybridization.

7. The method of claim 5, wherein the isolated amplification products are further amplified to create identical copies of all or a portion of the amplification products prior to sequencing or hybridization.

8. The method of claim 5, wherein the isolated amplification products are further amplified to create identical copies of molecules complementary to all or a portion of the amplification products prior to sequencing or hybridization.

9. The method of claim 5, wherein the universal primer regions are used in sequence determination of the amplification products.

10. The method of claim 1, wherein the first genomic region is located on a chromosome selected from the group consisting of chromosomes 13, 18, 21, 22, X, and Y.

11. The method of claim 1, wherein the second genomic region is located on a chromosome selected from the group consisting of chromosomes 13, 18, 21, 22, X, and Y.

12. The method of claim 1, wherein the polymorphic locus is located on a chromosome selected from the group consisting of chromosomes 1, 2, 3, 4, 5, 6, 7, 8, 9, 10, 11, 12, 14, 15, 16, 17, 19, 20, 23, and Y.

13. The method of claim 1, wherein one or more of each set of fixed sequence oligonucleotides comprises precircle probes.

14. The method of claim 1, wherein at least one locus in the first genomic region and at least one locus in the second genomic region do not comprise a polymorphism.

15. The method of claim 1, wherein the first and second genomic regions are each single genes.

16. A method for determining a likelihood of a fetal copy number variation (CNV) of a genomic region and a presence or absence of one or more fetal polymorphisms in a maternal sample comprising fetal and maternal cell-free DNA, comprising the steps of:
(a) hybridizing at least 24 first sets of two fixed sequence oligonucleotides to the cell-free DNA in the maternal sample, wherein each first set is complementary to a locus in a first genomic region from a first chromosome or a first portion of a chromosome, wherein at least one of the two fixed sequence oligonucleotides in each first set comprises a universal primer region, wherein the two fixed sequence oligonucleotides of each first set hybridize immediately adjacent to each other, and wherein the melting temperatures ($T_m$s) of first fixed sequence oligonucleotides of each first set vary in a range of two degrees centigrade;
(b) hybridizing at least 24 second sets of two fixed sequence oligonucleotides to the cell-free DNA in the maternal sample, wherein each second set is complementary to a locus in a second genomic region from a second chromosome or a second portion of a chromosome, wherein at least one of the two fixed sequence oligonucleotides in each second set comprises a universal primer region, wherein the two fixed sequence oligonucleotides of each second set hybridize immediately adjacent to each other, and wherein the $T_m$s of first fixed sequence oligonucleotides of each second set vary in a range of two degrees centigrade;
(c) hybridizing a third set of two fixed sequence oligonucleotides to the cell-free DNA in the maternal sample, wherein the third set of two fixed sequence oligonucleotides is complementary to a polymorphic locus, wherein at least one of the two fixed sequence oligonucleotides of the third set comprises a universal primer region, and wherein the two fixed sequence oligonucleotides of the third set hybridize immediately adjacent to each other;
(d) ligating the hybridized oligonucleotides of each first, second, and third set to create contiguous ligation products complementary to the loci in the first genomic region, the second genomic region, and the polymorphic locus;
(e) amplifying the contiguous ligation products using primers complementary to the universal primer regions of each first, second, and third set of two fixed sequence oligonucleotides to create amplification products;
(f) isolating the amplification products;
(g) detecting the isolated amplification products; and
(h) determining
(i) a likelihood of a fetal CNV using the quantified total isolated amplification products corresponding to the first genomic region and the quantified total amplification products corresponding to the second genomic region; wherein a likelihood of a fetal CNV is indicated if the quantified total of amplification products from the loci of first and second genomic regions vary statistically; and
(ii) the presence or absence of a fetal polymorphism from the isolated amplification products corresponding to the polymorphic locus.

17. The method of claim 16, wherein the first and second genomic regions are located on the same chromosome.

18. The method of claim 16, wherein the first and second genomic regions are located on different chromosomes.

19. The method of claim 16, wherein the first genomic region, the second genomic region, and the polymorphic locus are located on different chromosomes.

20. The method of claim 16, wherein the isolated amplification products of the first genomic region, the second genomic region, and the polymorphic locus are detected by sequencing or hybridization.

21. The method of claim 20, wherein the isolated amplification products are isolated as individual molecules prior to sequencing or hybridization.

22. The method of claim 20, wherein the individual isolated amplification products are further amplified to create identical copies of all or a portion of the individual amplification products prior to sequencing or hybridization.

23. The method of claim 20, wherein the individual isolated amplification products are further amplified to create identical copies of molecules complementary to all or a portion of the individual amplification products prior to sequencing or hybridization.

24. The method of claim 20, wherein the universal primer regions are used in sequence determination of the isolated amplification products.

25. The method of claim 16, wherein the first genomic region is located on a chromosome selected from the group consisting of chromosomes 13, 18, 21, 22, X, and Y.

26. The method of claim 16, wherein the second genomic region is located on a chromosome selected from the group consisting of chromosomes 13, 18, 21, 22, X, and Y.

27. The method of claim 16, wherein the polymorphic locus is located on a chromosome selected from the group consisting of chromosomes 1, 2, 3, 4, 5, 6, 7, 8, 9, 10, 11, 12, 14, 15, 16, 17, 19, 20, 23, and Y.

28. The method of claim 16, wherein one or more of each set of fixed sequence oligonucleotides comprises a precircle probe.

29. The method of claim 16, wherein at least one locus in the first genomic region and at least one locus in the second genomic region do not comprise a polymorphism.

30. The method of claim 16, wherein the first and second genomic regions are each single genes.

\* \* \* \* \*

SEQUENCE LISTING

```
<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
tacaccggcg ttatgcgtcg agac                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
attgcgggga ccgatgatcg cgtc                                              24

<210> SEQ ID NO 3
<211> LENGTH: 48
<212> TYPE: DNA
<213> ORGANISM: Artificial Sequence
<220> FEATURE:
<223> OTHER INFORMATION: Synthetic oligonucleotide
```

<400> SEQUENCE: 3
taatgatacg gcgaccaccg agatctacac cggcgttatg cgtcgaga         48

<210> SEQ ID NO 4
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(26)
<223> OTHER INFORMATION: n = a, c, g, or t

<400> SEQUENCE: 4
tcaagcagaa gacggcatac gagatnaaac gacgcgatca tcggtccccg caa         53

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
taatgatacg gcgaccaccg a         21

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
atctcgtatg ccgtcttctg cttga         25

<210> SEQ ID NO 7
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 7
aatgatacgg cgaccaccga gatctacacc ggcgttatgc gtcgagac         48

<210> SEQ ID NO 8
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(32)
<223> OTHER INFORMATION: n = a, c, g, or t

<400> SEQUENCE: 8
tcaagcagaa gacggcatac gagatnnnnn nnaaacgacg cgatcatcgg tccccgcaat         60

<210> SEQ ID NO 9
<211> LENGTH: 52
<212> TYPE: DNA
<213> ORGANISM: Artificial Sequence
<220> FEATURE:

```
<223> OTHER INFORMATION: Synthetic oligonucleotide
<220> FEATURE:
<221> NAME/KEY: misc_feature
<222> LOCATION: (27)..(27)
<223> OTHER INFORMATION: w = a or t

<400> SEQUENCE: 9
tttacatgtc tttgggcatt ttaggtwgag tgaaatctag gccttgcaaa tc           52

<210> SEQ ID NO 10
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (27)..(27)
<223> OTHER INFORMATION: w = a or t

<400> SEQUENCE: 10
ttgtgtaacg ttaacctcag ggaccawgag atgtacttag tattaatttg cc           52

<210> SEQ ID NO 11
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (27)..(27)
<223> OTHER INFORMATION: w = a or t

<400> SEQUENCE: 11
ggaagaagtg cagtgtagta dacaacwctg gcattgtgtt ttgtgaactg gg           52
```